United States Patent
Francis et al.

(10) Patent No.: US 11,672,883 B2
(45) Date of Patent: Jun. 13, 2023

(54) SHAPE MEMORY ARTICLES AND METHODS FOR CONTROLLING PROPERTIES

(71) Applicant: Medtronic Inc., Minneapolis, MN (US)

(72) Inventors: Richard Francis, Santa Rosa, CA (US); Brett Vegoe, Santa Rosa, CA (US); Curtis Goreham-Voss, Santa Rosa, CA (US); Dhiraj Catoor, Santa Rosa, CA (US); Scott Robertson, San Francisco, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 357 days.

(21) Appl. No.: 15/965,284

(22) Filed: Apr. 27, 2018

(65) Prior Publication Data

US 2018/0311406 A1 Nov. 1, 2018

Related U.S. Application Data

(60) Provisional application No. 62/529,121, filed on Jul. 6, 2017, provisional application No. 62/491,423, filed on Apr. 28, 2017.

(51) Int. Cl.
*A61L 27/04* (2006.01)
*C22F 1/10* (2006.01)
(Continued)

(52) U.S. Cl.
CPC ............. *A61L 27/047* (2013.01); *A61L 27/06* (2013.01); *A61L 27/50* (2013.01); *C22C 1/02* (2013.01); *C22C 14/00* (2013.01); *C22C 19/03* (2013.01); *C22F 1/006* (2013.01); *C22F 1/10* (2013.01); *A61F 2/2418* (2013.01); *A61F 2/86* (2013.01); *A61F 2/91* (2013.01); *A61F 2210/0014* (2013.01); *A61F 2210/0019* (2013.01);
(Continued)

(58) Field of Classification Search
CPC ...... A61F 2/82; A61F 2/89; A61F 2/91; A61F 2/24; A61L 27/04; C22F 1/10
See application file for complete search history.

(56) References Cited

U.S. PATENT DOCUMENTS 6,106,642 A 8/2000 DiCarlo et al.
2002/0177891 A1 11/2002 Parodi
(Continued)

FOREIGN PATENT DOCUMENTS

CN 102056575 5/2011
CN 103409663 11/2013
(Continued)

OTHER PUBLICATIONS

Introduction to Nitinol, Saes Group Company Memry, Dec. 28, 2017 (Dec. 28, 2017), pp. 1-40, XP002785007, USA the whole document.

(Continued)

*Primary Examiner* — Matthew W Schall
(74) *Attorney, Agent, or Firm* — Wentsler LLC

(57) ABSTRACT

Methods for controlling properties of structural elements of implantable medical devices, where the structural elements contain shape memory alloys (SMAs) include promoting or inhibiting in vivo formation of R-phase crystal structure or converging or separating the R-phase from the austenite phase.

5 Claims, 42 Drawing Sheets

(51) Int. Cl.
| | |
|---|---|
| C22C 1/02 | (2006.01) |
| A61L 27/06 | (2006.01) |
| C22C 19/03 | (2006.01) |
| C22C 14/00 | (2006.01) |
| C22F 1/00 | (2006.01) |
| A61L 27/50 | (2006.01) |
| A61F 2/24 | (2006.01) |
| A61F 2/86 | (2013.01) |
| A61F 2/91 | (2013.01) |

(52) U.S. Cl.
CPC ..... *A61F 2240/001* (2013.01); *A61L 2400/16* (2013.01); *A61L 2430/20* (2013.01); *C21D 2201/01* (2013.01)

(56) References Cited

U.S. PATENT DOCUMENTS

| | | |
|---|---|---|
| 2002/0185200 A1 | 12/2002 | DiCarlo et al. |
| 2011/0247731 A1 | 10/2011 | Gordon |
| 2012/0227302 A1 | 9/2012 | Fonte |
| 2016/0101221 A1* | 4/2016 | Flomenblit ........... A61L 31/022 623/1.18 |

FOREIGN PATENT DOCUMENTS

| | | |
|---|---|---|
| JP | 62211339 | 9/1987 |
| WO | 1999/16385 | 4/1999 |
| WO | WO 99/16385 A1 | 4/1999 |
| WO | 2009/070784 | 6/2009 |
| WO | WO 2009/070784 A1 | 6/2009 |
| WO | 2009/131689 | 10/2009 |
| WO | WO 2009/131689 A1 | 10/2009 |

OTHER PUBLICATIONS

PCT communication dated Nov. 9, 2018 in corresponding PCT Appln. No. PCT/US2018/03053.
Ashby, *Engineering Materials and Processes Desk Reference, Metallic Fatigue*, Butterworth-Heinemann, Oxford, UK, 2009, Title page, copyright page and pp. 213-221.
Fonte and Saigal, "Shape recovery effects of solid, forged nitinol for orthopedic applications," Medical Device Materials V; Proceedings from the Materials & Processes for Medical Devices Conference 2009 (ASM International), Aug. 10-12, 2009, Minneapolis, Minnesota, USA, Published April 1. 2010; pp. 217-247. Abstract only. Database Compendex [Online] Engineering Information, Inc., New York, NY, US; 2010. Database accession No. E20103413181207.
Partial International Search Report and Provisional Opinion for International Application No. PCT/US2018/030053, dated Aug. 10, 2018, 10 pages.
Andreasen and Morrow, "Laboratory and clinical analyses of nitinol wire," *Am J Orthod*, 1978; 73(2):142-151.
Asgharnia and Brantley, "Comparison of bending and tension tests for orthodontic wires," *Am J Orthod*, 1986; 89(3):228-235.
ASTM F2004—05(2010)—Standard Test Method for Transformation Temperature of Nickel-Titanium Alloys by Thermal Analysis; 5 pages.
Benafan et al., "Temperature dependent deformation of the B2 austenite phase of a NiTi shape memory alloy," *International Journal of Plasticity*, 2013; 51:103-121.
Bergstrom and Roberts, "The dynamical strain ageing of α-iron: effects of strain rate and nitrogen content in the jerky-flow region," *Acta. Met.*, 1973; 21(6):741.
Čapek and Kubásek, "Influence of short-period heat treatment on mechanical properties of NiTi wires," *ICOMAT 2012, Recent trends in structural materials*, Nov. 21, 2012; 5 pages.

Crussard and Jaoul, "Contribution à l' étude de la forme des courbes de traction des métaux et à son interpretation physique," *Revue de Métallurgie*, 1950; 47(8):589-600.
Crussard, "Rapport entre la forme exacte des courbes de traction des métaux et les modifications concomitantes de leur structure," *Revue de Métallurgie*, 1953; 50(10):697-710.
Defense Documentation Center—Unclassified Report #426344. "The Engineering Properties of Tantalum and Tantalum Alloys," DMIC Report 189, Sep. 13, 1963; 121 pages.
Drake et al., "Mechanical properties of orthodontic wires in tension, bending, and torsion," *Am J Orthod*. Sep. 1982; 82(3):206-210.
Fonte & Saigal, "Shape Recovery Effects of Solid, Forged Nitinol for Orthopedic Applications," Medical Device Materials V, Proceedings from the Materials & Processes for Medical Devices Conference, Aug. 10-12, 2009, Minneapolis, Minnesota; pp. 241-247.
Goldberg et al., "The flexure modulus of elasticity of orthodontic wires," *J Dent Res.*, Jul. 1983; 62(7):856-858.
J. H. Hollomon, "Tensile Deformation," *Transactions of the American Institute of Mining and Metallurgical Engineers*, 1945; 162:268-290.
Jaoul, "Etude de la forme des courbes de deformation plastique," *J. Mech. Phys. Solids*, 1957; 5:95-114.
Kusy and Stush, "Geometric and material parameters of a nickel-titanium and a beta titanium orthodontic arch wire alloy," *Dent Mater*, 1987; 3:207-217.
Ledbetter and Naimon, "Elastic Properties of Metals and Alloys. II. Copper," *Journal of Physical and Chemical Reference Data*, 1974; 3(4):912-923.
Ludwigson, "Modified stress-strain relation for FCC metals and alloys," *Met. Trans.*, 1971; 2:2825-2828.
McGrath and Thurston, "The effect of cross slip on the fatigue behavior of copper and copper-zinc alloys," *Trans. Metall. Soc. AIME*, 1963; 227:645.
McKelvey & Ritchie, "On the temperature dependence of the superelastic strength and the prediction of the theoretical uniaxial transformation strain in Nitinol," *Philosophical Magazine A*, 2000; 80(8):1759-1768.
Mecking and Lücke, "Quantitative analysis of stage III hardening of silver single crystals," *Acta Metall*, 1969; 17:279.
Mecking, "Description of Hardening Curves of FCC Single and Polycrystals," in: *Work Hardening in Tension and Fatigue*, ed. A.W. Thompson, 1977, American Institute of Mining, Metallurgical and Petroleum Engineers, Inc., New York, New York; pp. 67-88.
Pascual and Meeker, "Estimating Fatigue Curves with the Random Fatigue-Limit Mode," *Statistics Preprints*, 12; 33 pages.
Pelton et al., "In Situ Neutron Diffraction Studies of Increasing Tension Strains of Superelastic Nitinol," *Shap Mem Superelasticity*, 2015; 1:375-386.
Ramberg and Osgood, "Description of Stress-Strain Curves by Three Parameters," National Advisory Committee for Aeronautics Technical Notes No. 902, 1943, 29 pages.
Starke and Lutjering, "Cyclic Plastic Deformation and Microstructure," in *Fatigue and Microstructure, Papers presented at the 1978 ASM Materials Science Seminar*, American Society for Metals, Metals Park, OH; pp. 205-243.
Stoeckel & Yu, "Superelastic Ni-Ti Wire—The Transformational Superelasticity in Ni-Ti Wire is About Ten Times Higher Than the Elasticity in Ordinary Materials," *Wire Journal International*, Mar. 1991; pp. 45-50.
Swift, "Plastic instability under plane stress," *Journal of the Mechanics and Physics of Solids*, 1952, 1:1-18.
Voce, "The Relationship Between Stress and Strain for Homogeneous Deformation," *Inst. Metals*, 1948; 74:537-562.
Zapoticla, MSc Dissertation, *The Effects of Applied Strain and Heat Treatment on the Properties of NiTi Wire During Shape Setting*, California Polytechnic State University, San Luis Obispo, Jun. 2010; 131 pages.
Chinese Office Action from CN Application No. 201880028153.3 dated Mar. 3, 2021, 9 pages.

* cited by examiner

| Shape Setting Conditions | | | Resulting Performance | | | | | | |
|---|---|---|---|---|---|---|---|---|---|
| Embod-iment | Temp | Stress/Strain | Delivery Force | Chronic Outward Force | Crush Resistive Force | Force Fatigue Resist. | Displ Fatigue Resist. | UPS | AFM |
| 1a | Low | Zero | Lowest | Lowest | Low | Low | High | Lowest | High |
| 1b | High | Zero | Low | Low | Lowest | Lowest | Highest | Low | Low |
| 2a | Low | Non-Zero | High | High | Highest | Highest | Lowest | High | High |
| 2b | High | Non-Zero | Highest | Highest | High | High | Low | Highest | Low |

FIG. 12

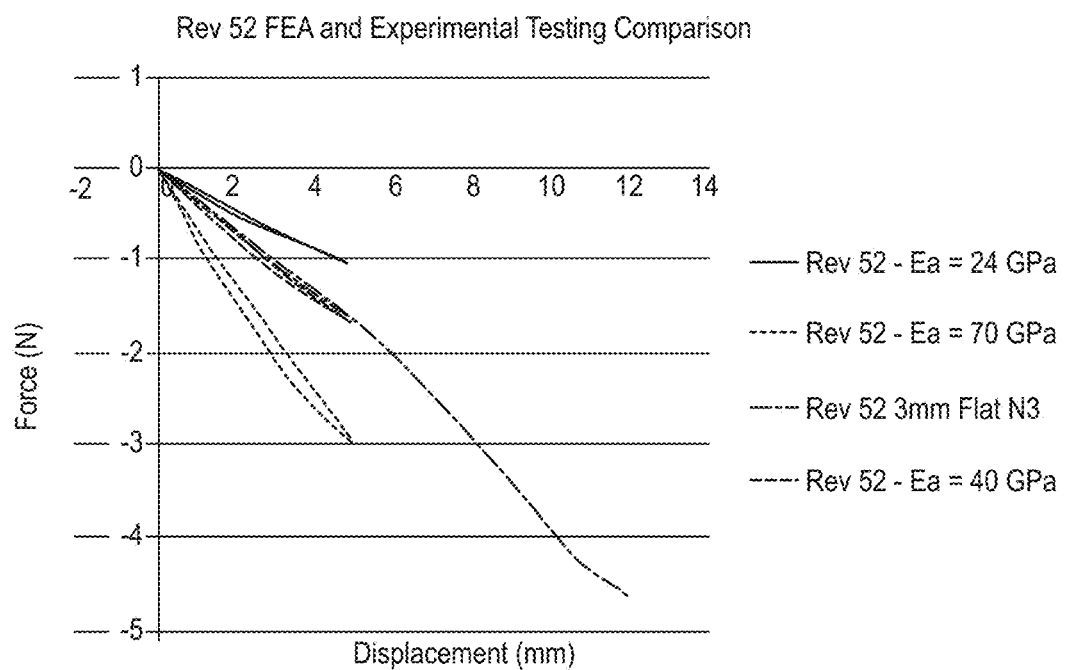
FIG. 17B
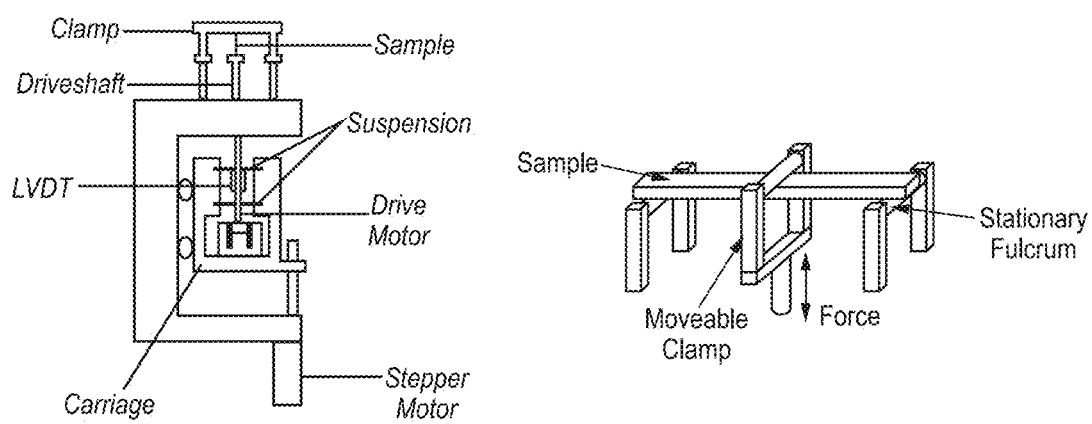
FIG. 18A  FIG. 18B

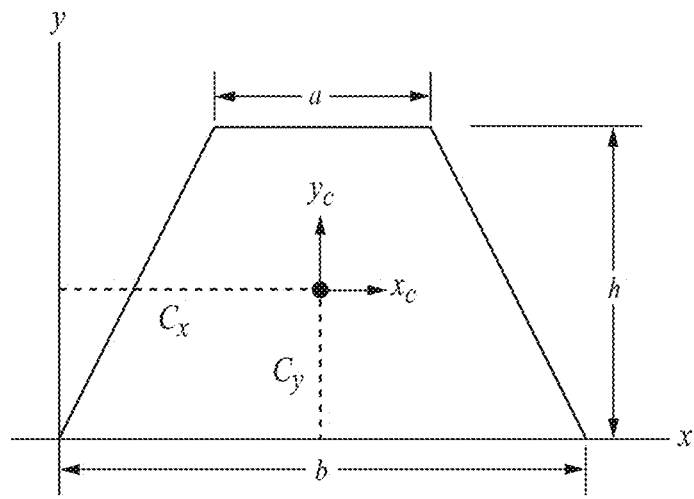
FIG. 21
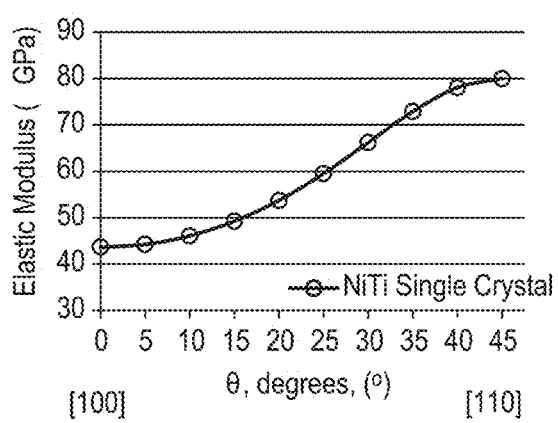
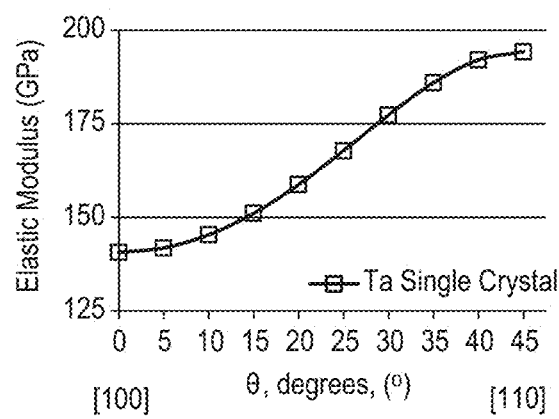
FIG. 22A     FIG. 22B

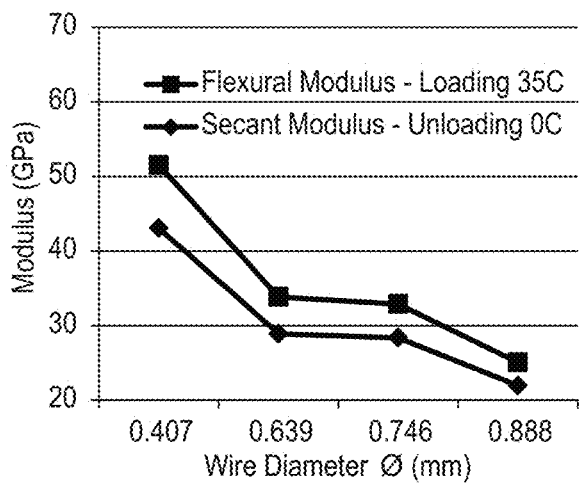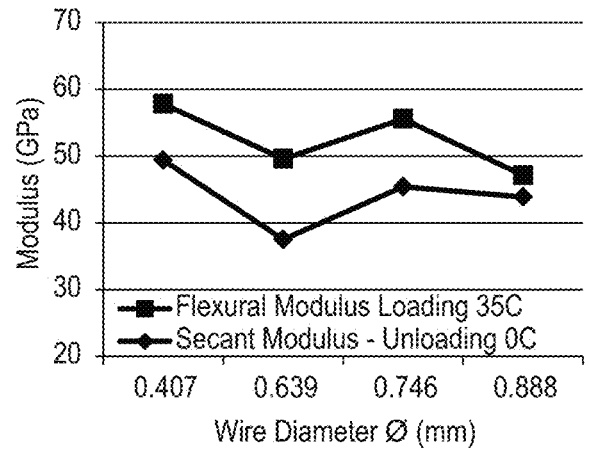
FIG. 40A  FIG. 40B
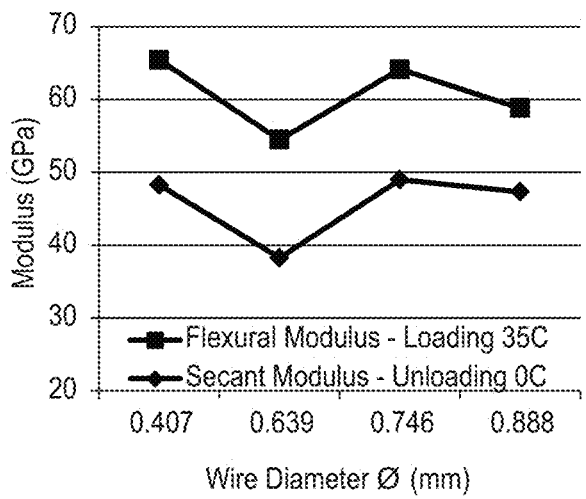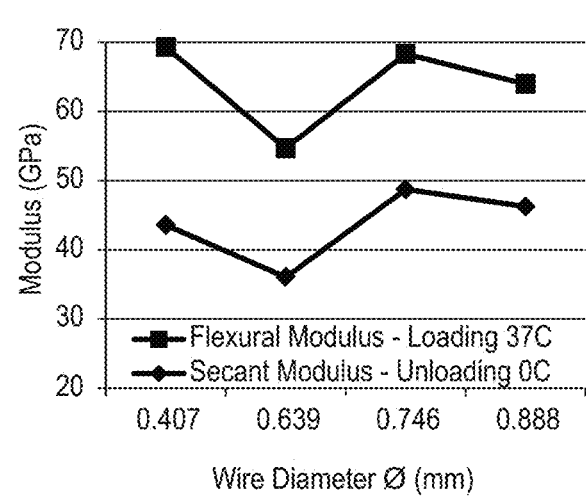
FIG. 40C  FIG. 40D (a) Cross-section of plate.

(b) Bending stress diagram.

(c) Shear stress diagram.

SHAPE MEMORY ARTICLES AND METHODS FOR CONTROLLING PROPERTIES

RELATED APPLICATIONS

This application claims the benefit of U.S. Provisional Application No. 62/491,423, filed on Apr. 28, 2017 and U.S. Provisional Patent Application No. 62/529,121, filed on Jul. 6, 2017, which provisional patent applications are hereby incorporated herein by reference in their respective entireties.

FIELD

The present disclosure relates to articles, such as implantable medical devices or components thereof, formed from a superelastic or pseudoelastic shape memory alloys, such as nitinol shape memory alloy.

BACKGROUND

When processed appropriately, certain alloy compositions e.g. alloys of an approximate equiatomic nickel and titanium composition (nitinol), exhibit two atypical behaviors: the shape memory effect (SME); and pseudoelasticity. The shape memory effect describes the ability of an article fabricated from a shape memory alloy (SMA) to revert to its original shape and configuration; e.g., upon heating after being deformed at a sufficiently low temperature. Above a defined transformation temperature, the SMA can also exhibit pseudoelasticity which is more commonly referred to as superelasticity (SE). In the superelastic condition; an article fabricated from SMA can undergo large mechanical deformations and revert to its original configuration upon unloading. Both the shape memory effect and the superelastic behavior are the result of reversible martensite phase transformations. Martensitic transformations manifest themselves as the diffusionless rearrangement of atoms promoted by the material's attempts to reduce its internal energy in response to application of specific external stimuli. A stimulus might be a change in temperature for example, or the application of a mechanical stress.

At elevated temperatures, nitinol assumes an austenite crystal structure which is referred to as the parent phase. At low temperatures, nitinol SMA assumes a martensite crystal structure which may be referred to as the daughter phase. The temperatures at which the material transforms from one structure or phase to another structure or phase is referred to as a transformation temperature. The transformations occur over a temperature range; therefore, four transition temperatures are typically defined for the reversible martensite to austenite phase transformation. The austenite finish temperature ($A_f$) is commonly used and key transformation temperature for the specification of SMAs.

With regard to SMAs, such as nitinol, the following definitions are typically used in the art:

A. $A_f$: Austenite finish temperature—the temperature at which the martensite-to-austenite transformation is complete on heating.
B. $A_s$: Austenite start temperature—the temperature at which the martensite-to-austenite transformation begins on heating.
C. $M_s$: Martensite start temperature—the temperature at which the austenite-to-martensite transformation begins on cooling.
D. $M_f$: Martensite finish temperature—the temperature at which the austenite-to martensite transformation is complete on cooling.
E. Austenite: A high-temperature solid phase, possessing a body-centered cubic symmetry crystal structure. Austenite is the predominant phase concurrent with superelastic behavior, it is rigid and springy.
F. Martensite: A low-temperature solid phase, possessing a monoclinic crystal structure. Martensite is readily deformed, soft and bendable. Once deformed the martensite phase material will remain deformed until it is heated such that it transforms to austenite where it will return to its pre-deformed shape, this thermally driven transformation is the origin of the shape memory effect.

Shape memory materials are materials that have the ability to return from one shape to another shape upon application of a thermodynamic driving force, such as stress or a change in temperature. Shape memory materials include SMAs, such as nitinol, and have been used extensively in a variety of industries, including the medical device industry.

For example, shape memory materials are advantageously used in medical devices that expand during or following implant. Accordingly, the devices may be compressed to assume a low profile to facilitate implantation and may then expand to assume their functional shape following implant. Such devices include heart valves, stents, vascular grafts, etc. Other devices or elements of implantable medical devices that may include self-expanding shape memory materials include fixation elements which can expand after deployment to retain the device, or a portion thereof, in a desired shape and location. Other devices using the shape memory properties of SMAs include catheters, guidewires, aneurysm clips, suture clips, anti-embolic filters, etc. SMAs may be used for fabrication of devices to facilitate acute procedural applications and for fabrication of devices for chronic applications including implanted device.

Attempts have been made to tune properties of SMAs used in implantable medical devices to tailor the SMAs for their intended use. For example, attempts have been made to improve fatigue performance of SMAs used in implantable medical devices because the SMAs may suffer from fracture due to fatigue. To enhance fatigue performance of super elastic alloys, investigators have typically focused on enhancing the strength of the austenite parent phase of superelastic SMAs at least in part because austenite strengthening promotes reversible twinning and detwinning and reduces the propensity for irreversible plastic deformation caused by permanent dislocation slip. Accordingly, it is assumed to be more difficult to nucleate micro-cracks or plastic instabilities that could lead to fatigue fracture in production articles fabricated from a stronger superelastic SMA materials.

SUMMARY

The present disclosure describes, among other things, processes, structures and compositions that promote or inhibit in vivo formation of an intermediate R-phase between the austenite phase and the martensite phase. As indicted herein, promoting or inhibiting R-phase transition may be used to manipulate one more SMA property, such as fatigue performance, modulus and ductility. Treatments or material selections that separate or converge the R-Phase and the austenite phase may be used to manipulate the SMA properties.

The effect of promoting or inhibiting the in vivo transformation to the intermediate R-phase in SMAs, such as nitinol, has surprising effects. For example and as described herein, promotion of the R-phase, or convergence of the R-phase and the austenite phase, may result in increased ductility, decreased modulus and increased fatigue performance. Typically, increased ductility leads to decreased fatigue performance.

The present disclosure describes ways to promote or inhibit in vivo R-phase formation, or relative convergence or separation of the R-phase and the austenite phase, including altering the composition of the SMAs such as altering ratios of metals in the SMA, altering grain size, altering the shape or geometry of the SMA device or component, and heat treating the SMA device or component.

In some aspects described herein, a SMA device or component is treated to (a) promote R-phase to reduce modulus (and accommodate more strain) or inhibit R-phase to increase modulus, (b) alter geometry of the device or component to manipulate modulus, or both (a) and (b). As described herein, the presence of R-phase softens the nitinol components in a counterintuitive manner. For a nominally fixed length of beam, nitinol softens such that a slimmer beam is stiffer than a thicker beam of the same length, whereas conventional metals stiffen when the cross-sectional area is increased. Because the propensity for shear-induced R-phase softening is dependent on both (i) the presence/absence of R-Phase and (ii) beam geometry, judicious selection of heat-treatment to promote or inhibit in vivo R-Phase transformation coupled with geometric design can be used to tailor the apparent material modulus globally or locally in the device. Alternatively, for fixed design of device, the stiffness can be manipulated independently of geometry.

While the modulation pertains to the apparent modulus at the material levels, this readily translates into a number device-level implications. For purposes of example, device-level implications regarding a structural heart frame (for a prosthetic heart valve) comprising nitinol components are briefly discussed below. Promotion or inhibition of R-phase formation in vivo in nitinol components, or portions thereof, in a structural heart frame, may affect one or more of:

A. Impact to fatigue: More compliant elements may promote superior displacement-controlled fatigue, whereas more stiff elements may favor superior stress-controlled fatigue loading.
B. Device with modulated radial stiffness as it interfaces with native anatomy: Heart block has been attributed in part to the force exerted by the frame on the conduction system.
C. Device with reduced loading forces (assume 7° C. is typical=ice-bath): Could be coupled with chilled delivery catheter.
D. Device loading at room temperature vs. ice bath: Benefits include procedure simplification and perhaps less damage to the tissue leaflets.
E. Deploy with lower overall force: Benefits include procedural/deployment accuracy and ability to deliver a shorter valve which would otherwise deploy with a sudden burst when released from the capsule.
F. Decoupling of inflow from outflow: Benefits include better sealing and better effective orifice area throughout the cycle.
G. More uniform radial output across the deployed size range—for a discrete valve size: Benefits include reduced size offering to treat the target implant population, e.g., instead of n=5 sizes.

Promotion or inhibition of R-phase may:
A. Allow manipulation of the apparent elastic modulus.
B. Facilitate manipulation of device-level performance in a variety of different ways.
C. Promote or minimize the effect via thermomechanical processing.
D. Promote or minimize the effect when R-Phase is present via geometric design.

The phenomenon is pronounced under bend loading. Accordingly, devices employing SMA components that are subjected to bend loading may be manipulated to take advantage of this phenomenon. Such devices include, for example, structural heart valve frames, which are loaded predominantly in bending. However, it should be understood that this phenomenon may be exploited for any suitable device or component containing a SMA, particularly NiTi. Knowledge of this phenomenon and deliberate manipulation to take advantage of the phenomenon may allow better prediction of implantable medical device integrity and functional behavior during in vivo service.

In some aspects described herein, convergence or separation of the R-phase and the austenite phase of a SMA component of an implantable medical device are deliberately manipulated to affect characteristics of the components, such as one or more of fatigue performance, modulus, and ductility. In some embodiments, mechanical properties are tuned via a judicious selection of heat-treatment time, temperature, stress and strain, with particular emphasis and control of the cadence of incremental heat setting steps. In some embodiments, different zones and localities in a device or component may be selectively processed in a preferred sequence to deliberately erase or maintain various degrees of convergence and separation of the R-phase and austenite phase, which may be determined by endotherm peaks via differential scanning calorimetry (DSC). For example, one or more of the following properties of a SMA-containing device may be manipulated independently of geometric changes: delivery force; chronic-outward-force; crush resistance; and fatigue durability.

Different portions or zones within a device fabricated from a SMA, such as NiTi, may have divergent functional roles, and thus may preferably possess different mechanical properties in each portion or zone. Although geometric and dimensional aspects may be adjusted independently of explicit knowledge of prevailing transformation sequence, there are practical limitations on what can be achieved through geometric and dimensional aspects alone. Accordingly, it may be desirable to render local/zonal material properties within a monolithic structure of fixed geometry and of fixed dimensions via practical means, i.e., methods that can be readily reduced to practice for high-volume production.

Using the processes described herein, mechanical properties and fatigue durability of a SMA device or component may be preferentially varied (selectively tuned) in different regions within the same component to yield graded functional behavior and to optimize the overall component/device performance. In an analogous manner, the mechanical properties and fatigue durability of a SMA device can be 'normalized' such that the properties are consistent throughout.

Different zones and localities in a device may be selectively processed in a preferred sequence to deliberately erase or maintain various degrees of convergence and separation of the R-phase and austenite endotherm peaks as determined via DSC. This same processing also acts to elevate or reduce the upper and lower plateau stresses and the hysteresis energy therein to impact the operating stresses. Hence, via judicious and deliberate selection of the heat-treatment time, temperature, stress and strain, and with particular cadence of the incremental heat-setting steps the device may be selectively tuned to render a desired response.

While the methods described herein are applicable to SMAs containing near-equiatomic NiTi, they may also be applicable to slightly nickel rich NiTi SMAs and other SMA compositions such as Ni—Ti—X where X is a third element such as iron (Fe). The methods described herein may be applied to any suitable SMA device or component. Preferably, the device comprises a prosthetic heart valve frame. For example, the device may be a transcatheter valve (TCV) for minimally invasive heart valve repair, such as a TCV for mitral valve repair.

The methods described herein may enhance device performance to treat complex disease states demanding a variety of functional attributes in a single monolithic structure, may be amenable to volume production with no additional capital overhead or expenditure, may readily achieve graded functional and durability performance, may be used for devices employed in force-controlled and displacement-controlled environments.

In some aspects described herein, heat treatment of SMA devices or components, or portions thereof, is employed to either promote or inhibit in vivo R-phase formation. As described herein, R-phase may be promoted or inhibited by the choice of shape-setting temperature and time. Generally, higher temperatures inhibit and lower temperatures promote the R-phase.

As described herein, when SMA device or components (e.g., NiTi devices or components) are sheared, the presence of R-phase softens the component. This leads to an interesting counterintuitive consequence during beam bending, whereby the modulus increases with decreased cross-sectional area. Accordingly, stiffer components such as heart valve frames or components thereof may be achieved with smaller strut geometries. This may lead to a desirable reduction in device delivery profile without sacrificing performance. In addition, the modulus may be tailored at different portions of the device (e.g., strut of a heart valve frame) by varying strut depths, widths and lengths.

In some aspects described herein, a length to depth ratio of a SMA beam is chosen to promote or inhibit R-phase transformation, which may achieve either superior load-controlled or superior displacement-controlled fatigue performance. For SMA structural elements for which load-controlled beam geometry is desired, a length-to-depth ratio greater than about 8:1 may be used to minimize the shear forces in the beam, thereby inhibiting the R-phase transformation which is a shear-dominated phase transformation. For SMA structural elements for which displacement-controlled beam geometry is desired, a length-to-depth ratio less than about 8:1 may be used to minimize the shear forces in the beam, thereby promoting the R-phase transformation which may promote superior fatigue resistance under displacement-controlled conditions.

As described herein, a combination of the geometry and metallurgy of a SMA, such as nitinol, may promote a desirable stiffening of an entire implant, or sub-components within that implant. When SMA structural beams are loaded in bending, the minor shear component acts to stress-induce austenite to R-phase transformation and ensuing reorientation of the R-phase variant.

Scaffolds and supports fabricated from SMAs used in vascular applications, e.g., stents, frames, and endografts, are subjected to a combination of displacement-controlled and force-controlled loading. There are essentially two fundamental methods to improve fatigue durability depending on the predominant fatigue mode: (a) force-controlled—make the structure stiffer to resist the imposed loads; or (b) displacement-controlled—make the structure more compliant to better accommodate or distribute the imposed deformations. Because different parts of, for example a mitral TCV frame, may encounter different types of loads at different localities along it length or about its periphery, beam geometry in different zones can be tailored to achieve a desired performance within discrete zone/locality.

A combination of the geometry and metallurgy of the SMA structural component may promote a desirable stiffening of an entire implant, or sub-components within that implant. When SMA structural beams are loaded in bending, the minor shear component acts to stress-induce the austenite to R-phase transformation and ensuing reorientation of the R-phase variants. These events 'soften' the structural beams and do so in a very counterintuitive manner. For a fixed depth of structural beam (d), apparent flexural modulus (AFM) scales proportionally with length, i.e., AFM $\alpha$ L/d.

For structural elements requiring superior load-controlled beam geometry with a length-to-depth ratio typically greater than 8:1 is used to minimize the shear forces in the beam, thereby inhibiting the R-phase transformation which is a shear-dominated phase transformation.

In some aspects described herein, an SMA fixation element of an implantable medical device is treated or formed such that in vivo R-phase formation is inhibited, resulting in increased rigidity (modulus) of the fixation element.

As described herein, it has been discovered that a unique combination of the metallurgy and geometry of nitinol can promote a desirable stiffening of an entire implant, or sub-components within that implant. When nitinol beams are loaded in bending, the minor shear component acts to stress-induce the austenite to R-phase transformation and ensuing reorientation of the R-phase variants, these events 'soften' the beams and do so in a very counterintuitive manner. For a nominally fixed length (L) of beam having a fixed depth (d) and loaded in bending, R-phase transformation results in an apparent flexural modulus (AFM) that scales proportionally with length, i.e., apparent flexural modulus (AFM) is proportional to L/d. In contrast, for conventional metal beams the apparent flexural modulus (AFM) is independent of the cross-sectional area.

Implantable SMA medical devices often rely on fixation barbs to secure the implant in its desired anatomical position. Other devices may include appendage structures that project from the main superstructure, e.g., synch eyelets. Unlike the superstructure of the implant which may benefit from some amount of compliance for enhanced performance, fixation element appendages such as fixation barbs exhibit maximum anchoring ability for fixation and long-term fatigue durability due to their rigidity, i.e., their non-deformable and stiff properties. In an analogous manner, fixation elements such as synch eyelets benefit from greater rigidity. To date, stiffness of such SMA fixation elements has not been specifically engineered to inhibit the R-phase transformation in vivo, thereby promoting the desired stiffness through a combination of microstructural refinement and geometric design of the fixation element.

Based on the findings presented herein, an SMA fixation element, or portion thereof, may be manipulated by the appropriate selection of thermal aging time, temperature, and deformation to inhibit (i.e., reduce) the occurrence of the R-phase in vivo. Geometry and dimensions of the fixation elements may also be selected to inhibit R-phase occurrence and increase rigidity (modulus). For a fixed geometry and dimension of fixation element, thermal processing may be preferentially manipulated to confer enhanced stiffness.

In some aspects described herein, a SMA device or component having a desired stress plateau response is obtained by selecting an appropriate heat-treatment time, temperature, stress and strain, and cadence of incremental heat-setting steps. The treatment steps and cadence may be tailored to converge or separate R-phase and austenite phase endotherm peaks. For example, the heat treatment schedule may be selected to avoid obliteration of the R-phase exothermic peak (e.g., as determined via DSC). Via a judicious and deliberate selection of the heat-treatment time, temperature, stress and strain, and with particular cadence of the incremental heat-setting steps the device may be selectively tuned to render a desired R-phase response. Accordingly, via a judicious and deliberate selection of the heat-treatment time, temperature, stress and strain, and with particular cadence of the incremental heat-setting steps the device may be selectively tuned to render a desired stress plateau response.

For a given wrought (raw material) microstructure, the following thermomechanical events dictate the mechanical performance and fatigue durability of a device fabricated from thermomechanically processed NiTi: (i) time, (ii) temperature, (iii) strain, (iv) stress; and (v) sequence of incremental thermomechanical processing steps. Each of these variables individually and when combined, promote or inhibit certain phase transformations which subsequently modify the mechanical performance of nitinol components. Different zones and localities in a device may therefore be selectively processed in a preferred sequence to deliberately erase or maintain various degrees of convergence and separation of the R-phase and austenite endotherm peaks as determined via DSC.

Permutations of different time, temperature, strain, and stress are provided, these permutations along with the cadence of the steps facilitates a deliberate manipulation of stiffness and plateaus stress at local and global device levels.

In various aspects, a method to predict relative fatigue performance of SMAs is described. The method employs a benchmark for which both fatigue data and uniaxial stress-strain data are available without the need to conduct exhaustive fatigue testing on all materials of interest. The method uses uniaxial stress-strain data to predict fatigue performance. As discussed herein, materials that possess uniaxial stress-strain parameters associated with higher toughness or ductility, rather than higher strength, tend to exhibit superior fatigue performance. In embodiments, the uniaxial stress-strain data is obtained from a portion of the stress-strain curve beyond the martensite modulus in the work-hardening region (i.e., between the yield stress and ultimate tensile strength), this region has previously received little or no scrutiny.

Experiments described herein have identified that ductility or toughness is more important than strength in determining fatigue resistance of SMAs such as near equiatomic compositions of Ni—Ti (generally referred to herein as "nitinol"), particularly those that are compressed or loaded prior to or during use. Such compression or loading may act to promote an inhomogeneous distribution of plastic strain which may lead to undesirable local stress concentrations and large slip offsets at surfaces depending on the properties inferred by the prevailing microstructure. For example, compression or loading may introduce micro-cracks regardless of material strength. As described herein, the ability of a ductile and tough material to resist propagation of micro-cracks or resist inhomogeneous distribution of plastic strains during cyclic loading may be more relevant to fatigue performance than the ability of a stronger material to resist initiation of such micro-cracks and inhomogeneities, particularly when the superelastic shape memory material is pre-loaded prior to use, compressed or loaded during recapture post-deployment, or the like.

In embodiments described herein, an article comprises a structural scaffold formed from a SMA. The structural scaffold is expandable, is configured to be compressed prior to use, is capable of being recompressed during recapture post-deployment, or the like, and subsequently subjected to cyclic loading. The shape memory material structural scaffold is characterized as being ductile and has one or more of the following properties: (i) a critical stress for cross slip below a predetermined critical stress value; (ii) a yield stress below a predetermined yield stress value; (iii) a toughness greater than a predetermined toughness value, (iv) a strain at ultimate tensile strength (UTS) greater than a predetermined value, (v) a UTS to yield strength ratio greater than a predetermined ratio value, and (vi) a saturation stress below a predetermined saturation stress value. The shape memory material structural scaffold is fabricated from material that is processed to exhibit superior fatigue-resistance relative to a substantially similar article having a critical stress for cross slip above the predetermined critical stress value, a yield stress above the predetermined yield stress value, a toughness less than the predetermined toughness value, a strain at ultimate tensile strength (UTS) less than the predetermined strain at ultimate tensile strength (UTS) value, a UTS to yield strength ratio lower than the predetermined UTS to yield strength ratio value, or a saturation stress above the predetermined saturation stress value.

In embodiments described herein, a method for selecting a production SMA article predicted to have enhanced fatigue resistance includes subjecting a surrogate SMA article to thermal or thermo-mechanical shape-setting procedures to which the production SMA article will be or has been subjected to achieve a heat-treated surrogate SMA article. The surrogate SMA article is essentially the same as the production SMA article. The method further includes obtaining uniaxial stress-strain data of the heat-treated surrogate SMA article and selecting the production SMA article as an article predicted to have enhanced fatigue resistance if the uniaxial stress-strain data of the heat-treated surrogate SMA article indicates one or more of: (i) a critical stress for cross slip below a predetermined critical stress value; (ii) a yield stress below a predetermined yield stress value; (iii) a toughness greater than a predetermined toughness value, (iv) a strain at ultimate tensile strength (UTS) greater than a predetermined strain at ultimate tensile strength (UTS) value, (v) a UTS to yield strength ratio higher than a predetermined UTS to yield strength ratio value, and (vi) a saturation stress below a predetermined saturation stress value.

In various aspects described herein, performance characteristics of a SMA structural element of an implantable medical device are enhanced by heat-treating the structural element prior to shape setting the structural element. In some embodiments, the structural element is heated at a temperature between 580° C. and 620° C. for a time between 30 seconds and 500 minutes to produce a heat-treated structural element. The heat-treated structural element is then shape set.

In various aspects described herein, an implantable medical device comprises a structural scaffold comprising an SMA. The SMA comprises an overlap in transition temperature between the R-phase and the austenite phase. The transition temperatures may be determined by DSC.

A number of aspects and embodiments are described herein. It will be appreciated that these aspects and embodiments are not necessarily exclusive and that the aspects and embodiments, or portions thereof, may be combined.

Advantages of one or more of the various aspects and embodiments described herein will be readily apparent to those of skill in the art based on the following detailed description when read in conjunction with the accompanying drawings.

BRIEF DESCRIPTION OF THE DRAWINGS

FIG. 12 is a table summarizing shape setting conditions and resulting performance.

FIG. 17B is a plot of physical test data of a heart valve frame that is well matched by the dark blue data plot representing a simple FEA beam model with a substituted modulus of 40 GPa; the orange and light blue loops represent FEA beam models assuming substituted moduli of 70 GPa and 24 GPa respectively, by inspection, both fail to describe the physical test data.

FIG. 18A is a general schematic of a DMA instrument.

FIG. 18B is a typical clamping mechanism used for 3-Point Bending.

FIG. 21 is a schematic drawing of a (right) isosceles trapezoid cross-section showing key dimensions used to derive the 2nd moment of area. Laser-cutting stents and frames from a tube results in similar trapezoidal cross-sections where dimensions 'a' and 'b' are on the order 400 and 540 μm respectively and 'h' equivalent to the post-electropolished wall thickness is approximately 425 μm.

FIG. 22A is a plot of Theoretical Angular variation of elastic modulus for single crystal NiTi.

FIG. 22B is a plot of Angular variation of elastic modulus for single crystal Ta.

FIG. 40A is a plot of flexural moduli observed during loading at 37° C. and secant moduli observed during unloading at 0° C. for all wire diameters over a common span length of 3.553 mm.

FIG. 40B is a plot of flexural moduli observed during loading at 37° C. and secant moduli observed during unloading at 0° C. for all wire diameters over a common span length of 5.021 mm.

FIG. 40C is a plot of flexural moduli observed during loading at 37° C. and secant moduli observed during unloading at 0° C. for all wire diameters over a common span length of 9.994 mm.

FIG. 40D is a plot of flexural moduli observed during loading at 37° C. and secant moduli observed during unloading at 0° C. for all wire diameters over a common span length of 14.997 mm.

Figure 1A:
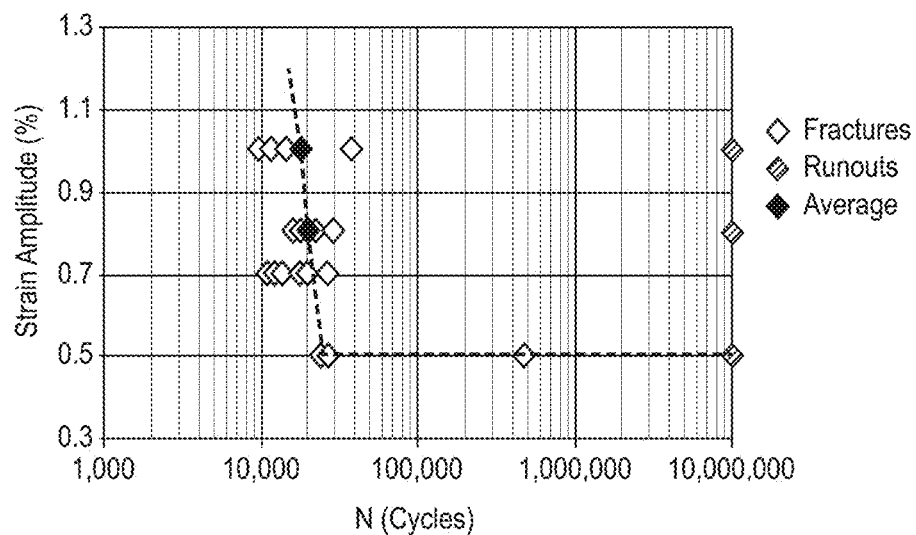
FIG. 1A is a plot showing alternating strain amplitude vs. cycles to failure for cell fatigue specimens extracted from full clinical quality heart valve frames subjected to conditioning comprising 2× deployments and reload cycles using production quality delivery systems and 1× tracking through a glass anatomical model.

The schematic drawings are not necessarily to scale.

DETAILED DESCRIPTION

In the following detailed description and examples, reference is made to the accompanying drawings that form a part hereof, and in which are shown by way of example results of several specific experiments that illustrate the effects of the compounds, compositions, and methods described herein. It is to be understood that other embodiments are contemplated and can be made without departing from the scope or spirit of the present disclosure. The following detailed description and examples, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, "SMA" or "shape memory alloy" refers to an alloy system that exhibits super-elastic or pseudo-elastic effects and shape memory effects.

As used herein, an article that is "substantially similar" to a SMA article having a particular stress-strain value (or set of values) above or below, respectively, a threshold is a SMA article of the same or substantially the same material, processing, shape and size that has a particular stress-strain value (or set of values) below or above, respectively, the threshold.

As used herein, "surface" refers to the area of contact between two different phases or states of matter.

As used herein, a surrogate SMA article that is "essentially the same" as a production SMA article is an article formed from the same material and processed in the same manner as the production shape memory alloy article. Preferably, the surrogate article is the same shape and size as the production article. However, in some circumstances the shape or size of the SMA production article is not conducive to uniaxial stress-strain testing. In such cases, the surrogate may be shaped or sized differently from the production article and may be in a shape and of a size suitable for uniaxial stress-strain analysis. In embodiments, the surrogate article is an article selected from a particular batch or lot of articles that will be used for production. In embodiments, the surrogate article is excised directly from a production article.

As used herein, a "production article" is an article used in the production of a finished article but is not necessarily the finished article and may be further processed before becoming or being incorporated into the finished article.

As used herein, "ultimate tensile stress" (UTS) is the maximum stress that a material can withstand prior to necking. The "ultimate tensile stress", may also be referred to interchangeably as the "ultimate tensile strength".

As used herein, "yield stress" is the transition between elastic and plastic behavior, the threshold for this transition is defined as the yield stress or yield strength which is also sometimes referred to as the flow stress. The "yield stress", also referred to interchangeably as the "yield strength" or "yield point" is defined as the stress at which the material begins to deform plastically. Once the yield stress has been reached, permanent deformation ensues as the specimen is further loaded. Since yielding occurs gradually for many alloys including SMAs such as nitinol, yielding is computed using a percentage offset, e.g. 0.02% or 0.2% constructions. The offset construction runs parallel to the linear portion of the stress-strain curve where stress is proportional to strain prior to yielding which in the case of nitinol is referred to as the martensite loading modulus. The point at which the offset construction line bisects the stress-strain curve defines the offset yield stress.

As used herein, "UTS/yield stress ratio" is the product of the maximum stress that a material can withstand prior to necking divided by the yield stress defining the transition between elastic and plastic behaviors.

As used herein, "toughness" (UT) is expressed as a post-superelastic or post-pseudoelastic toughness computed as:

$$U_T = \frac{\text{Yield Stress} + UTS}{2} \times \text{Strain at } UTS - \text{Strain at Yield}$$

where yield stress is computed as a offset yield e.g. 0.02% or 0.2% offset derived from a line construction running parallel to the net linear martensite loading modulus. The point at which the offset bisects the stress-strain curve defines the offset yield stress. The ultimate tensile stress (UTS) is the maximum stress that a material can withstand prior to necking. Strain at yield is the strain defining the transition between elastic and plastic behavior corresponding to the strain coincident with the corresponding yield stress. The strain at UTS is the strain defining the onset of necking corresponding to the strain coincident with the corresponding ultimate tensile stress (UTS).

As used herein, "strain at UTS" is the strain defining the onset of necking corresponding to that strain coincident with the corresponding ultimate tensile stress (UTS).

Figure 69A:
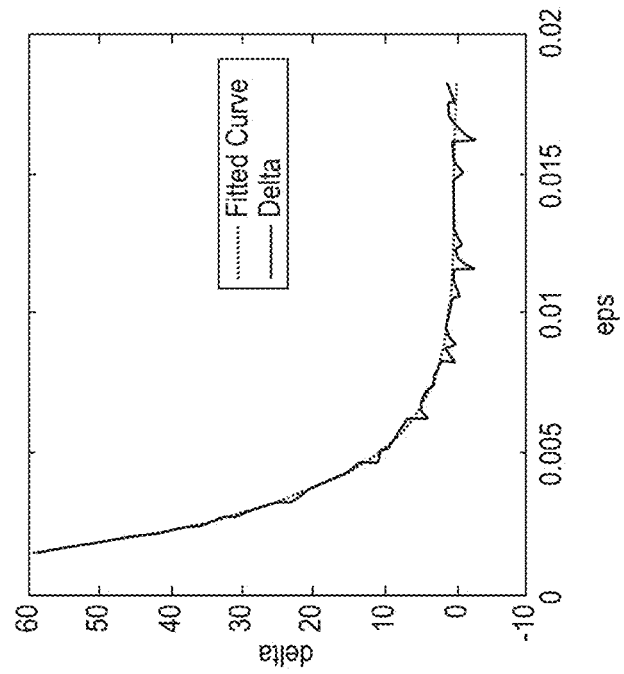
FIG. 69A and FIG. 69B are plots of a comparison of the Hollomon fit and data showing a difference (FIG. 69A), and of the delta plot with the fitted curve showing excellent agreement between data and fit (FIG. 69B).

As used herein, "critical stress for cross-slip" is the threshold stress marking the transition between Stages II and III plastic flow. The critical stress delineates that stress below which planar slip is prevalent and above which cross slip becomes dominant based on the rate of strain hardening. The critical stress can be derived using both numerical and graphical techniques. One method involves fitting the plastic portion of the stress strain curve using the Ludwigson equation and defining the critical strain as that location on the true plastic stress versus true strain curve where the value of delta function ($e^{K_2+n_2\varepsilon}$) is less than an arbitrary small value e.g. two percent (2%) of the value of the Holloman function ($k_1 \varepsilon^{n_1}$), or:

$$\frac{e^{K_2+n_2\varepsilon}}{K_1\varepsilon^n} = 0.02,$$

once the critical strain has been computed it is then possible to establish the corresponding critical stress defined by $\sigma_c = K_1\varepsilon^{n_1} + e^{K_2+n_2\varepsilon}$ [Eq. 1], refer to FIG. 69A of the Hollomon fit of experimental data clearly showing the difference (delta function), and a plot with the delta function fitted showing excellent agreement between data and fit.

As used herein, "Voce saturation stress" is derived from the $d\alpha/d\varepsilon$ vs. $\sigma_P$ plot of the Voce-fitted plastic data to yield a straight line, hence, by solving the Voce equation E. Voce, J. Inst. Metals, 74: 537 (1948)

$$\varepsilon = \frac{1}{n}\ln\left(\frac{\sigma_s - \sigma}{k}\right) \quad [\text{Eq. 2}]$$

for strain and substituting the derivative of the Voce equation, the resulting equation is of a line with slope (n) and intercept ($-n\sigma_s$) [Eq. 3].

$$\varepsilon = \frac{1}{n}\ln\left(\frac{\sigma_s - \sigma}{k}\right) \quad [\text{Eq. 2}]$$

$$\frac{d\sigma}{d\varepsilon} = -kne^{n\varepsilon} = n\sigma - n\sigma_s \quad [\text{Eq. 3}]$$

The Voce relation may be solved to give a value for the saturation stress $\sigma_s$. Saturation describes the condition where the strain-hardening rate is zero. At flow stress saturation, the rate of dislocation generation is balanced by an equivalent rate of dislocation annihilation, such that the rates of dislocation accumulation and recovery are balanced. At saturation, the net dislocation density neither increases nor decreases with additional deformation such that a constant flow stress condition is achieved.

The present disclosure describes, among other things, processes, structures and compositions that promote or inhibit in vivo formation of an intermediate R-phase between the austenite phase and the martensite phase. As indicted herein, promoting or inhibiting R-phase transition may be used to manipulate one more shape memory alloy (SMA) property, such as fatigue performance, modulus and ductility. For example and as described herein, promotion of the R-phase may result in increased ductility, decreased modulus and increased fatigue performance. Typically, increased ductility leads to decreased fatigue performance.

The present disclosure describes ways to promote or inhibit in vivo R-phase formation, including altering the composition of the SMAs such as altering ratios of metals in the SMA, altering grain size, altering the dimensions or geometry of the SMA device or component, and heat treating the SMA device or component.

The present disclosure also describes experiments illustrating that ductility and toughness are more important than strength in determining fatigue resistance of SMAs, particularly those that are compressed or loaded prior to or during use or during recaptured post-deployment. Such compression or loading may act to promote an inhomogeneous distribution of plastic strain which may lead to undesirable local stress concentrations and large slip offsets at surfaces or interfaces depending on the properties inferred by the prevailing microstructure. For example, compression or loading may introduce micro-cracks regardless of material strength. As described herein, the ability to resist propagation of initial cracks and the ability to resist inhomogeneous distribution of plastic strains may be more relevant to fatigue performance than the ability of a stronger material to resist initiation of such inhomogeneities or micro-cracks, particularly when the SMA is pre-loaded prior to use, or is subjected to post-deployment recapture, or the like.

A. Nitinol Processing-Property Relationship

Figure 1B:
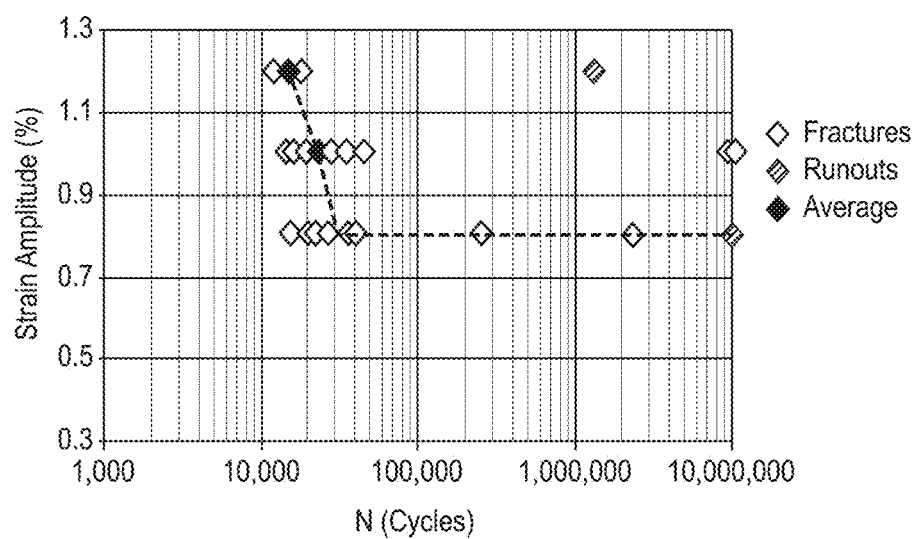
FIG. 1B is a plot showing alternating strain amplitude vs. cycles to failure for cell fatigue specimens extracted from full clinical quality heart valve frames subjected to conditioning in the same manner as the specimens in FIG. 1A.
Figure 2:
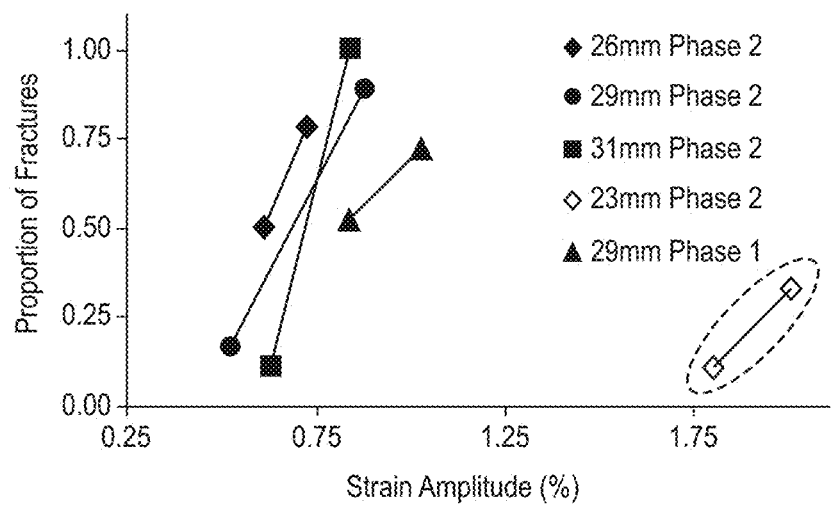
FIG. 2 is a plot of strain-life (displacement-controlled) fatigue data to 10M cycles run-out for cell test specimens extracted from heart valve frames, identity of specimen expressed by frame size and heat treatment phase. The 23 mm fatigue results are highlighted by the dashed ellipse; note the significant positive shift in fatigue response as compared to the other frame sizes.

Testing has revealed significant differences in material properties and device-level fatigue performance of heart valve frames of a common design fabricated using common tube material but with different heat treatments, refer to FIGS. 1A, 1B and 2.

Each end-point in FIG. 2 represents the mean fracture proportion observed from testing at a given strain amplitude or the average of slightly different strain amplitudes in cases where more than one strain amplitude level contributed to the establishment of an end point. The line between end points represents the predicted intermediate mean conditions. Specifically, the strain amplitude corresponding to a value of P=0.5 extrapolated from a given mean line is the predicted average test condition that would result in a fracture proportion of 50%, and is based on the assumption that the relationship between $\varepsilon_a$ vs. probability of fracture is linear in the regime of this testing.

To better understand the observed differences in fatigue performance shown in FIGS. 1A, 1B and 2, supplementary material-level tensile testing has been completed. This material testing revealed only subtle differences in the super-elastic properties of materials associated with different processing. Following these inconclusive results obtained from analysis of the super-elastic material response, a formal root cause analysis was executed to identify the source(s) of the observed discrepancies in device-level performance.

Figure 5:
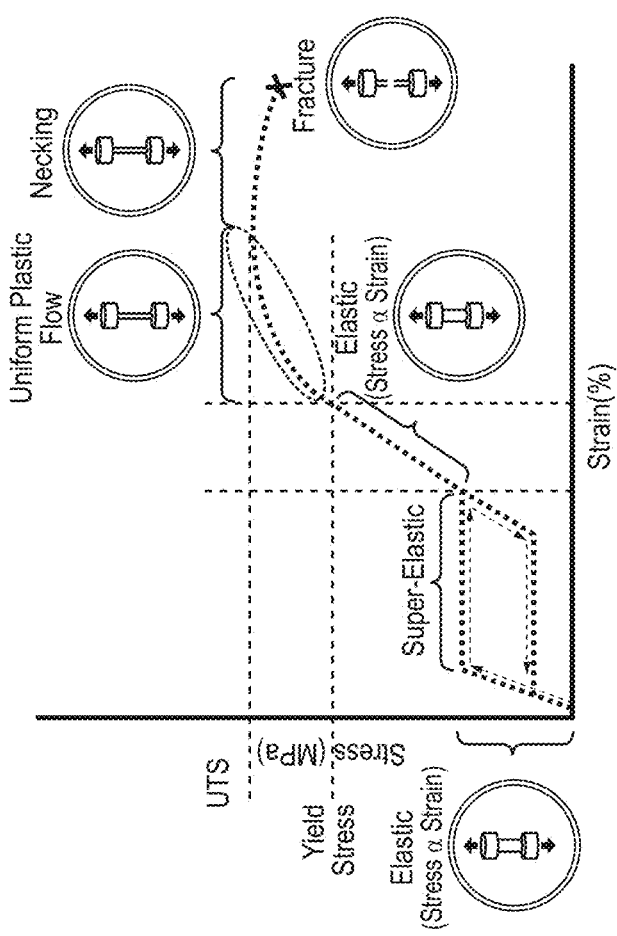
FIG. 5 is a schematic engineering stress-strain curve for superelastic Nitinol, the plot shows the superelastic 'flag' produced by loading to approx. 6% strain prior to unloading to zero and reloading to failure (fracture), loading path for the 1st cycle is delineated by the dashed arrows. The figure shows the main behaviors observed for a typical heat-treated Nitinol tensile specimen: elastic (austenite modulus), the superelastic flag (pseudoelasticity), elastic (martensite loading modulus), uniform plastic deformation (flow), necking and final fracture. The region delineated by the black dashed ellipse constitutes uniform plastic flow occurring between yield and UTS.

Classical physical metallurgy approaches were used to mathematically describe the plastic "flow" properties i.e., portion of the stress-strain curve beyond the yield point region (as delineated by the black dashed ellipse in FIG. 5) of the Phase 1 and Phase 2 materials and to compare the two sizes of tubes.

Figure 3:
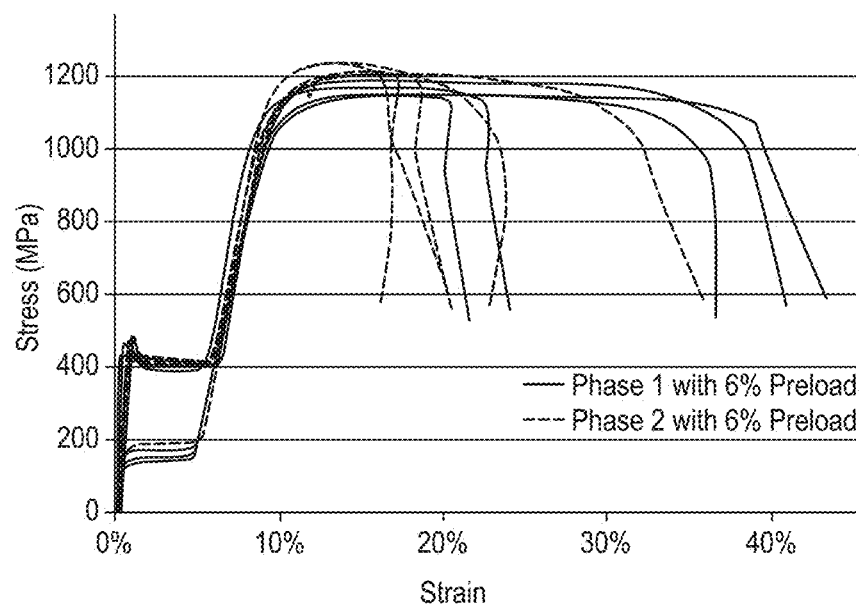
FIG. 3 is a plot of stress versus strain for surrogate tube specimens processed using 29 mm heart frame valves subjected to phase 1 and phase 2 heat-treatment processing subjected to a 6% preload on the first cycle prior to being pulled to failure. Test temperature was maintained at 37±2° C. with an engineering strain rate of $10^{-4} \cdot sec^{-1}$.

Stress vs. strain curves for surrogate tube specimens processed using 29 mm heart frame valves subjected to phase 1 and phase 2 heat-treatment processing subjected to a 6% preload on the first cycle prior to being pulled to failure are shown in FIG. 3. Test temperature was maintained at 37±2° C. with an engineering strain rate of $10^{-4} \cdot \text{sec}^{-1}$.

Different permutations of tube size and heat-treatment result in different flow stress and plastic flow behavior. Notably, log-log plots of true stress vs. true strain for nitinol tubes did not follow a simple power-law relationship: $\sigma = K\varepsilon^n$; instead, they exhibit dual-sloped plastic flow behavior irrespective of their heat-treated condition. To the best of our knowledge this behavior has not been previously reported in the published literature.

The rate of strain hardening has been explored using log $\Theta$ ($d\sigma_P/d\varepsilon_P$) versus log $\varepsilon_P$ plots and $\Theta$ ($d\sigma_P/d\varepsilon_P$) versus plastic stress $\sigma_P$ plots. Ludwigson and Voce equations (equations 1F and 2F) were found to accurately describe the observed plastic flow and strain-hardening behavior ($R^2 \approx 1$).

| | | |
|---|---|---|
| $\sigma = K_1\varepsilon^{n_1} + \exp(k_2 + n_2 \times \varepsilon)$ | Eq. 1F | Ludwigson |
| $\varepsilon = 1/n \ln((\sigma_s - \sigma)/k)$ | Eq. 2F | Voce |

Figure 6:
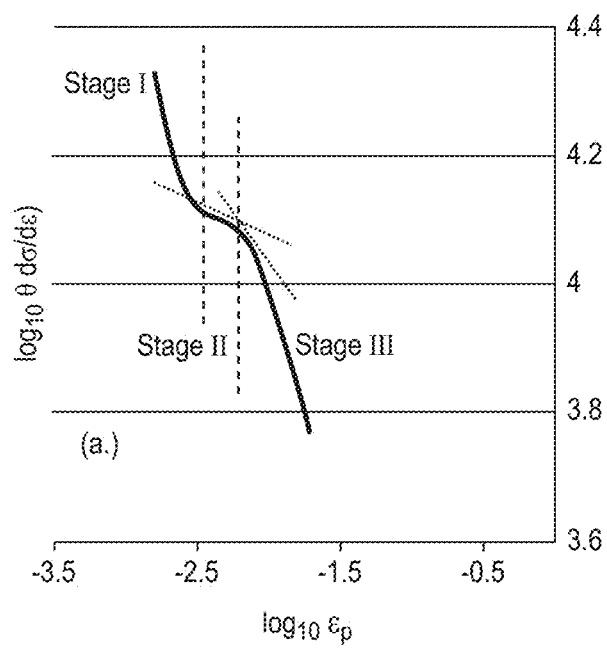
FIG. 6 is a representative plot of rate of strain hardening $\log \Theta(d\sigma_P/d\epsilon p)$ versus $\log \epsilon_P$ for a 6 mm tube in its as-drawn condition, i.e., no heat-set thermal processing.

Subsequently, three classically-defined flow regimes were identified, namely, Stages I, II and III. Critical stress and strain values marking the transition between Stages II and III flow have been derived, refer to FIG. 6 showing the delineation of the different stages on a representative plot of rate of strain hardening log $\Theta$ ($d\sigma_P/d\varepsilon_P$) versus log $\varepsilon_P$.

The critical stress and strain values represent the transition from a slip regime involving edge dislocations to one which allows dislocations to cross-slip onto adjacent planes via a screw-dislocation mechanism. In general, for most conventional engineering metals and alloys those factors that act to suppress cross-slip tend to increase the resistance to fatigue failure, i.e. increase fatigue strength. For nitinol tube specimens, a seemingly contrary trend has been observed, such that higher fatigue strength correlates with lower values of critical stress for cross-slip, and extended ductility and toughness. Despite the fact that the mechanisms involved at the Stage II to Stage III transition remain unknown for nitinol, the critical stress and strain marking the transition between Stage II and Stage III flow plus the parameters and constants derived from the Ludwigson and Voce curve fitting were successfully used to mathematically describe and discriminate the flow behavior of various materials.

Differences in flow properties resulting from differences in heat-treatment for a fixed tube size were attributed to impact of differences in the size and distribution of Ni-rich precipitates arising from competing nucleation and growth processes concurrent with the different thermal schedules.

Subsequently, a script was written in Matlab (version R2011b) to facilitate batch processing, this allowed the effects of different tube conditions/microstructures to be assessed (albeit indirectly) from the values of plastic flow parameters derived from uniaxial stress-strain data.

Figure 8:
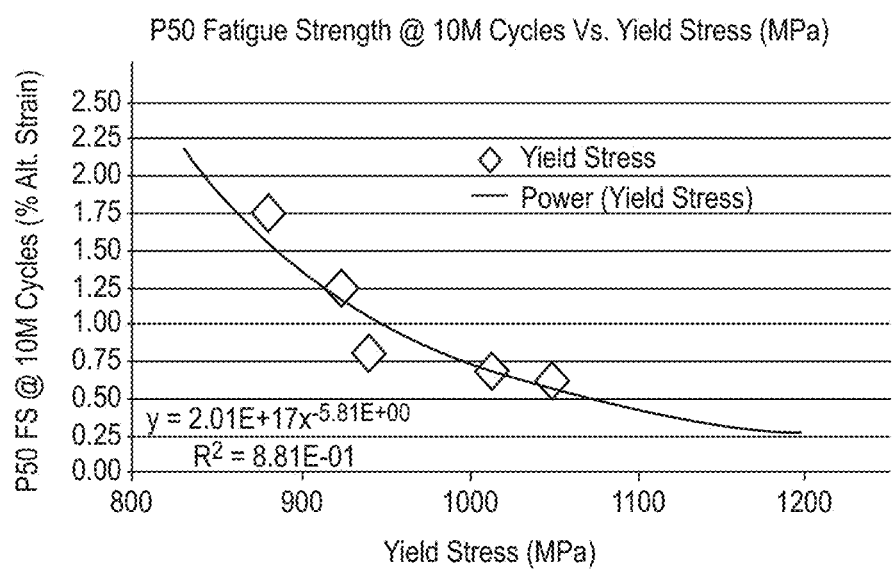
FIG. 8 is a plot of P50 fatigue strength vs. yield stress.
Figure 7:
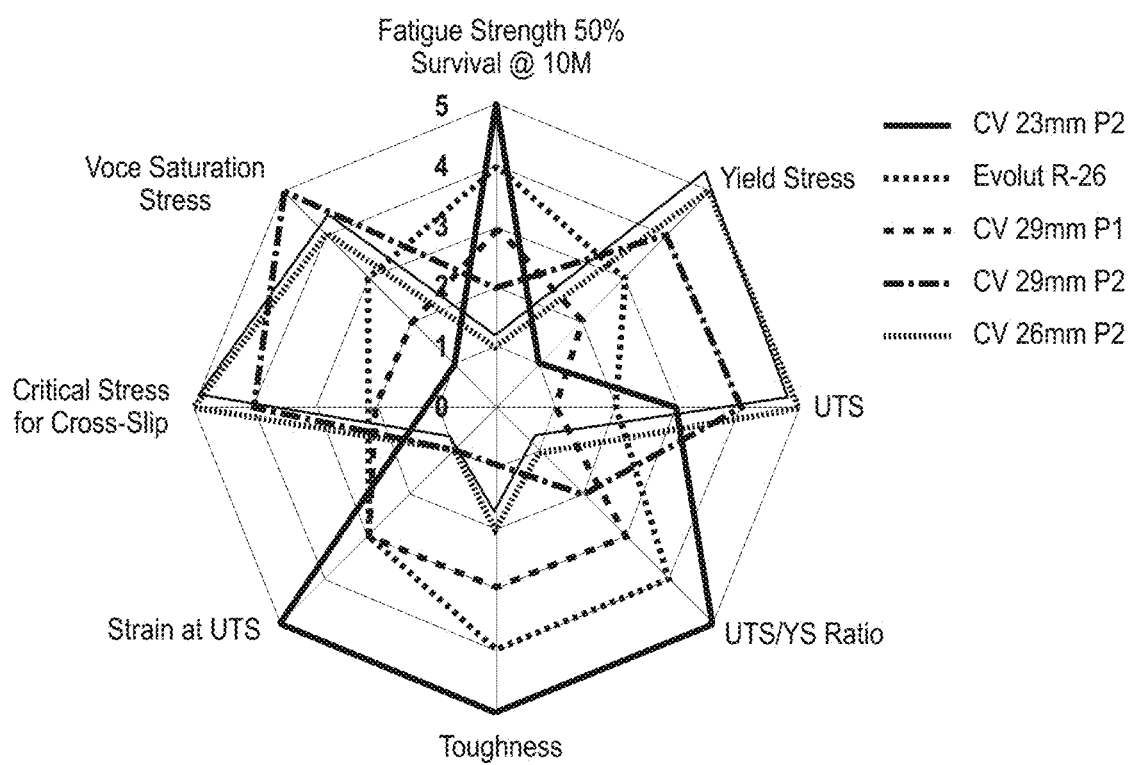
FIG. 7 is a plot of ascending ranked P50 fatigue strength expressed in terms of alternating strain amplitude for diamond fatigue test coupons versus their associated strength, toughness, and ductility values. Taking the highest fatigue performer CV 23 mm P2 as an example, superior fatigue strength coincides with the greatest ductility and lowest strength. Taking the lowest fatigue performer CV 26 mm P2 as a second example, inferior fatigue strength coincides with the lowest ductility and highest strength.

From the relationships shown in FIG. 7, selecting a single metric, in this case yield stress plotted versus P50 fatigue strength a clear relationship is observed. P50 fatigue strength vs. yield stress is shown in FIG. 8.

Figure 4A:
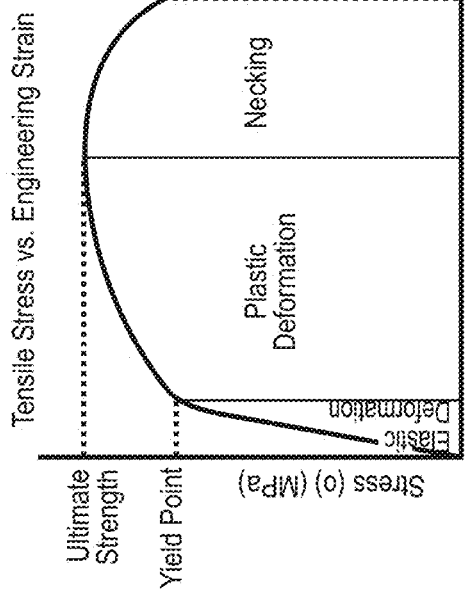
FIG. 4A is a schematic engineering stress-strain curve for a conventional alloy system showing typical monotonic tensile behavior: elastic, plastic deformation (flow), necking followed by final fracture.
Figure 4B:
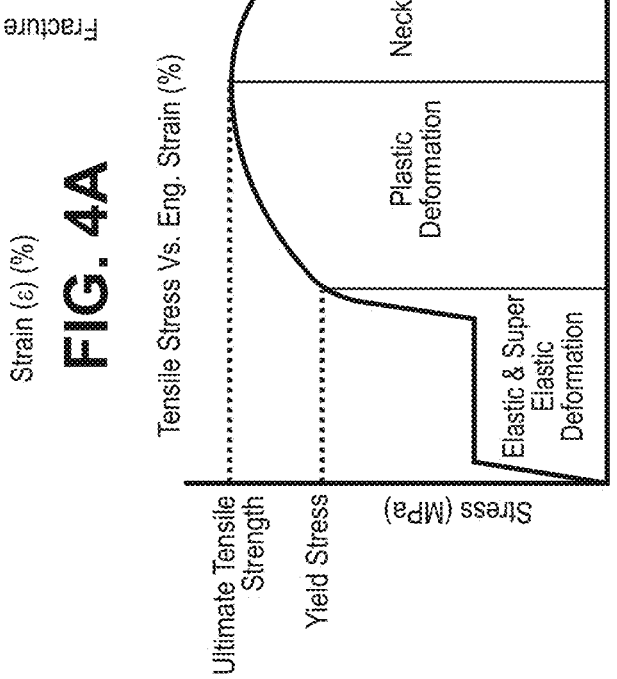
FIG. 4B is a schematic engineering stress-strain curve for heat-treated superelastic Nitinol showing typical monotonic tensile behavior: elastic, superelastic, plastic deformation (flow), necking followed by final fracture.

The models used to describe plastic flow as summarized herein were originally derived for and applied to the study of conventional elastic-plastic materials (FIG. 4A). For Nitinol (FIG. 4B), and especially monoclinic (B19') nitinol (region delineated by the black dashed outline in FIG. 5), dislocation slip is simultaneously active with phase transformation and twinning which may include elements of reorientation/twinning/detwinning and/or deformation twinning throughout the plastic deformation response. Simultaneous activity of post-yield transformation, twinning, detwinning, and dislocation slip will result in multiscale plasticity-transformation interactions; these interactions may explain why the relation between fatigue performance and plastic flow properties for NiTi is opposite of that observed for elastic-plastic metals.

Having established a clear understanding of the counterintuitive relationships between strength, toughness, ductility and fatigue performance, with knowledge of the correlation between thermomechanical processing, i.e., time-temperature-transformation relationships and mechanical properties, and knowledge of the relationship between mechanical properties and fatigue performance it is possible to manipulate fatigue performance via processing.

While it has been argued that the magnitude of plateau stresses dictates the operating stresses and ergo fatigue performance, data suggests that this relationship is not necessarily true, and instead, that a lower yield regardless of operating stresses will confer a superior fatigue performance. Accordingly, subjecting the nitinol component to elevated temperature even for a relatively short duration is capable of reducing the yield strength and improving the fatigue performance.

Capek and J. Kubásek [Influence of Short-Period Heat Treatment on Mechanical Properties of NiTi Wires, ICO-MAT (2012)] report from their study that the as-received wire possessed highest fatigue life versus other heat-treated conditions. Further they indicate that heat treatments at the temperatures up to 530° C. lead to decrease of fatigue life with increasing treatment temperature, whereas annealing at 600° C. caused to the increase of the fatigue life in comparison with the others annealed samples, but its fatigue life was still lower than fatigue life of the as-received sample. This conflict is attributed to the inability to introduce any preconditioning into the wire using rotary beam (spin) fatigue testing.

We attribute the gains in performances realized via lowered strength and elevated ductility to a crack blunting effects in a pre-crimped device-like coupons. Because a key value proposition of superelastic nitinol is the ability to reduce its profile for minimally invasive delivery, a majority of medical devices will be 'crimped' thereby introducing a population of prenucleated flaws—see below for further discussion.

The two components of equiatomic nitinol, nickel and titanium are both 1st row transition metals, all metals in this row from scandium through zinc are strong oxide formers, as a consequence commercial grades of wrought NiTi typically possess of relatively large metal oxide and oxy-carbide inclusions. Upon loading, micro-cracks develop at the interface between the inclusion and the metal matrix, in this manner; NiTi devices typically possess a population of pre-nucleated sub-critical flaws or short-cracks. Whether a short-crack remains dormant or grows into a larger more potent crack is dictated by the resistance of the metal matrix. An increased plasticity associated with extended ductility results in a plastic zone immediately in front of the crack tip. This is the zone within which substantial yielding has occurred as part of the crack nucleation process. The stress concentration leads to locally higher stresses and therefore the yield stress may be exceeded in the vicinity of the crack tip. The stress intensity may be defined as $K=\sigma\sqrt{c}$ [Eq. 1E], whereas fracture may be defined as $K>Kc$, where Kc is a critical stress intensity or fracture toughness, and is a material property and c and πc terms describe the size of the flaw. The stress at fracture may be expressed as $\sigma_f=Kc/\sqrt{(\pi c)}$ [Eq. 2E] which may be further defined in terms of a critical toughness parameter, Gc, which is given by $\sigma_f=\sqrt{(EGc/\pi c)}$ [Eq. 3E], E is the elastic modulus. The toughness can be thought of as the combination of surface energy and plastic work done at the crack tip and may be therefore expressed as $Gc=\gamma_{surface}+\gamma_{plastic}$ [Eq. 4E]. For most metals, the value of the surface energy term ranges between 0.5 and 2 J·m$^{-2}$, whereas the plastic work term is on the order of 100 J·m$^{-2}$. Therefore, the surface energy term can be neglected in most metal alloys and the plastic work term dictates the toughness. In summary, greater ductility results in a larger $\gamma_{plastic}$, which acts to retard crack growth via plastic crack tip blunting.

By inspection of $K=\sigma\sqrt{c}$ [Eq. 1E], stress is a primary driver of stress intensity, anything that can be done to reduce stress (or better distribute strain) may have an impact, the flaw size follows a sq. root importance, on this basis, although flaw size cannot and should not be ignored, it is not the primary lever to promote better fatigue performance assuming there is latitude to make geometric changes. Following that same logic, it has been proposed that, by reducing the plateau stresses, the stress developed in the device/component can be reduced for a given cyclic amplitude.

By inspection of $Gc=\gamma_{surface}+\gamma_{plastic}$ [Eq. 4E], greater ductility results in a larger $\gamma_{plastic}$, which acts to retard crack growth via plastic crack tip blunting, hence there may be latitude to promote superior fatigue performance by manipulating the time and temperature and sequence of thermomechanical processing.

B. Graded Functional Behavior & Selective Device Tuning Via Incremental Heat Setting Cadence For a given wrought (raw material) microstructure, the following thermomechanical events influence the mechanical performance and fatigue durability of a device fabricated from thermo-mechanically processed NiTi: (i) time, (ii) temperature, (iii) strain, (iv) stress, and sequence of incremental thermomechanical processing steps.

Each of these variables individually, and when combined, promote or inhibit certain phase transformations which subsequently modify the mechanical performance of nitinol components. Components fabricated from materials possessing greater convergence of the R-phase-to-Austenite-phase peak (typically determined by DSC) may result in (a) superior displacement-controlled fatigue performance; and (b) softer flexural modulus.

Different zones and localities in a device may therefore be selectively processed in a preferred sequence to deliberately erase or maintain various degrees of convergence and separation of the R-phase and austenite endotherm peaks as determined via DSC. It is apparent that although the reverse transformation on heating is more correctly associated with unloading of a device versus cooling, the incidence of the thermally driven so-called R'-phase and its proximity to austenite is indeed indicative of the mechanical response of the device during service. Therefore, this degree of separation can be correlated with mechanical response and process-parameters to devise thermomechanical processing schedules to yield a desired behavior at a particular locality or zone within a nitinol component.

Figure 9A:
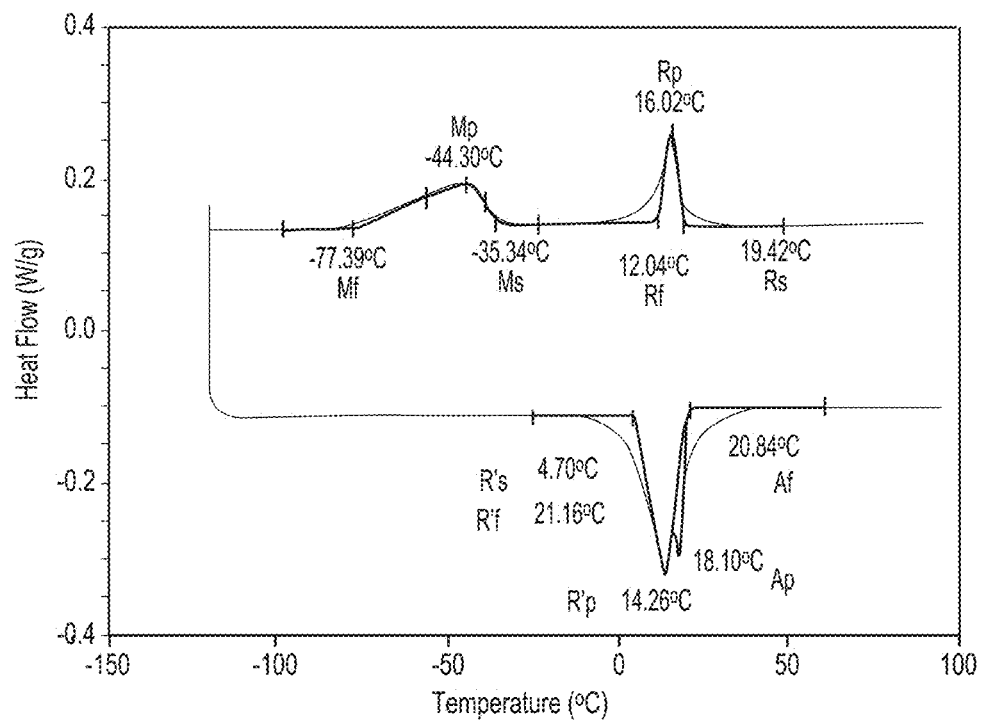
FIGS. 9A and 9B show DSC plots of nitinol illustrating greater convergence of R-phase and austenite phase (9A) and greater separation of R-phase and austenite phase (9B). Greater convergence=softer flexural modulus. Greater convergence=superior displacement-controlled fatigue. Greater separation=stiffer flexural modulus. Greater separation=superior force-controlled fatigue.
Figure 9B:
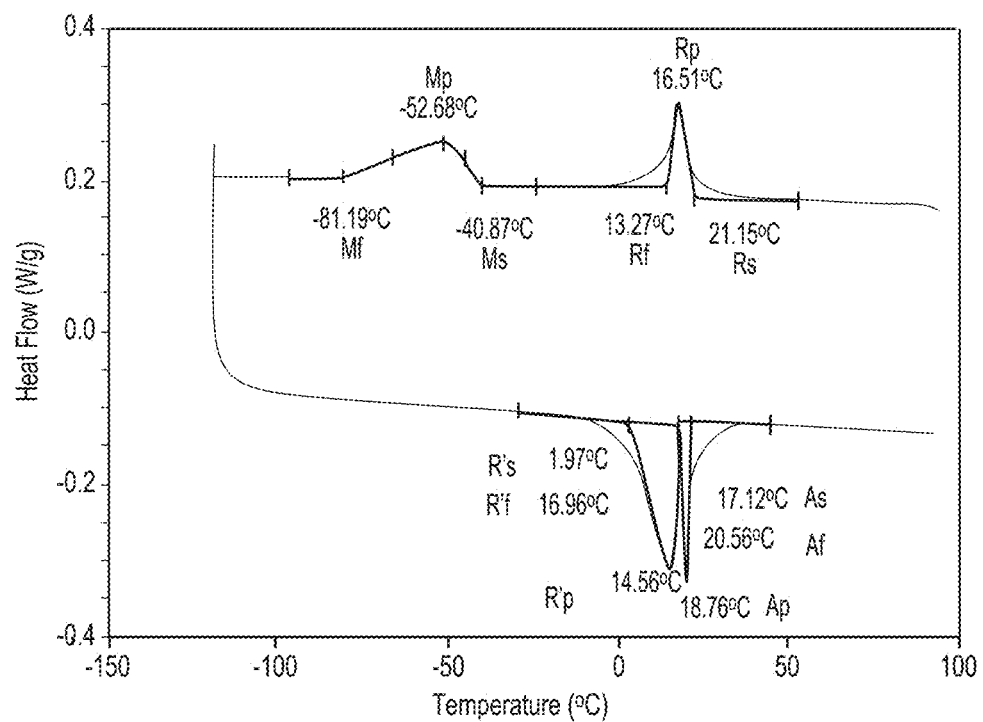
Figure 10:
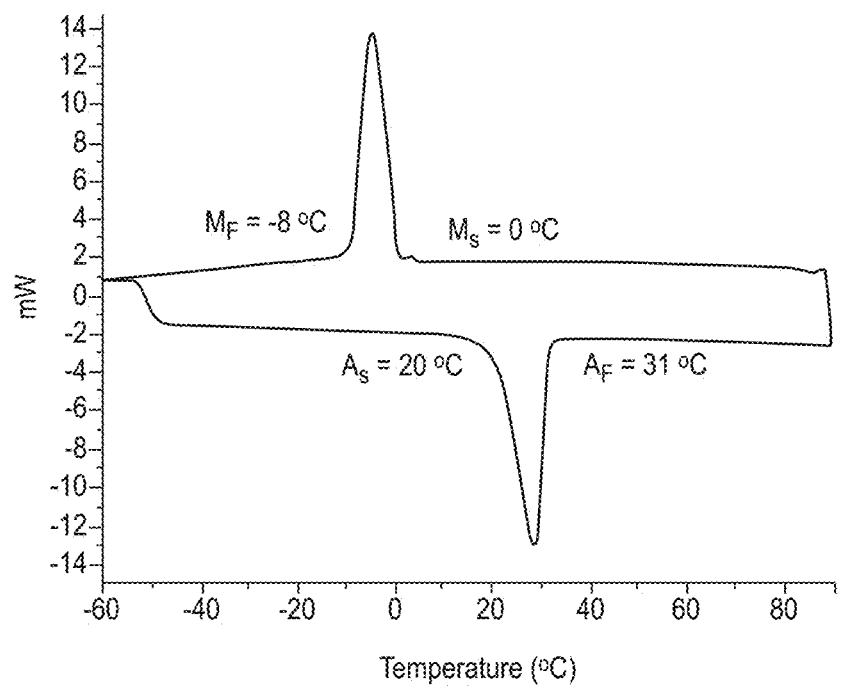
FIG. 10 is a thermogram of a fully solutionized NiTi SMA specimen, lacking an R-phase endotherm.

Because transformation commences and reaches completion at substantially different temperatures than those indicated by the standard "start" ($T_s$) and "finish" ($T_f$) temperature metrics derived using simple triangular-like tangent-line intercept constructions the true initiation and completion points of the transformations in the tails of the exo- and endo-therms are identified to ascertain cessation/concurrence of the R'-phase at a particular temperature. A combination of full and partial cycle DSC scans are used to deconvolute and reveal the individual Austensite and R'phase peaks. The partial cycle cooling the specimen to an intermediate temperature between the A→R and R→M transformations; i.e. $T \approx (R_f + M_s)/2$, and commencing the heating at that temperature to reveal the location of the R-phase on heating. In situations where the R'-phase and austenite endotherms overlap, this same approach is equally well capable of providing definition of the individual peaks. Via a judicious and deliberate selection of the heat-treatment time, temperature, stress and strain, and with particular cadence of the incremental heat-setting steps the device may be selectively tuned to render a desired response, refer to FIGS. 9A-B. The heat-treatment schedule may be preferentially selected to avoid obliteration of the R-phase exothermic peak, the thermogram shown in FIG. 10 shows a fully solutionized specimen processed at a temperature of 800° C.

Two primary embodiments are outlined to show the implementation of this technique to achieve divergent but desirable outcomes. The embodiments may be applied to either the whole component, or sub-sections (e.g. individual struts) of the component. For most complex nitinol components, there will be a combination where some features (e.g. struts) will retain the benefits of Embodiment 1 whereas others will retain Embodiment 2 benefits.

Embodiment 1

In this embodiment, the components or sub-components are first shape-set to their final geometry. Then, a final heat treatment or sequence of multiple heat treatments are applied while the (sub)component is in a relaxed condition (i.e. there are no applied deformations or loads to the target region). This zero-stress/strain heat treatment can be performed either entirely off-mandrel, or with a holding or supporting fixture that does not impart added stress or strain to the component while at heat treatment temperatures.

Embodiment 1a—Low Temperature Zero-Stress/Strain Tuning

Time=15s-600s
Temp=300° C.-525° C.
Stress/Strain=0

The low-temperature zero-stress/strain tuning promotes a separation of the R'-phase and Austenite-phase as evaluated via DSC. This separation results in a high flexural stiffness with relatively low upper and lower plateau stress values. In some embodiments, the separation of R'-phase and Austenite-phase as observed via DSC in the final (sub)component may be a complete separation. In other embodiment, the separation is less than complete to achieve desired properties.

The consequence of this microstructure may be expressed in terms of: (i) a low delivery force; (ii) low chronic-outward-force; (iii) high crush resistance; and (iv) a (sub) component with superior fatigue durability in displacement-dominated boundary conditions.

This combination of features may benefit applications requiring a mild chronic outward force, high crush resistance, yet good displacement-controlled fatigue durability. This material condition confers benefits for applications such as carotid artery stents which encounter acute crush forces resulting from external loading and trauma plus long-term displacement controlled cyclic loading associated with repetitive swallowing and pulsatile blood flow.

Embodiment 1b—High Temperature Zero-Stress/Strain Tuning

Time=15s-600s
Temp=450° C.-550° C.
Stress/Strain=0

The high-temperature zero-stress/strain tuning promotes a convergence of the R'-phase and Austenite-phase as evaluated via DSC. This convergence results in a low flexural stiffness with relatively high upper and lower plateau stress values.

The consequence of this microstructure is: (i) a low delivery force; (ii) low chronic-outward-force; (iii) low crush resistance; and (iv) a (sub)component with excellent fatigue durability in displacement-dominated boundary conditions.

This combination of features may benefit applications requiring mild chronic outward and radial resistive forces, with superior displacement-controlled durability. This material condition confers benefits for applications such as neurovascular stents in which the fine/small dimensioned struts encounter predominantly pulsatile displacements only with minimal additional biomechanical loading.

Embodiment 2

The nucleation energy barrier for the formation of nickel-rich precipitates in the Austenite is high, heterogeneous nucleation at grain boundaries is energetically favored during heat-treatment of assemblies and sub-assemblies in the relaxed condition, i.e., in the absence of an external applied load. Stress-assisted ageing (ageing under bias stress/strain) has been effective in producing homogeneously distributed precipitates in slightly Ni-rich near equiatomic Ni—Ti SMAs. Accordingly, in this embodiment, the components or sub-components encounter non-zero stress/strain during the final heat treatment step. This non-zero stress/strain heat treatment is accomplished by deforming the (sub)component using a mandrel, or other constraining fixture.

Embodiment 2a—Low Temperature Non-Zero-Stress/Strain Tuning

Time=15s-600s
Temp=300° C.-525° C.
Stress/Strain=Non-Zero

The low-temperature non-zero-stress/strain tuning promotes a separation of the R'-phase and Austenite-phase as evaluated via DSC. There is a preferential alignment of the lenticular shaped nickel-rich precipitates along the axis of applied stress/strain, the non-zero stress/strain also results in a relatively homogeneous distribution of those precipitates throughout the grains. The phase separation results in a high flexural stiffness. Furthermore, the aligned precipitates promote a localized increase in the energy required for phase transform, which results in an increased upper and lower plateau stress in the entire (sub)assembly or in the locality where the non-zero stresses/strains are preferentially applied.

The consequence of this microstructure is: (i) a relatively high deployment force; (ii) relatively high chronic-outward-force; (iii) high crush resistance; and (iv) a (sub)component with excellent fatigue durability in force-dominated boundary conditions.

This combination of features benefits applications where a high crush resistance and elevated outward force are required, examples of such applications includes iliac artery stents and venous stents. Other non-cardiovascular applications include orthopedic and spinal applications where force-controlled loads may predominate and where structural stiffnesses is desired.

Embodiment 2b—High Temperature Non-Zero-Stress/Strain Tuning

Time=15s-600s
Temp=450° C.-550° C.
Stress/Strain=Non-Zero

The high-temperature non-zero-stress/strain tuning promotes a convergence of the R'-phase and Austenite-phase as evaluated via DSC and preferentially aligns nickel-rich precipitates in the axis of applied stress/strain. The non-zero stress/strain also results in a relatively homogeneous distribution of those precipitates throughout the grains. The phase convergence promotes a low flexural stiffness. Furthermore, the aligned precipitates promote a localized increase in the energy required for phase transformation thereby raising the upper and lower plateau stresses.

The consequence of this microstructure is (i) very high delivery force, (ii) very high chronic-outward-force, (iii) low crush resistance, and (iv) a (sub)component with good fatigue durability in force-dominated boundary conditions. This combination of features may benefit applications in which force-control dominates although elements of displacement loading persist such as transcatheter mitral heart valves where a majority of the deformations are driven by blood pressure, yet secondary loading modes are driven by displacement-controlled motion of heart apparatus and physiological constraints.

Figure 11:
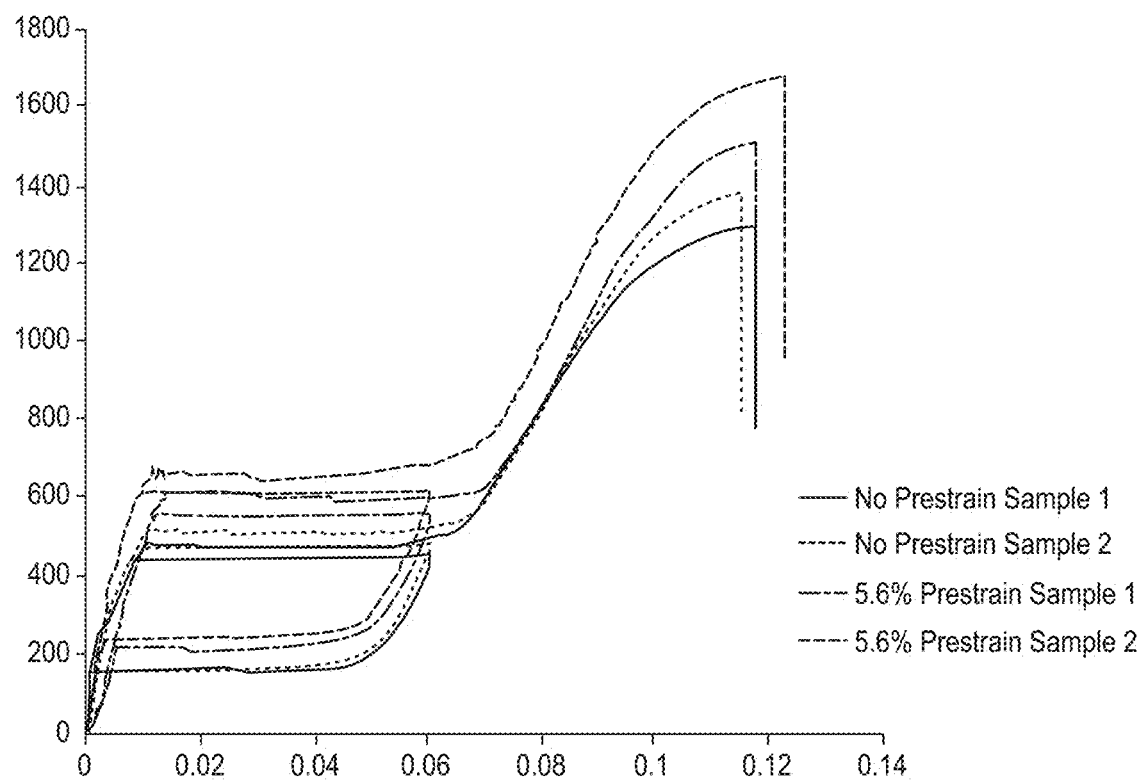
FIG. 11 is stress vs. Strain plots for NiTi SMA specimens with and without pre-load during heat treatment at a fixed time and temperature. Note, despite differences in upper plateau stresses, both the pre-strained and no-strained specimens possess the same Austenite peak, start and finish temperatures.

Stress strain curves of samples with no pre-strain and with 5.6% pre-strain during heat treatment at fixed time and temperature are shown in FIG. 11.

A summary of shape setting conditions and resulting performance is provided in the table in FIG. 12.

Additional Embodiments

In another embodiment, the separation or convergence of the R'-phase and Austenite-phase in the global device as evaluated via DSC is manipulated via selecting or achieving a grain size ranging one (1) micron to 35 microns. Subsequently using an analogue of the aforementioned scheme, this approach involves the introduction of nano-, micro- and meso-scale nickel-rich precipitates in a near-equiatomic NiTi alloy to achieve varying degrees of component and sub-component mechanical performance deliberately tailored for a variety of specific applications.

In another embodiment, the separation or convergence of the R'-phase and Austenite-phase in the global device as evaluated via DSC is manipulated via altering the ratio of nickel to titanium. Subsequently using an analogue of the aforementioned scheme, this approach is likewise used to achieve varying degrees of component and sub-component mechanical performance deliberately tailored for a variety of specific applications.

In another embodiment, an ageing process following solution treatment precedes the aforementioned scheme, the precursor processing (ageing process following solution treatment) yields a fine dispersion of coherent precipitates. Subsequently using an analogue of the aforementioned scheme, this approach is likewise used to achieve varying degrees of component and sub-component mechanical performance deliberately tailored for a variety of specific applications.

In another embodiment, the separation or convergence of the R'-phase and Austenite-phase in the global device as evaluated via DSC is manipulated via the penultimate cold work reduction steps employed during processing of the wrought source. For example, cold-drawn, seamless tube is subjected to a significant cold work reduction on the order of 35% prior to a final 'annealing' step. Subsequently using an analogue of the aforementioned scheme, this approach is likewise used to achieve varying degrees of component and sub-component mechanical performance deliberately tailored for a variety of specific applications.

In another embodiment, a preferred alloy composition is selected, e.g. near-equal atomic % nickel and titanium with addition of a third element for example iron (Fe). Subsequently using an analogue of the aforementioned scheme, this approach is likewise used to achieve varying degrees of component and sub-component mechanical performance deliberately tailored for a variety of specific applications.

In another embodiment, the crystallographic texture is manipulated, for example, for a cold-drawn tube, the relationship between the reduction in wall thickness and the reduction in diameter is given by the Q factor, $$Q \text{ factor} = \frac{t_{in} - t_{out}}{t_{in}} \bigg/ \frac{d_{in} - d_{out}}{d_{in}}$$

where $t_{in}$ is the wall thickness of the tube entering the die, $t_{out}$ is the wall thickness of the tube exiting the die, $d_{in}$ is the tube diameter entering the die, and $d_{out}$ is the tube diameter exiting the die. The draw ratio is selected to yield a preferred texture. Subsequently using an analogue of the aforementioned scheme, this approach is likewise used to achieve varying degrees of component and sub-component mechanical performance deliberately tailored for a variety of specific applications.

In yet another embodiment, the wrought NiTi SMA material is 'normalized' prior to any further secondary processing such as bending, cutting, forming, and prior to secondary thermomechanical shape-set processing via a higher temperature thermal-treatment comprising with or without mechanical constraint at a temperature 550-800° C. Subsequently, the global (sub) assembly or device, or different zones and localities in a device may therefore be selectively processed in a preferred sequence to deliberately erase or maintain various degrees of convergence and separation of the R-phase and austenite endotherm peaks as determined via DSC, and similarly, the plateaus stresses may be manipulated via heat-treatment with or without constraint to optimize other desirable properties.

In another embodiment, the wrought NiTi SMA material is thermally/thermo-mechanically processed prior to any further secondary processing such as bending, cutting, forming, and prior to secondary thermomechanical shape-set processing via a higher temperature thermal-treatment comprising with or without mechanical constraint at a temperature 300-350° C. Subsequently, the global (sub) assembly or device, or different zones and localities in a device may therefore be selectively processed in a preferred sequence to deliberately erase or maintain various degrees of convergence and separation of the R-phase and austenite endotherm peaks as determined via DSC; and similarly, the plateaus stresses may be manipulated via heat-treatment with or without constraint to optimize other desirable properties.

In another embodiment, the NiTi SMA (sub)component is thermally/thermo-mechanically processed via a thermomechanical shape-set processing via a higher temperature thermal-treatment comprising with or without mechanical constraint at a temperature 550-800° C. Subsequently, the global (sub) assembly or device, or different zones and localities in a device may therefore be selectively processed in a preferred sequence to deliberately erase or maintain various degrees of convergence and separation of the R-phase and austenite endotherm peaks as determined via DSC; and similarly, the plateaus stresses may be manipulated via heat-treatment with or without constraint to optimize other desirable properties.

Any combination/permutation of the aforementioned embodiments/methods may be used to in conjunction with a desired selection of the heat-treatment time, temperature, stress and strain, with particular cadence of the incremental heat-setting steps to produce a device that has been selectively tuned to render a desired response.

Figure 13:
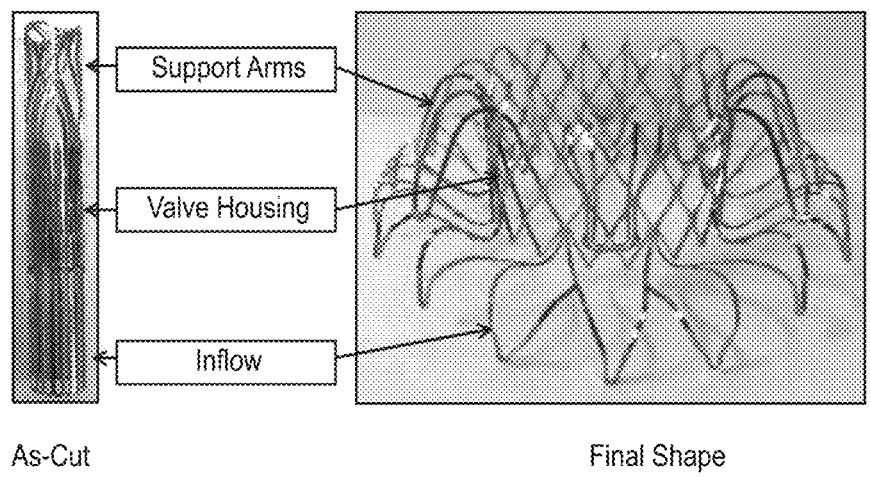
FIG. 13 shows images of Medtronic's Mitral Transcatheter Valve (TCV) in as-cut form and final shape.

An example that uses both Embodiment 1b and 2b in the same component is Medtronic's Mitral Transcatheter Valve (TCV). The component has three distinct regions: (i) a central cylindrical valve housing to which the valve is attached, (ii) an inflow region which represents the widest portion of the frame that resides in the atrium, and (iii) support arms which anchor the TCV in the target anatomy (see FIG. 13). The entire TCV system and implant environment results in predominantly force-controlled biomechanics. Consequently, a high temperature shape set is desired to promote fatigue durability. Furthermore, because of its heightened criticality to performance, it is desirable to have the greatest fatigue durability targeted in the support arms. Consequently, the Mitral TCV undergoes a deliberate 3-stage shape-setting operation whereby the valve housing and inflows are shaped first (thereby imparting Embodiment 1b) and the support arms shaped last (thereby imparting Embodiment 2b).

Phase 1—Valve Housing Shape Setting

Figure 14:
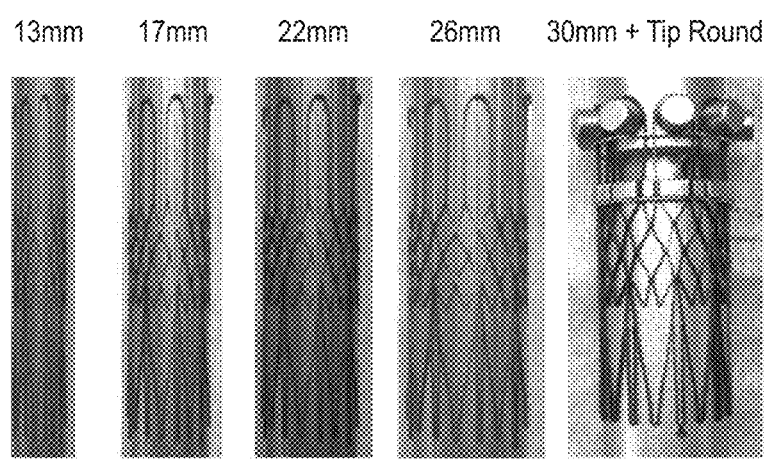
FIG. 14 shows images of a valve housing at various diameters during shape setting.

Beginning from a 10 mm as-cut tube, the valve housing is expanded radially to its 30 mm finished size via a 5-step shape setting process. During the shape setting operation, the valve housing experiences the events described by Embodiment 2b. However, once the valve housing reaches its final 30 mm shape, all subsequent shape setting steps in Phase 2 and 3 will confer the benefits of Embodiment 1b to the valve housing. FIG. 14 shows the valve housing at various diameters.

Phase 2—Inflow Shape Setting

Figure 15:
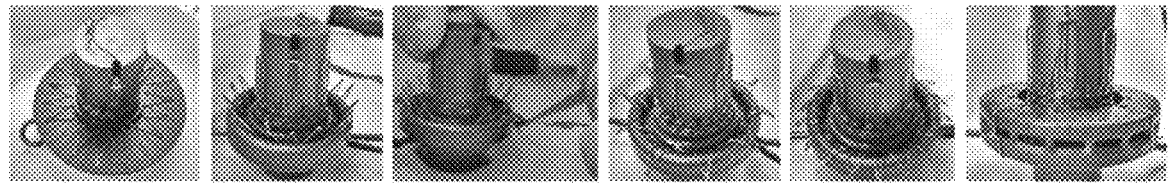
FIG. 15 shows images of an inflow region of a heart valve frame at various stages of shape setting.

The next subcomponent to be shape set is the inflow. During this shape setting step the valve housing (from the previous steps) is under a zero-stress/strain condition (Embodiment 1b) and the inflow is under non-zero-stress/strain conditions (Embodiment 2b). Again, subsequent shape setting step Phase 3 will confer the benefits of Embodiment 1b to both the valve housing and inflow. FIG. 15 shows the inflow region at various stages of shape setting.

Phase 3—Support Arm Shape Setting

Figure 16:
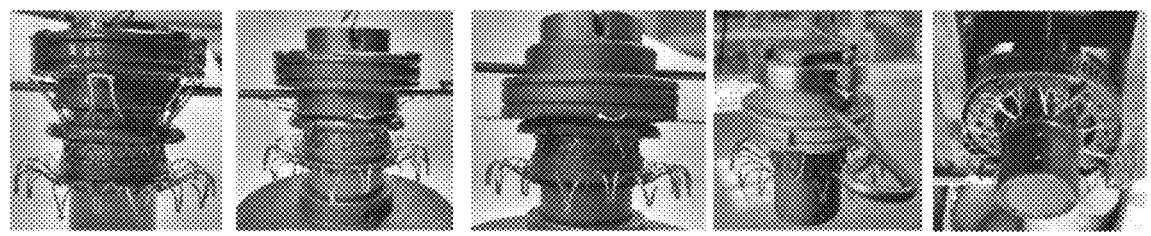
FIG. 16 shows images of support arms of a heart valve frame at various stages of shape setting.

The final shape setting step is performed with both the valve housing and inflow in states of zero-stress/strain (Embodiment 1b), and the support arms in a non-zero-stress/strain state (Embodiment 2b). This imparts maximum fatigue durability to the support arms while retaining good crush resistance and deliverability to the inflow and valve housing regions. FIG. 16 shows support arm shape setting at various stages.

C. Use of Bending to Derive Apparent Flexural Modulus—Stiffness of NiTi Beams

The influence of R-phase on mechanical behavior of nitinol was investigated. It was found that R-phase can be promoted or inhibited by the choice of shape-setting temperature and time. Generally, higher temperatures inhibit and lower temperatures promote the R-phase. It was also found that the presence of R-phase softens nitinol components when the components are sheared. This leads to an interesting counterintuitive consequence during beam bending. Unlike conventional metals that stiffen when the cross-sectional area is increased, nitinol (in the presence of R-phase) softens when the cross-sectional area is increased.

Based on these findings stiffer frames can be can be achieved with smaller strut geometries. Accordingly, devices having beneficially lower profiles may be made without compromising stiffness. In addition, stiffness throughout an individual device, such as a heart valve frame, may be tailored by varying strut depths, widths and lengths.

Finite element analysis (FEA) is used extensively in the design and development of NiTi heart valve frames. For heart valve frames cut from tubes, the use of standard user material subroutine (UMAT) inputs acquired from tensile testing of surrogate tube test specimens typically yields FEA results which provide an acceptable description (within 10%) of the force displacement relationship observed for a physical test. In those cases where FEA has proven incapable, manipulation of the austenite modulus values has facilitated closer agreement between the FEA and physical test data. As a result of these observations plus awareness of process-dependent microstructural differences between surrogate test specimens and fully processed devices, alternatives to the standard tensile test have been explored using struts cut from fully processed frames. Since the primary loading mode imposed on heart valve frames during service is bending, and because conventional tensile gripping techniques may cause premature transformation in small strut specimens, a three-point bending method has been developed using a dynamic mechanical analyzer (DMA).

Knowledge of physiological loading (Environment) is derived using CT and/or other imaging techniques. Physiological loading is typically expressed in terms of linear displacement whereas the material response (Function) is measured in terms of resultant stresses and strains. FEA facilitates the translations of imposed in vivo deformations from displacements (measured in mm or fractions of mm) into stresses and strains expressed in terms of N/mm2 and mm/mm respectively. Further, FEA facilitates the evaluation of complex geometries subjected to multiaxial loading, which may be important for medical devices. Because the stress-strain response of NiTi is non-linear, in many cases reliable FEA is an important tool for understanding the complex dynamics and is consequently key for the development of superelastic NiTi devices such as heart valve frames. Once the stresses and strains arising in the frames due to the in vivo loading have been estimated, comparison of the stresses and strains with respect to the cyclic capability of the material (fatigue life) facilitates a prediction of reliability, that is, whether the device will survive and remain functional for the required duration e.g., 400M or 600M cycles equivalent to implantation survival for 10 or 15 years (Durability).

For reasons of practicality, the mechanical properties of the NiTi from which transcatheter valve frames (TCV) are fabricated are typically derived using larger surrogate test specimens loaded in a standard tensile test. Subsequently, the mechanical property data acquired from these larger specimens is fed into FEA. The validity of an FEA model is typically established by comparing the output of the simulation to physical test data, i.e., the question is posed "does the FEA provide an acceptable description of reality?" In most cases the FEA is found to reasonably mimic a physical test, e.g., the force displacement response during a radial crimp test. However, on occasion FEA may be incapable of reproducing experimental results thereby casting wider doubt on the accuracy and reliability of its predictions. In those cases, it has been found that a drastic reduction of the austenite modulus is necessary to achieve acceptable agreement between the FEA and physical test data.

Figure 17A:
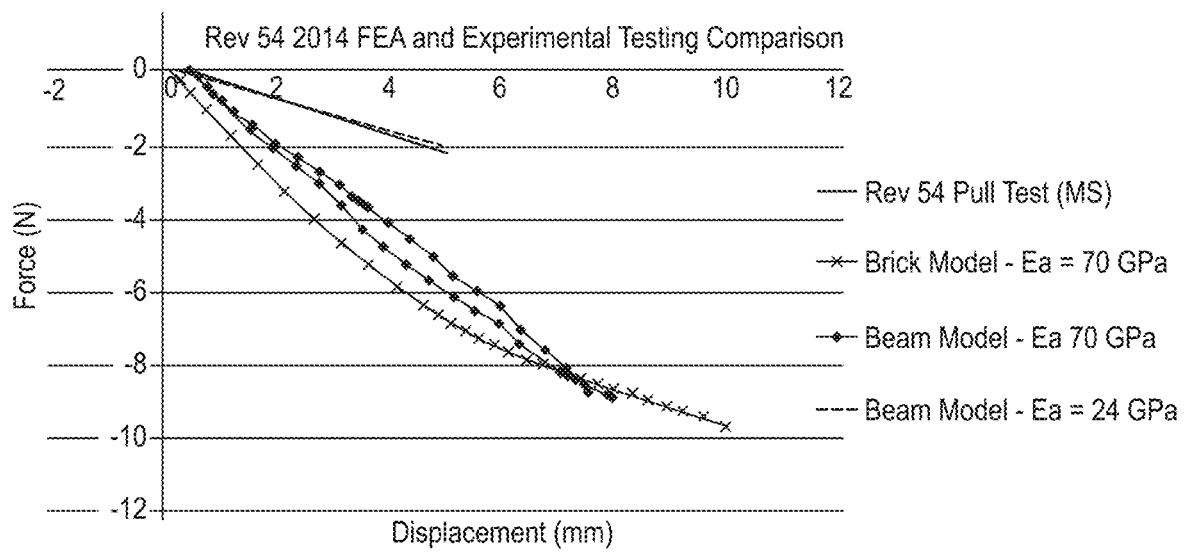
FIG. 17A is a plot of physical test data for a heart valve frame that is well matched by the overlying red line representing a simple FEA beam model with a substituted modulus of 24 GPa; the two blue lines representing FEA beam model (dark blue) and FEA brick model (light blue) both assuming a modulus of 70 GPa fail to describe the physical test data.

Several cases where FEA models have been successfully manipulated to show good correlation with physical data via substitution of a much lower 'artificial' or 'apparent' austenite modulus are shown in FIGS. 17A-B. In each case the initial modulus (≈70 GPa) was derived from an 8" length of tube which had been heat-treated in a manner commensurate with the thermomechanical processing of the heart valve frame of interest In a majority of cases FEA provides acceptable agreement and no adjustment of Ea is required.

As a result of the observed discrepancies (FIG. 17A and FIG. 17B) plus awareness of process-dependent microstructural differences between surrogate tube specimens and those in the fully processed device, alternatives to the standard tensile test with applicability to discrete struts cut from the fully-processed devices have been sought. Because the primary loading mode imposed on heart valve frames during service is bending, and as a means of avoiding spurious results associated with premature transformations caused by excessive clamping forces at the grips etc., a simple 3-Point flexural test has been developed using DMA. A combination of dynamic and quasi-static mode DMA testing has been completed. A majority of the testing completed to-date employs 'quasi-static' testing, in such cases, the loading is applied monotonically, subsequently, stiffness of the struts ($\delta F/\delta d$) is deduced from raw force versus displacement data, this is substituted into the standard beam equation which is then solved to give the apparent modulus.

The DMA instrument measures stiffness and 'damping', these are reported as moduli and tan delta. Two moduli are reported (i.) an in-phase component, the storage modulus (E'), and (ii.), an out of phase component, the loss modulus, (E"). The storage modulus, E', is the measure of the specimen's elastic behavior and is analogous to but not directly equivalent to Young's modulus. The loss modulus, E", is the measure of energy dissipated as heat and acoustic energy etc. and describes the specimens' viscous behavior. The ratio of the loss modulus to the storage modulus is the tangent of the phase angle referred to as the tan delta ($\delta$) and is often referred to as damping since it is a measure of the material's ability to store/dissipate energy. Energy dissipation varies with the state of the material, its temperature, and with the frequency of the test. The DMA instrument can also be used to report raw force and displacement data which can be exported and used to compute modulus independently of the DMA software.

With reference to FIG. 18A, the DMA instrument comprises a displacement sensor in the form of a linear variable differential transformer (LVDT), which measures a change in voltage as a result of the instrument probe moving through a magnetic core, a temperature control system or furnace, a drive motor (a linear motor for probe loading which applies the force), a drive shaft support and guidance system to act as a guide for the force from the motor to the specimen, and sample clamps in order to hold the specimen being tested. The typical clamping mechanism used for 3-point bend testing is shown in FIG. 18B.

The remainder of this section is separated into seven (7) sub-sections:

1.0 Baseline Axial and Three-Point Bend Testing of cpTa Wires and Beams
2.0 Three-Point Bend Testing of NiTi Beams
3.0 Three-Point Bend Testing of NiTi Beams at Elevated Temperatures
4.0 Literature Review & Re-Analysis of Published Data
5.0 NiTi Round Wire Testing
6.0 Three-Point Bend Testing of Heat-Treated 0.764 mm Ø Round Wire Specimens
7.0 Mitral TCV Inflow Stiffness Testing
1.0 Baseline Axial and Three-Point Bend Testing of cpTa Wires and Beams
1.1 Introduction A baseline methodology and DMA 3-point bend test capability was established using commercial pure tantalum (cpTa) test specimens. Annealed Ta exhibits close to perfectly ideal elastic-plastic behavior which persists in well-defined linear elastic proportional behavior in the worked condition. Unlike NiTi shape memory alloys (Nitinol), Ta exhibits conventional alloy behavior, i.e., no stress-induced transformations and therefore no appreciable hystoelasticity is observed during thermal or mechanical loading and unloading. It is recognized that all ductile metals/alloys exhibit some viscoelastic behavior.

1.2a. Test Method 1A. (DMA)

Testing was completed via both 3-point bend and axial tensile testing in displacement-control mode using a peak-to-peak displacement of 50 µm. Testing was completed using a TA Q800 DMA at a load-unload frequency of 1 Hz, all testing was completed at 25° C. The exact chemical composition of the cpTa specimens is not known, specimen selection was approached from a utilitarian perspective, i.e., both types of specimens were on-hand, clearly labelled, and available at the time of testing. The round wire specimens were 0.120 mm diameter, the beam specimens were cut from shim sheet material using a precision guillotine, the beams were 0.245 mm height (also referred to as depth in some publications) with a breadth of 4.39 mm. The span length was 14.997 mm for the rectangular specimens; the average gauge length of the round wire specimen was 14.3 mm. Tests were run for a duration of 60 seconds, values of dynamic storage modulus (E') and complex modulus E* (the sum of the storage and loss modulus) were reported for the 30th cycle, i.e., at the midpoint of the test.

1.3a. Results—Method 1A. (DMA)

TABLE 1

Flexural storage modulus (E') and complex modulus values (E*) equivalent to the sum of the storage (E') plus loss modulus (E") for n = 5 replicates (rectangular beam and round wire). Note the relatively low scatter and close agreement between the two means. Round wire specimens were tested in axial tension; rectangular beams were tested in 3-point bend.

| | Flexural Modulus (GPa) | | | |
| | Rectangular Beam | | Round Wire | |
| Replicate | E' | E* = E' + E" | E' | E* = E' + E" |
| --- | --- | --- | --- | --- |
| 1 | 178.11 | 178.37 | 177.11 | 179.92 |
| 2 | 178.16 | 178.46 | 175.04 | 177.22 |
| 3 | 178.10 | 178.48 | 173.38 | 175.92 |
| 4 | 178.16 | 178.48 | 173.95 | 176.38 |

TABLE 1-continued

Flexural storage modulus (E') and complex modulus values (E*) equivalent to the sum of the storage (E') plus loss modulus (E") for n = 5 replicates (rectangular beam and round wire). Note the relatively low scatter and close agreement between the two means. Round wire specimens were tested in axial tension; rectangular beams were tested in 3-point bend.

| | Flexural Modulus (GPa) | | | |
|---|---|---|---|---|
| | Rectangular Beam | | Round Wire | |
| Replicate | E' | E* = E' + E" | E' | E* = E' + E" |
| 5 | 178.13 | 178.48 | 173.58 | 175.82 |
| Mean | 178.32 | 178.45 | 174.61 | 177.05 |

Figure 19:
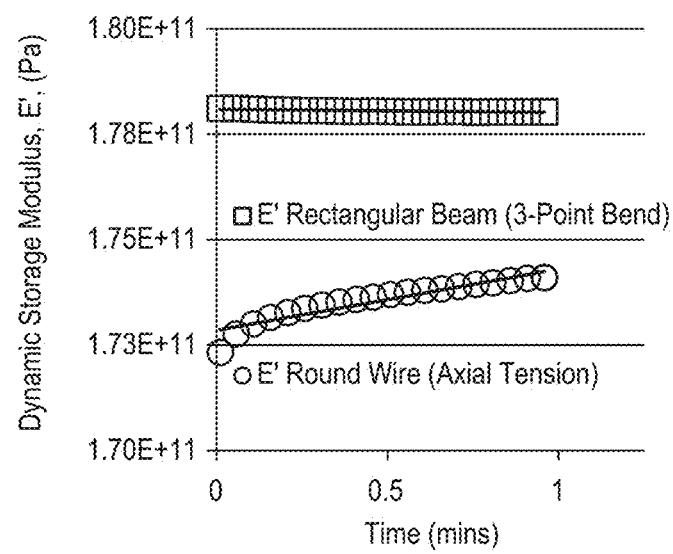
FIG. 19 is a plot showing dynamic storage modulus (E') of a representative cpTa wire and sheet specimen. Testing was completed using a TA Q800 DMA instrument in displacement control mode at a load/unload rate of 1 Hz and a peak-to-peak deflection of 50 μm. Round wire specimens were tested in axial tension; rectangular beams were tested in 3-point bend.

Preliminary testing of cpTa beams (n=5 rectangular specimens and n=5 round wires) at room temperature revealed flexural storage moduli of 178 GPa and 174 GPa respectively representing excellent agreement with published values for Young's modulus (179-186 GPa) refer to FIG. 19 and Table 1.

1.2b. Test Method 1B (Instron E3000)

Confirmation testing of n=5 beam specimens cut from the same Ta sheet as those specimens tested via Method 1A was completed in 3-point bending using the DMA software module on an Instron E3000. In accordance with the prior testing using the TA Q800 instrument, all testing was completed at 1 Hz. Test was completed at room temperature (22° C.) using a peak-to-peak displacement amplitude of 50 μm. An initial preload equivalent to a strain of 0.3% was applied to maintain contact during cycling. The Instron E3000 possesses a stroke accuracy of around ±2 μm over the 50 μm peak-to-peak displacement range.

1.3b. Results—Method 1B. (Instron E3000)

TABLE 2

Complex modulus values (E*) equivalent to the sum of the storage plus loss modulus (E") plus elastic modulus values computed from stress-strain data during loading and unloading for n = 5 rectangular beam replicates tested in 3-point bend.

| | Complex Modulus, $E^* = \sqrt{E'^2 + E''^2}$ (GPa) | Elastic Modulus $E = \sigma/\varepsilon$ (GPa) | |
|---|---|---|---|
| Specimen | (Loading + Unloading)/2 | Loading | Unloading |
| 1 | 188.15 | 195.76 | 193.35 |
| 2 | 187.71 | 191.28 | 188.52 |
| 3 | 165.98 | 170.22 | 169.31 |
| 4 | 173.10 | 178.13 | 176.13 |
| 5 | 160.66 | 162.91 | 161.31 |
| Mean | 175.12 | 179.66 | 177.72 |

1.4 Discussion Test Methods 1A & 1B

The Young's modulus for loading and unloading cited for Method B were computed from stress-strain data. Although greater variability amongst the test replicates is observed for Method B, the mean values for complex modulus (E*) remain consistent with those computed using the TA Q800 system. A possible source of error in the Method B tests arises from measurement of specimen dimensions associated with slight irregularities in specimen shape as cut using the "precision" guillotine. Regardless of absolute error, by inspection (Tables 1 and 2), the overall the moduli computed using the Instron E3000 are in good agreement with those computed using the TA Q800 instrument and both datasets show good agreement with values published by Cabot Supermetals, Product Information Mechanical Properties of Tantalum and Alloys; and Defense Documentation Center—Unclassified Report #426344: http://www.dtic.mil/dtic/tr/fulltext/u2/426344.pdf.

1.5 Conclusion Test Methods 1A & 1B

DMA provides a useful technique for determination of the apparent elastic modulus in both axial and bending (flexural) modes for non-hystoelastic metals.

DMA provides a useful technique for determination of the apparent elastic modulus in both axial and bending (flexural) modes for very small prismatic beams (uniform cross-sections).

2.0 Three-Point Bend Testing of NiTi Beams 2.1 Introduction

Exploratory dynamic testing on a variety of NiTi struts using a sinusoidal loading mode completed at 37° C. using a custom DMA fixture with a 3.5 mm span length revealed very low apparent flexural moduli (AFM) with values ranging between 15 GPa and 25 GPa representing around 20% and 35% of the anticipated austenite modulus (Ea) of 68-83 GPa. More formal testing was completed in quasi-static mode on struts cut from 'generic stents'. Generic stents are custom designed test vehicles possessing relatively long near-prismatic struts rendering them more useful for mechanical testing. Stent strut specimens were cut from generic stents made at Medtronic in Santa Rosa, Calif. ("Skylane") and from stents made by Laserage Technology Corporation, Waukegan, Ill. Differential scanning calorimetry (DSC) was completed on specimens from both sources to ensure common transformational properties. Since generic stents from both sources were made to a prescribed thermomechanical schedule (time, temperature and strain increment), transformational temperatures and latent heats were very similar, refer to Table 3.

TABLE 3

Mean transformation temperatures for n = 5 Skylane and n = 5 Laserage specimens determined using TA Discovery 2000 DSC via full and partial cycle thermal cycles; the lower row provides the absolute difference between mean transformation temperatures for Laserage and Skylane specimens.

| | Transformation Temperature (° C.) | | | | | | | |
|---|---|---|---|---|---|---|---|---|
| | $R'_s$ | $R'_f$ | $M_s$ | $M_f$ | $A_s$ | $A_f$ | $R_s$ | $R_f$ |
| Laserage (LSG) | −5.54 | 7.53 | −51.25 | −72.55 | 2.40 | 7.96 | 6.86 | 0.81 |
| Skylane (SKY) | −3.67 | 8.98 | −50.30 | −71.21 | 4.05 | 9.11 | 7.12 | 1.38 |
| Diff LSG Vs. SKY | 1.88 | 1.44 | 0.95 | 1.34 | 1.65 | 1.14 | 0.26 | 0.58 |

2.2 Test Method 2

Testing was completed in 3-point bend at 37° C. in force-controlled mode with the dynamic loading control deactivated, in this manner the DMA was used as a miniature conventional mechanical test frame. Load was applied using a steady ramp up to a maximum force of 6N. The bending stresses never exceeded 325 MPa which is presumably below the magnitude necessary for stress inducing the martensite phase (σSIM), accordingly, all force vs. displacement plots were relatively linear. All specimen dimensions and span length (nominal 3.5 mm) were measured with micron accuracy using, a calibrated optical measurement system, apparent flexural modulus was computed via the beam equation (Equation A1) using the gradient of the force-displacement plot plus appropriate 2nd moment calculations for the isosceles trapezoidal cross-section struts (Equation A2), refer to FIG. 21.

$$E_{bend} = \frac{L^2}{48I} \times \frac{\delta F}{\delta d} \qquad \text{Equation A1}$$

$$I_{(x_c)} = \frac{h^2(3a+b)}{12} \qquad \text{Equation A2}$$

2.3 Results—Method 2.

Figure 20:
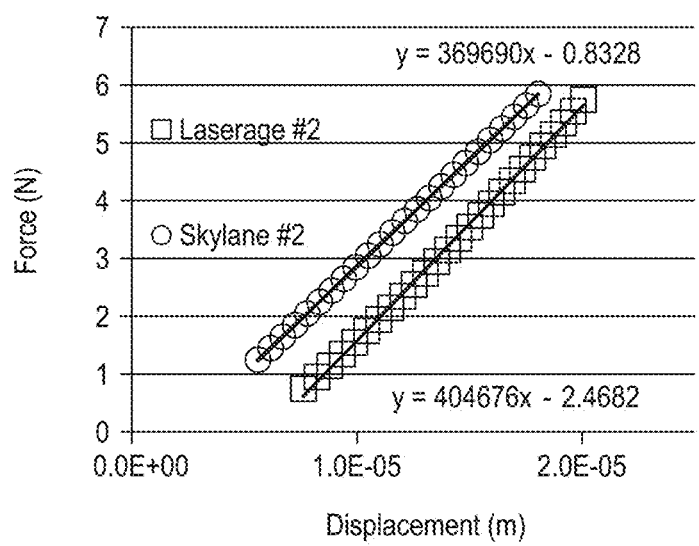
FIG. 20 is a force versus displacement plot for representative struts cut from Laserage and Skylane fabricated generic stents, tests completed in 3-point bend at 37° C. using a TA Q800 DMA.

A plot of two representative specimens (Laserage #2, and Skylane #2) is shown in FIG. 20. Test results are provided in Table 4. One specimen Laserage replicate #1 was poorly behaved; accordingly, the data point has been censored and is not used, in computation of the mean value for that population.

TABLE 4

Flexural storage modulus values for n = 5 replicates (rectangular beam and round wire), note the relatively small scatter and close agreement between the two means.

| Replicate | Flexural Modulus, E, ×10⁹ (GPa) | |
|---|---|---|
|  | Laserage | Skylane |
| #1 | 22.70* | 27.04 |
| #2 | 31.51 | 28.80 |
| #3 | 33.24 | 33.87 |
| #4 | 29.74 | 35.15 |
| #5 | 30.61 | 34.19 |
| Mean | 31.28 | 31.81 |

*Poorly Behaved Specimen, censored data point 2.4 Discussion Test Method 2

The values presented in Table 4 are substantially lower than anticipated. The established modulus for austenitic NiTi (Ea) is given around 68 to 83 GPa depending on source, moduli of 68-72 GPa are routinely measured internally using 8" tube specimens+clip on strain gauge in uniaxial tension, suggesting the possibility that the struts being tested were 100% austenite. For example, there could be local stress-induced transformation at the knife-edges during the 3-point bend test. There are numerous factors that can conceivably shift the modulus in a flexural test, either 3-point or 4-point bending, refer to Table 5 for common sources of error encountered in 3-point bend tests.

TABLE 5

Some common sources of error encountered in 3-point bend testing (non-exhaustive).

| Possible Source of Error in 3-Point Bend Test | Implication |
|---|---|
| Initial specimen curvature | Intrinsic neutral axis shift |
| Excessive shear stress | Small test span to specimen height ratios |
| Excessive specimen height to breadth ratio | Tall specimens tend to rotate |
| Material asymmetries | Different modulus in tension vs. compression |
| Misaligned middle anvil | Force acts at an angle across the section |
| Frictional at specimen-fixture interface | Other suppers ideally rollers, inner need not be |
| Direct contact stresses | Hertzian contact |
| Wedging stresses | Stress distribution in immediate vicinity of contact |
| Contact point tangency shift | Acts to effectively shorten the moment art |
| Coarse specimen measurement | Incorrect dimensions = incorrect beam eq. solution |
| Irregular cross-section | Can lead to twisting and rotation |

Because NiTi exhibits stress-induced transformations B2→B19', B2→R and R→B19', and since the transformations may be orientation dependent, i.e., they preferentially occur more readily in certain crystallographic directions versus others (Schmid factor dependency). Work was completed to determine whether the strong texture of the NiTi tubes plus loading from a different direction (bending versus axial) is implicated in the observed results.

Implication of Texture?

Polycrystalline materials are aggregates of many crystal grains of various sizes, shapes, and orientations; each single crystal possesses planes of atoms. The relative alignment of these planes throughout the aggregate are important since the mechanical anisotropy in polycrystalline materials (i.e. different mechanical properties in different directions) results from the direction-dependent response of the single crystals from which they are comprised. For single crystals, the same loading applied in different directions (e.g. a tensile stress) will elicit different responses (e.g. elastic strains). In simple terms, if a property such as the stress-strain response is anisotropic in the individual grains and if there is a distribution of grains of different orientations (texture) in the polycrystalline material, then the property will also be anisotropic in the polycrystalline material, be it elastic, superelastic or plastic.

The macroscopic behavior of polycrystalline materials can be regarded as isotropic and homogeneous in terms of elastic deformation when the materials have random crystallographic texture and the ratio of their elastic constants is close to unity. In reality, wrought polycrystalline materials possess a preferred crystallographic texture due to rotation of the grains during processing, furthermore, with the exception of tungsten, most metals and alloys possess different properties in different crystallographic directions. As the number of grains gets fewer, the macroscopic Young's modulus of a given micro-structure becomes increasingly dependent on the crystal orientations of individual grains plus the elastic anisotropy ratio of the single crystals; elastic anisotropy typically expressed by the Zener anisotropy ratio (ZA), refer to Table 7. For small struts fabricated from highly textured tube possessing a relatively small number of grains and possessing a significant anisotropy (ZA for B2 NiTi≈2.7), it is therefore assumed that there will be a small difference between flexural modulus and tensile modulus. The initial question can be asked more specifically.

Question:

Can directional (angular) differences in elastic modulus associated with crystallographic texture account for the 60% difference between the accepted axial modulus of austenite (70-75 GPa) versus those determined via DMA 3-point bend testing (30 GPa)?

Taking published values for the elastic constants for a variety of metals including NiTi B2 plus the directional cosines (Table 6), using Equation 3A, the Young's modulus is readily computed for the three chief directions in a cubic lattice, viz., <111>; <100>; and <110>, refer to Table 7. Subsequently via simple trigonometry (Equation 4A), assuming <100> are the most compliant direction(s) and <111> the most stiff, the angular variation in elastic modulus is computed, refer FIGS. 22A-B.

TABLE 6

The direction cosines for the primary directions in cubic lattice. These cosines are used to compute the elastic modulus in a given direction via Equation 3A.

| Directions | $l_{i1}$ | $l_{j2}$ | $l_{k3}$ |
|---|---|---|---|
| <100> | 1 | 0 | 0 |
| <110> | $1/\sqrt{2}$ | $1/\sqrt{2}$ | 0 |
| <111> | $1/\sqrt{3}$ | $1/\sqrt{3}$ | $1/\sqrt{3}$ |

Using the direction cosines provided in Table 6 the equation for determining the elastic modulus in a given direction is as follows:

$$\frac{1}{E} = S_{11} - 2\left[(S_{11} - S_{12}) - \frac{1}{2}S_{44}\right](l_{i1} + l_{j2} + l_{k3}) \quad \text{Equation 3A}$$

Substituting values of E<100> and E<111> computed using Equation 3 into Equation 4 allows computation of the modulus in any direction E<hkl>.

$$\frac{1}{E_{[hkl]}} = \frac{1}{E(100)} - 3\left\{\frac{1}{E(100)} - \frac{1}{E(111)}\right\}(\alpha^2\beta^2 + \alpha^2\gamma^2 + \alpha^2\gamma^2) \quad \text{Equation 4A}$$

$\alpha = \cos\theta$ $\beta = \cos 90° - \theta = \sin\theta$ $\gamma = 0$

Elastic moduli for three directions are provided for a variety of pure metals and B2 NiTi in Table 7 below. The values for tungsten and copper are well known and used check that the computations are yielding the correct moduli for the single crystal B2 NiTi.

Because Cu is known to be relatively anisotropic for a pure metal we anticipate that it is most likely to exhibit the largest range of elastic moduli across of broad range of wrought forms where the potential lies for a large range of different textures. The validity of this speculation is corroborated by reference to the published literature [H. R. Ledbeter and E. R. Naimoli, Elastic Properties of Metals and Alloys. II. Copper, Journal of Physical and Chemical Reference Data, October 1974; 3(4), Pages 912-923. http://www.nist.gov/data/PDFfiles/jpcrd57.pdf], with reference to Ledbetter and Naimon's paper (Ledbeter, Pages 912-923) they provide extensive elastic modulus data for room temperature polycrystalline Cu (includes a variety of purities and processing). Taking 130 GPa as a typical quoted value to benchmark against, values are observed anywhere from around 85 GPa to 140 GPa with an average of 123.5 GPa from the entire survey. i.e., a 40% difference in spread smallest to largest.

With reference to FIG. 22E and the second from right column in Table 7, it is evident that the lowest modulus anticipated for NiTi $2 is around 45 GPa.

2.5 Conclusion Test Method 2.

It can be concluded that apparent austenite modulus values lower than 45 GPa are not solely attributable to the directional nature of loading combined with anisotropy of Young's modulus (B2) of strongly textured specimens during a 3-point bend test.

3.0 Three-Point Bend Testing of NiTi Beams at Elevated Temperatures 3.1 Introduction Although it has been shown in Section 2.4 that mechanical anisotropy of the B2 phase cannot account for observed discrepancies in modulus, it is recognized that R-phase and martensite (B19') possess relatively low apparent moduli and considerable tension/compression asymmetry. Accordingly, stress-induced transformations may be implicated in the lowering of the moduli. The lower threshold for stress-inducing the B2→B19' transformation in polycrystalline specimens is assumed to be around 300 MPa, since the discrepant moduli are observed in tests operating within the elastic region well below the upper plateau stress it is reasonable to conclude that 'premature' B2→B19' transformation is not a primary suspect. While it is well known that appearance of the R-phase causes a bending/softening of the elastic modulus immediate adjacent to the on-set of the upper plateau, it has been assumed that the so-called austenite modulus is not macroscopically impacted by the stress-induced R-phase transformation. Since the R-phase

TABLE 7

Elastic modulus computed for the primary directions in the cubic lattice.

| | C44 | S44 | C11 | S11 | C12 | S12 | Elastic Anisotropy, $Z_A$ 2 * C44/ (C11 − C12) | Elastic Modulus (Pa) | | |
|---|---|---|---|---|---|---|---|---|---|---|
| | | | | | | | | <111> | <100> | <110> |
| W | 1.51E−09 | 6.60E−12 | 5.01E−09 | 2.60E−12 | 1.98E−09 | −7.00E−13 | 1.0 | 3.85E+11 | 3.85E+11 | 3.85E+11 |
| Cu | 7.54E−10 | 1.33E−11 | 1.68E−09 | 1.50E−11 | 1.21E−09 | −6.28E−12 | 3.2 | 1.91E+11 | 6.67E+10 | 1.30E+11 |
| Ta | 8.50E−10 | 1.18E−11 | 2.62E−09 | 7.11E−12 | 1.60E−09 | −2.7E−12 | 1.7 | 2.23E+11 | 1.41E+11 | 1.94E+11 |
| NiTi (B2) | 4.00E−10 | 2.50E−11 | 1.69E−09 | 2.23E−11 | 1.38E−09 | −1.00E−11 | 2.6 | 1.10E+11 | 4.49E+10 | 8.08E+10 |

With reference to Table 7, the Zeiler anisotropy ratio (ZA) for Ta is relatively low, by comparison W is almost perfectly isotropic with ZA=1.0 and Cu anisotropic with ZA=3.2.

transformation is immediately followed by further deformation of the rhombohedral lattice and subsequent reorientation of R-phase variants, the R-phase transformation is highly anelastic. Given the observation of R-phase in close proximity to the upper plateau and its highly anelastic behavior, the prevailing wisdom has been that if R-phase was implicated at low stresses it would manifest as macroscopically observed non-proportionality in the stress-strain data. Since a significant proportional stress-strain relationship is observed in those specimens exhibiting diminutive moduli, direct implication of the R-phase has typically been dismissed.

Regardless of the conventional wisdom, if appreciable stress-induced transformation occurs during loading (regardless of its origin) it could result in a dramatic skewing of the apparent modulus, this is especially true for smaller specimens since stress-transformed material could represent a significant portion of a small beam (dimensions breadth and height <550 μm). Furthermore, similarity of the values obtained ≈30 GPa (refer to Table 4) with those established for the martensite phase (28 to 41 GPa) cast uncertainty on the state of the material being tested.

3.2a. Test Method 3A.

To avoid transformation altogether during testing it is necessary to heat specimens to a temperature above which the stress-induced transformation cannot occur, this temperature is known as the martensite desist temperature (Md). Above Md the NiTi behaves like a conventional non-hystoelastic metal, no superelastic behaviour is observed. A cursory literature search revealed an Md value of 80° C. [McKelvey & Ritchie, On the temperature dependence of the superelastic strength and the prediction of the theoretical uniaxial transformation strain in Nitinol, Philosophical Magazine A, Volume 80, Issue 8, 2000], confirmation was attempted using dynamic DMA via cooling scans from 140 to 0° C. In apparent agreement with [McKelvey & Ritchie], an abrupt inflection was observed at 80° C., refer to FIGS. 23A-B.

Quasi-static testing was completed on a variety of equiatomic NiTi specimens including Skylane Generic Stent struts (see Section 2) assuming an Md temperature of 80° C. Testing was completed in 3-point bend at 37° C. in force-controlled mode with the dynamic loading control deactivated. Load was applied using a steady ramp up to a maximum force of 6N.

3.3a. Results—Method 3A

The highest elastic modulus projected at 37° C. from this data via simple linear regression never exceeded 20 GPa regardless of specimen type.

The flexural storage modulus computed using dynamic DMA testing concurrent with temperature cycling routinely report excessively high dynamic moduli for the NiTi specimens, for example, refer to Section 7.4 Discussion Test Method 7. This discrepancy is discussed in Section 7.0.

3.2b. Test Method 3B

The Md of many transformation induced plasticity (TRIP) steels occurs around 300° C., it was therefore speculated that the Md of NiTi could be somewhat higher than 80° C. (Method 3A). Furthermore, NiTi-specific literature searches revealed Md values ranging from 150° C. [Fonte & Saigal, Shape Recovery Effects of Solid, Forged Nitinol for Orthopedic Applications, Medical Device Materials V; Proceedings from the Materials & Processes for Medical Devices Conference 2009 (ASM International)], 160 to 200° C. [Stoeckel & Yu, Superelastic Ni—Ti Wire, Wire Journal International, March 1991, pp. 45-50], through 310-320° C. [Benafan et al., Temperature dependent deformation of the B2 austenite phase of a NiTi shape memory alloy, International Journal of Plasticity 51 (2013) 103-121] depending on the wrought form and condition of the material being tested.

Figure 23B:
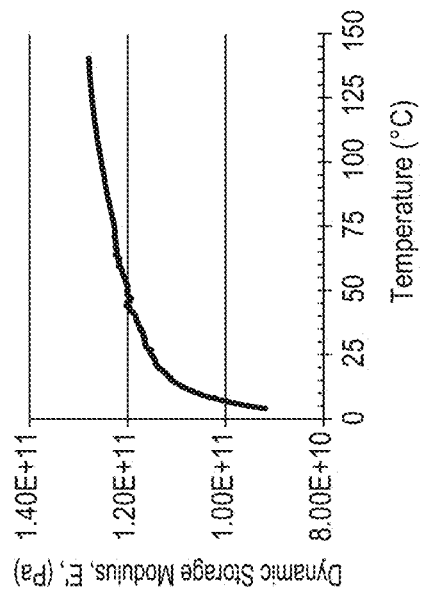
FIG. 23B is a plot of Storage modulus vs. temperature for a mini-dogbone specimen heat-heat treated in accordance with Engager TCV, Af 20±5° C. Dynamic DMA test in 3-point bend while cooling from 140° C. to 0° C. at a rate of −3° C./minute.
Figure 23A:
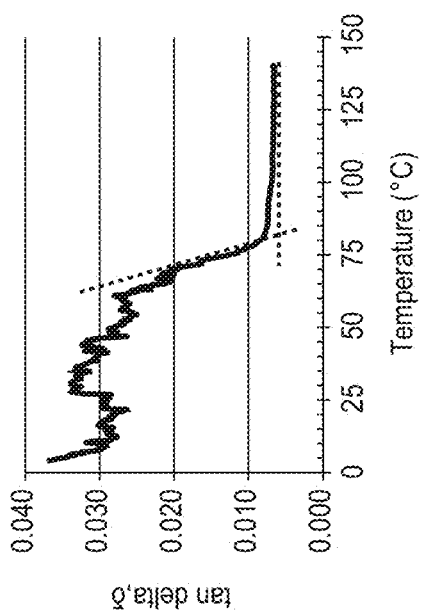
FIG. 23A is a plot of Tan delta vs. temperature for a mini-dogbone specimen heat-heat treated in accordance with Engager TCV, Af 20±5° C. Dynamic DMA test in 3-point bend while cooling from 140° C. to 0° C. at a rate of −3° C./minute.

Due to the ensuing uncertainty, additional dynamic DMA was completed using cooling scans from 300 to 0° C., plots of tan delta vs. temperature revealed a step change at 275° C. indicating abrupt changes in elastic/viscous behaviour, refer to FIG. 23A. Subsequently quasi-static DMA test in 3-point bend was completed at 225, 250, 300, and 422° C.

3.3b. Results—Method 3B

Data showed some curvature in the Modulus vs. Temp. plot, i.e., softening, refer to FIG. 23B.

The highest modulus projected at 37° C. from this data via simple linear regression using the two highest temperature values was 35.3 GPa.

3.2c. Test Method 3C

Figure 24B:
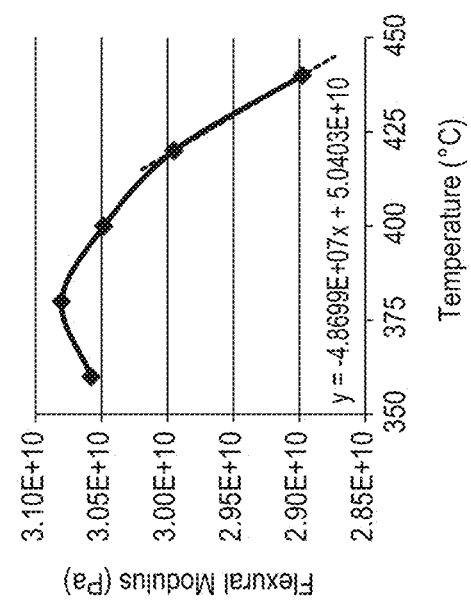
FIG. 24B is a plot of flexural modulus vs. temperature for a generic stent strut specimen, Af≈9° C. Quasi-static DMA test in 3-point bend at 360, 380, 400, 420, and 440° C.
Figure 24A:
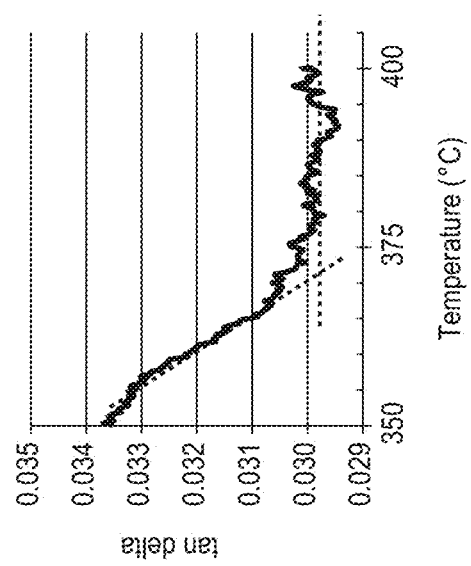
FIG. 24A is a plot of tan delta vs. temperature for a generic stent strut specimen, Af≈9° C. Dynamic DMA test in 3-point bend while cooling from 400° C. to 0° C. at a rate of −3° C./minute.

Based on the assumption that Md was yet higher than 300° C. specimens were heated to 400° C. and cooled to zero in accordance with the previous protocol, a step change in the tan delta vs. temperature plots was identified at around 375° C., the assumption was made that Md=375° C., refer to FIG. 24A. Assuming Md=375° C., the same type of 3-point bend test as those completed for the n=5 Skylane and n=5 Laserage struts (Method 2) were completed at T=360, 380, 400, 420, and 440° C. using a single specimen replicate at each discrete temperature, refer to FIG. 24B.

3.3c. Results—Method 3C

With reference to FIG. 24B, using the two highest temperature values only, a revised modulus of 48.6 GPa was estimated using simple linear regression to extrapolate to 37° C. This value remains around 35% lower than the anticipated value (68+83/2)=75 GPa.

3.4 Discussion Test Method 3A, 3B, and 3C

By inspection of FIGS. 22A through 24B, attempts to identify Md using dynamic DMA plus temperature scans and subsequent fixed temperature quasi-static DMA testing was not particularly successful. From the work completed (Methods 1A and 1B) it is evident that 3-point bend testing using dynamic and quasi-static DMA can provide a useful tool for determining modulus, albeit only proven for 'conventional' metals. Furthermore, it has been demonstrated that texture effects alone cannot account for the low values of modulus observed for the NiTi struts (refer to Discussion Method 2). Given the apparent failure of the high temperature tests intended to derive transformation-free moduli, further high temperature testing was abandoned to focus on other approaches that might yield more informative results 4.0 Literature Review & Re-Analysis of Published Data 4.1 Introduction A literature review was completed to provide a benchmark for comparison with available test results. The literature review was restricted to bend testing, i.e., focused on flexural modulus and therefore it necessarily draws on data generated for orthodontic applications (test temperature typically =35° C.) acquired from a variety of 3-Point, 4-Point, and cantilever beam testing. In general, the orthodontic research papers placed an emphasis on brand-specific archwire properties and often lack displacement data. A survey of non-orthodontic literature revealed similar discrepancies as those observed in the current work with quoted values of flexural modulus ranging from 25-55 GPa. The upper value of 55 GPa is an exception rather than a norm, a more common upper limit of around 45 GPa is evident when broader ranges of data are surveyed. One paper by R. P. Kusy and A. M. Stush [Geometric and material parameters of a nickel-titanium and a beta titanium orthodontic arch wire alloy, Dent Mater. 1987 August; 3(4):207-17] compares mechanical properties of ten (10) equiatomic NiTi and seven (7) beta titanium (T.M.A.) [The T.M.A.™ β-titanium material (Ormco Corp., Glendora, Calif.) possesses the following approximate composition: 79% Ti, 11% Mo, 6% Zr, and 4% Sn] sizes of orthodontic arch wires tested in both 3- and 4-point bending with moduli values calculated for n=220 data sets in both loading and unloading. The paper provides a thorough account of the experimental technique plus diligent reporting of all dimensions plus details necessary to re-plot elements of their extensive data to allow further scrutiny.

4.2 Analysis Method 4

The following provides a summary of the Kusy and Stush protocol focused on testing straight portions of NiTi and conventional alloy (none-hystoelastic) archwires. Ten sizes of nickel-titanium orthodontic arch wires of round, square and rectangular sections were tested in both 3- and 4-point bending, rectangular wires were evaluated in the edgewise and flatwise orientation. Specimens were tested using a range of different span lengths from 0.35" (8.9 mm) through 1.0" (25.4 mm). Collectively n=121 NiTi data sets were collected in both loading and unloading (n=242 total). The authors, among other things, down selected nine (n=9) span lengths from 24 using the following criteria:

A. that the applied force be limited so that the true deflection did not exceed 5% of the total distance between outer supports;
B. that the dead load deflection does not exceed 0.05% of the total true deflection; and
C. that the machine deflection does not exceed 0.5% of the true deflection.

An Instron Universal Testing Machine loaded at 0.05 cm/min was used for all testing. Straight segments of preformed arch wire were tested in both 3- and 4-point bending @ 35° C. (temp. oral cavity). All wires and span dimensions were measured to ±0.00001" (0.254 µm). Each specimen was loaded and unloaded 10 times and the mean was computed. Each rectangular specimen configuration evaluated in the edgewise and flatwise orientation.

Figure 25:
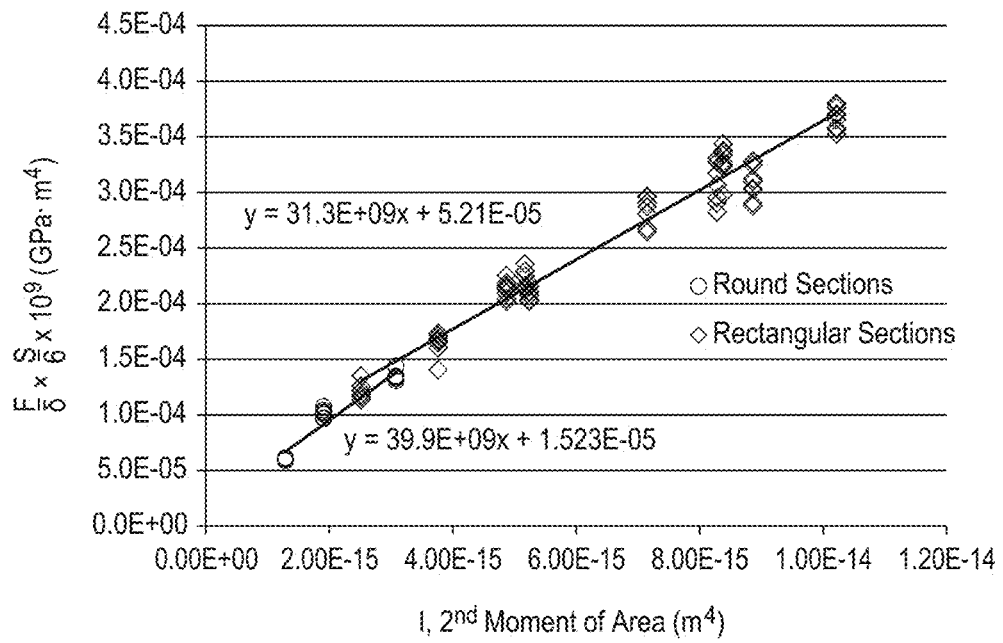
FIG. 25 is a plot of stiffness versus 2nd moment of area for equiatomic NiTi beams in 3- and 4-point bending at 35° C. comprising of n=84 rectangular and n=21 round specimens. The slope of plot represents the apparent flexural modulus.

Further re-analysis of the Kusy and Stush NiTi specimen data revealed a variation in the apparent flexural modulus (Ef) from a mean of 4.54 Msi (31.3 GPa) for pooled square plus rectangular wires and 5.79 Msi (39.9 GPa) for round wires, refer to FIG. 25.

These observations were consistent with those previously reported in the literature. A literature review completed by the authors (Kusy and Stush) as reported in their paper, shows that most studies with a few exceptions, which involves cantilever bend testing, obtained flexural modulus values in the vicinity of either 44 or 33 GPa.

Differences in the AFM, viz., ~44 GPa for round sections vs. ~33 GPa for pooled square and rectangular sections are tentatively attributed by the authors to the "inherent non-linear elasticity" of NiTi, they speculate that are likely to vary even more for "those alloys which display stress-induced and thermally-induced shape memory". According to authors, "Provided the spans complied with the beam criteria stated earlier, the elastic moduli were independent of span index (Equation 5A). This relationship was checked, and as asserted by the authors, no correlation was observed. According to the authors, and apparently also on the basis of their extensive pre-screening exercise and specimen inclusion criterion, they assert that the experimentally derived flexural moduli should also be independent of wire configuration and nominal wire size, and while the authors reported that the moduli of the round Nitinol wires were routinely greater than the rectangular NiTi wires, the rectangular wire data was reassessed to ensure that this also applied for the rectangular beams.

Span index ranks the effective length of one span combination versus another:

$$\text{Span Index} = L3*(L3+3\times L4)[(L1-L2)/2]*[(L1-L2)/2 (3L2/20]$$

Equation 5A 4.3 Results—Method 4. (Re-Analysis of Published Data)

Figure 26:
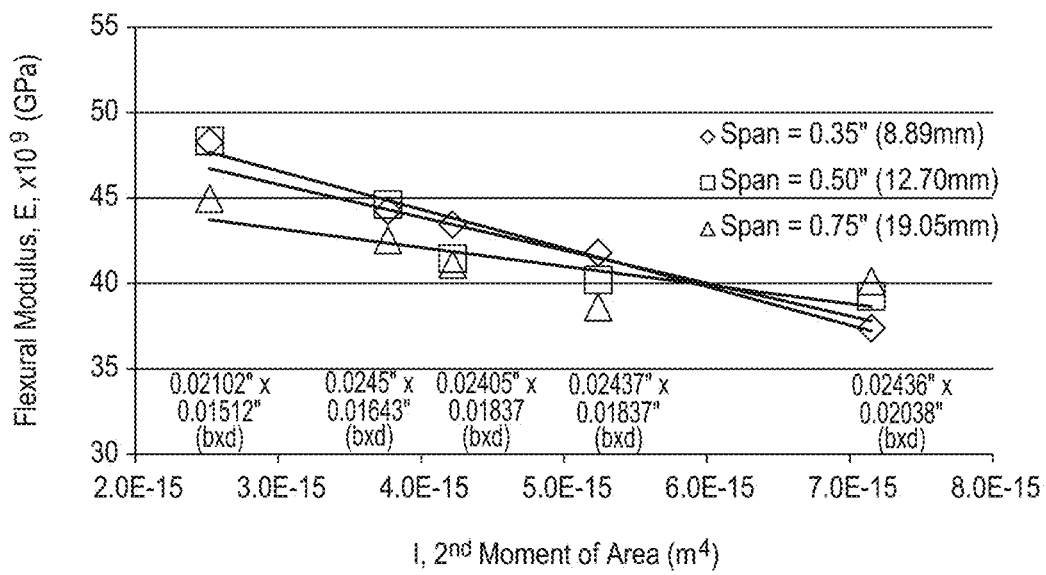
FIG. 26 is a plot of flexural modulus versus 2nd moment of area for equiatomic NiTi beams in 3-point bending, flatwise rectangular specimens (dimension provided) at 35° C., three different span lengths.

Available 3-Point bend modulus data for rectangular specimens in their flatwise orientation over span length of 0.35, 0.5, and 0.75" was plotted versus 2nd moment of area, these plots immediately revealed an inverse relationship between 2nd moment of area and modulus as a function of span length thereby challenging the validity of the assertion made by the authors, refer to FIG. 26. For additional confirmation, the flexural modulus versus specimen height 'h' for rectangular specimens in both 3-point and 4-Point bending, in flatwise and edgewise orientations at 35° C. for three different span lengths refer to FIG. 27. The trending observed in FIG. 26 persists such that apparent flexural modulus is dependent on specimen geometry regardless of specimen orientation and regardless of test mode (3-Point or 4-Point bend).

Figure 28:
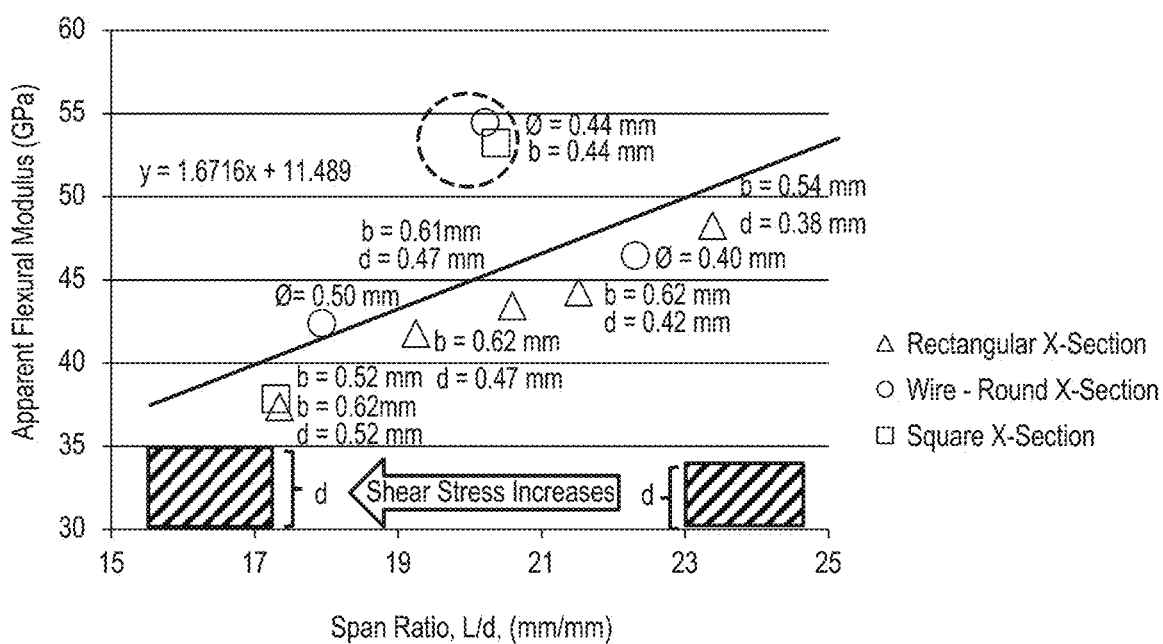
FIG. 28 is a plot of flexural modulus versus specimen height 'h' for equiatomic NiTi rectangular specimens in both 3-point and 4-Point bending, in flatwise and edgewise orientations at 35° C., three different span lengths (span lengths provided).

With a geometric dependence firmly established, data for rectangular, round and square sections and a span length (L) of 0.35" (8.89 mm) was re-plotted in terms of AFM versus Span Ratio (SR) where SR is given by the length of the outer span 'L' (mm) divided by the specimen height (or depth) 'd' (mm), refer to FIG. 28. SR provides a reliable substitute for the ratio of shear stress and bending stress (Equation 6A), for very short beams (small values of SR), the bending stress is small and the shear stress is relatively large. In this context a beam may be categorized as a long beam if the length of the beam exceeds 10 times the depth.

With reference to FIG. 28, for all specimens and orientation over three different span lengths, a clear trend is observed showing an inverse relationship between AFM and SR. The 0.4 mm diameter round wire and the b=0.4 mm square section wire coincide as outliers with both exhibiting significantly larger moduli than specimens with similar 2nd moments. In accordance with the fixed 0.35" span data (round, square & rectangular), the rectangular sections clearly show AFM being inversely proportional to SR, i.e., for a fixed value of 'd', the modulus was found to be lower for a shorter beam versus a longer beam.

The ratio of the shear contribution to the bending contribution is given by Equation 6A [16].

$$\frac{PLh^2/40GI}{PL^2/24EI} = \frac{3h^2E}{5L^2G}$$

Equation 6A

By inspection of Equation 6A, the importance of the shear term scales as $(h/L)^2$, where 'h' is interchangeable with 'd', i.e., quadratically with the span length-to-height ratio. Apparent flexural modulus was plotted versus the shear to bending ratio for Kusy and Stush NiTi and T.M.A.™ rectangular specimens in 3-Point bending and flatwise orientations at 35° C., three different span lengths are plotted, the specimen dimensions are provided on the plot, refer to FIG. 29.

4.4 Discussion Test Method 4.

Figure 27:
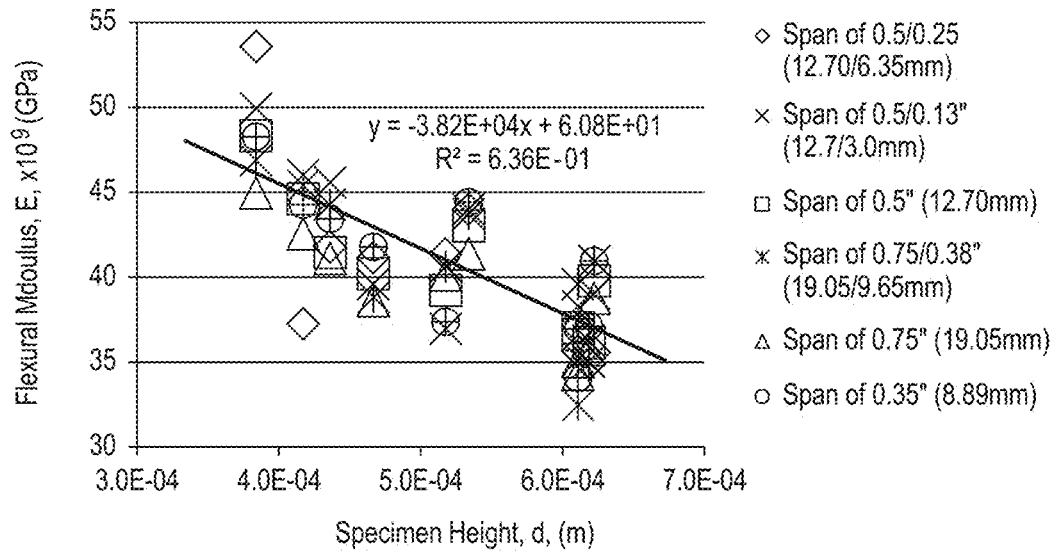
FIG. 27 is a plot of flexural modulus versus specimen height 'h' for equiatomic NiTi rectangular specimens in both 3-point and 4-Point bending, in flatwise and edgewise orientations at 35° C., three different span lengths—span lengths provided expressed in terms of outer/inner for 4-point bending.
Figure 29:
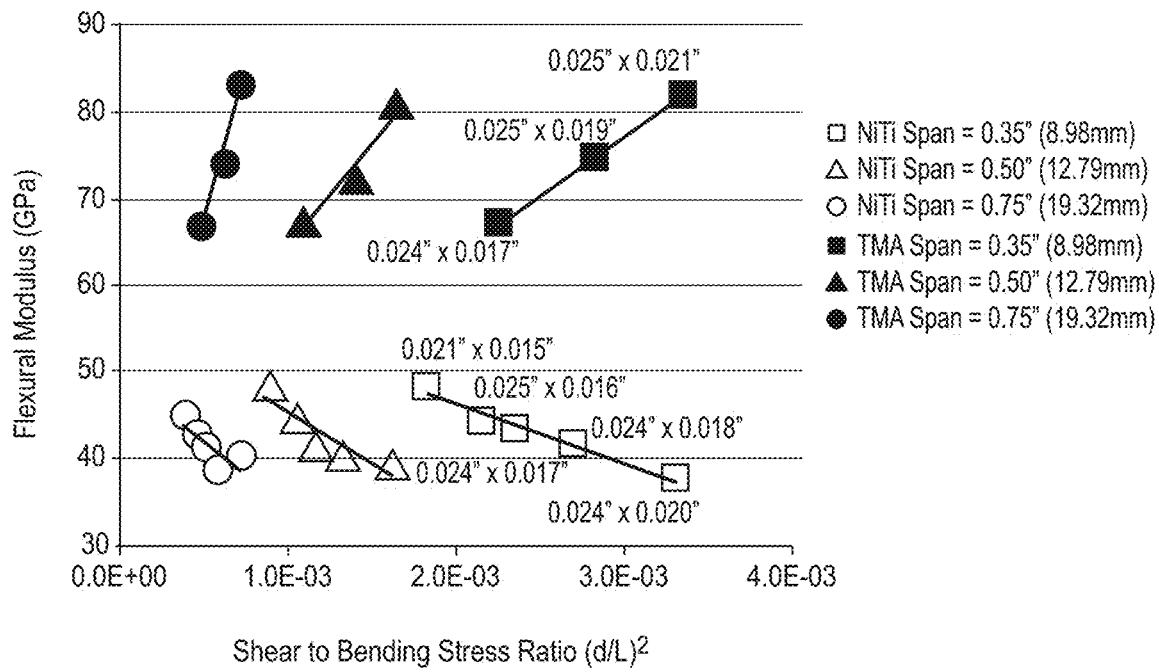
FIG. 29 is a plot of flexural modulus versus the shear to bending ratio for deflection of NiTi and T.M.A.™ rectangular specimens (dimensions provided) in 3-Point bending, in flatwise orientations at 35° C., three different span lengths (span lengths provided). Specimen dimensions are given in terms of nominal b×d, the exact dimensions vary slightly such that for example, the 0.024"×0.017" NiTi is of a slightly different size than the equivalent nominally sized T.M.A.™ specimens, hence nominal data points in each population are not vertically aligned on the plot despite having common span lengths.

The trending presented in FIGS. 26-28 culminating in direct comparisons of NiTi with the conventional T.M.A.™ material in FIG. 29 reveal a counterintuitive relationship between specimens, dimensions, and modulus. With reference to the simple schematic at the bottom of FIG. 28, it is clear that for a given span length, the 'fatter' T.M.A.™ specimens confer greater stiffness, in direct contrast, for any fixed span length the 'fatter' NiTi specimens exhibit increased compliance.

From these trends, it is evident that the shear contribution has a profound impact on the deflection of NiTi specimens. On the basis of these results it is possible to formulate a variety of working hypotheses to describe the observed behavior of the NiTi specimens. Some possible explanations are provided below (A-D).

A. The observed "softening" of the beams is associated with stress-induced transformation.

B. Elevated shear stresses shift the neutral axis.

C. Material asymmetries, i.e., differences in elastic modulus in compression versus tension shift the neutral axis.

D. Other mechanism implicating elevated shear stresses, e.g., other elements include in Table 5.

Regardless of which explanation/hypothesis is favored, by direct comparison of the results acquired from the T.M.A.™ specimens versus those acquired from the NiTi specimens (FIG. 29), it is clear that a valid explanation necessarily implicates the shear-to-bending stress ratio as given by Equation 6A.

4.5 Conclusion Test Method 4

If it is assumed that stress-induced transformation is implicated, since the stresses encountered in the tests are typically lower than that necessary to stress-induce martensite (B19'), then the implicated stress-induced phase must necessarily be the rhombohedral phase (R-phase).

5.0 NiTi Round Wire Testing

5.1 Introduction

Near equiatomic NiTi alloys typically exhibit three crystallographic phases: the high-temperature cubic B2 austenite phase, the low-temperature monoclinic B19" martensite phase and at an intermediate temperature the rhombohedral R-phase. Possible phase transformations between these phases are as follows: the B24↔B19' (A↔M) transformation, the B24↔R-phase (A↔R) transformation and the R-phase↔B19' (R↔M) transformation. All three transformations are martensitic in nature, i.e. they involve essentially diffusionless lattice distortion transitions. All three phases can be stabilized and destabilized by application or removal of energy, where the energy can be either thermal or mechanical. Rather than speculating on the exact source of the "softening", a test protocol was developed focused on exploring the flexural behavior of thermally stabilized austenite and R-phase.

5.2 Test Method 5

This study employed four (4) different round wire diameters and four (4) span lengths. The testing was completed in force-controlled 3-point bending mode (refer to Tables 9 and 10). Maximum load (N) for each span plus wire diameter combination was computed to achieve a maximum engineering strain of 0.6%. A load rate (Ns−1) equivalent to an isothermal strain rate of $10^{-4}s^{-1}$ was targeted for all wire diameter and span length combinations. All specimen diameters were measured using a calibrated Mitutoyo benchtop micrometer (Cal. # E5029326), refer to Table 9.

TABLE 9

Mean values of wire diameter (mm) for n = 3 measurement replicates of a discrete specimen.

| Nominal Ø (inch) | Nominal Ø (mm) | Measurement Replicate (mm) | | | Mean |
|---|---|---|---|---|---|
| | | #1 | #2 | #3 | |
| 0.016 | 0.406 | 0.406 | 0.408 | 0.406 | 0.407 |
| 0.025 | 0.635 | 0.640 | 0.638 | 0.640 | 0.639 |
| 0.030 | 0.762 | 0.765 | 0.762 | 0.765 | 0.764 |
| 0.035 | 0.889 | 0.886 | 0.889 | 0.889 | 0.888 |

All span lengths were measured using a calibrated Mitutoyo optical measurement system with Quadrachek 200 software (Cal. #52562), refer to Table 10.

TABLE 10

Mean values of span lengths (mm) from n = 3 measurement replicates of the 3-Point Bend fixtures.

| Span (mm) | Measurement Replicate (mm) | | | Mean |
|---|---|---|---|---|
| | #1 | #2 | #3 | |
| 3.5 | 3.576 | 3.540 | 3.553 | 3.553 |
| 5.0 | 5.022 | 5.020 | 5.020 | 5.021 |
| 10.0 | 9.992 | 9.994 | 9.996 | 9.994 |
| 15.0 | 15.010 | 14.994 | 14.988 | 14.997 |

Heating/cooling regimes plus final test temperature were manipulated to yield two different initial thermally stabilized material phases, viz., austenite and R-phase. All thermal cycling necessary to achieve the target test was completed with zero applied loads. Upon loading, the two initial material phases (austenite and R-phase) facilitated investigation of a maximum of three different types of deformation process (A→M, A→R→M, and R→M). Various combinations of these three transformations are observed as a function of chemical composition, mechanical and thermal processing and the prevailing test conditions both stress and temperature. The temperatures at which these phases occur, their associated energies and hysteresis are readily characterized using differential scanning calorimetry (DSC), Data including force and deflection was collected during both loading and unloading.

Figure 30A:
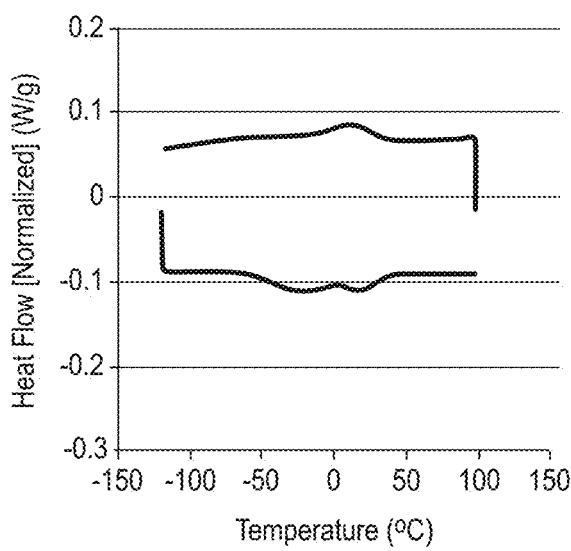
FIG. 30A is a full cycle DSC thermogram for the 0.016" Ø raw wire prior to thermal-treatment (typical of all sizes), note relatively featureless scan with weakly-defined endo- and exotherms.
Figure 30B:
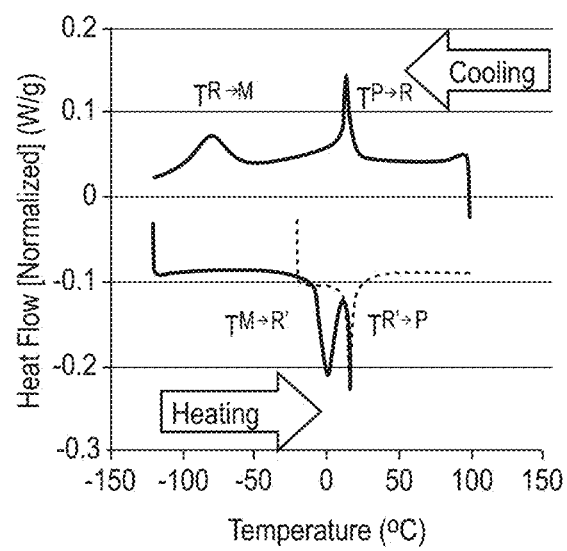
FIG. 30B is a full cycle DSC thermogram with overlaid partial heat cycle in green for the 0.016" Ø wire after thermal-treatment (typical of all sizes), 15 minutes at 500° C., note well-defined endo- & exotherms. Superscript P denotes the parent austenite phase.

The exact chemical composition and the processing history of the raw wires was not known a priori. Differential scanning calorimetry (DSC) was completed to assess the baseline condition of the four raw wires. The initial DSC revealed similar raw material conditions in all four cases, with a similar near featureless thermogram observed for each wire size, refer to FIG. 30A. Six inch (150 mm) lengths of the straight as-drawn wires were heat-treatment in their unconstrained condition for 15 minutes at 500° C. in a conventional atmospheric electric resistance furnace to develop distinct transformations. The specimens were water quenched. DSC test of the heat-treated wires revealed well defined transformation peaks presumably resulting from precipitation of Ni from solid solution into a Ni-rich phase with an anticipated but unconfirmed stoichiometry of Ni4Ti3, refer to FIG. 30B. Note the general smoothness of the peaks, local spikes in the thermogram peaks often occur when thickened oxides locally modify surface transformation, also note how the partial cycle austenite endotherm in green almost perfectly sits on top and obscures the full-cycle austenite peak beneath. Also noteworthy is how the use of the partial cycle DSC scan reveals exact location of the otherwise obscured austenite start temperature (As). In situations where the R'-phase and austenite endotherms sit right on top of one another, this same approach is equally well capable of providing definition of the individual peaks. Cooling represents the forward transformation direction from the parent phase austenite towards the daughter phase (ultimately martensite), heating represents the reverse transformation from the daughter phase (martensite) back to the parent phase (austenite).

Figure 31A:
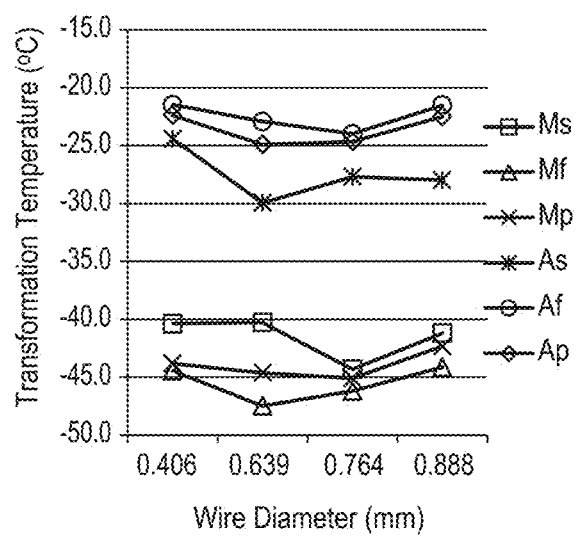
FIG. 31A is a plot of transformation temperatures for solutionized wire specimens, each data point is the mean of n=3 specimen replicates.
Figure 31B:
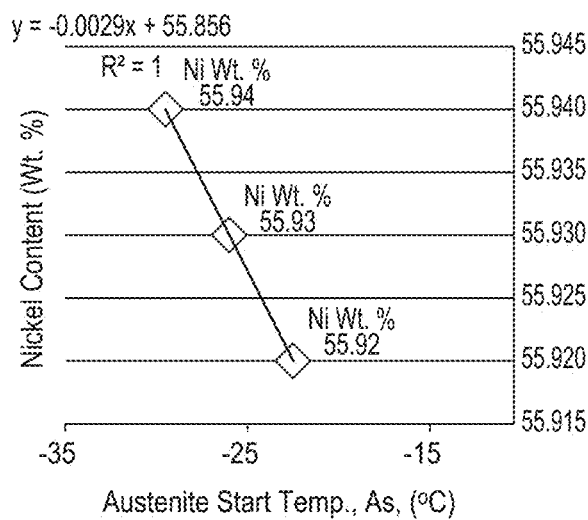
FIG. 31B is a plot of wt. % Ni content versus $A_s$ temperature for three different ingot heats used in the fabrication of CoreValve frames.

Transformation temperatures are known to scale with Ni content, As is often used as a preferred metric instead of and in lieu of chemical assay measurements. An estimate of the Ni content of the different wire diameters was attempted using DSC. The smallest diameter wire was labelled with the approximate chemical composition 56% Ni and 44% Ti, this single datum provides a rough check & balance for the Ni content estimates derived from the $A_s$ temperature measurements. The wire specimens were heat-treated in accordance with ASTM F2004 [ASTM F2004-05(2010)—Standard Test Method for Transformation Temperature of Nickel-Titanium Alloys by Thermal Analysis] involving annealing the specimens at 800° C. for 20 mins. Once heat treated the specimens will be in the solutionized condition, i.e., any nickel-rich phases, e.g., Ni4Ti3 will be "dissolved" and the Ni redistributed in the matrix. The DSC plots for solutionized specimens exhibit only two peaks, a martensite exotherm and austenite endotherm, the DSC is intended to assess the chemical contribution to the transformations. Although a vacuum or inert atmosphere is preferred, a conventional atmospheric resistance furnace was employed with a rapid water quench. Initial results showed some small differences is projected Ni content using a calibration curve acquired from ingot materials used in the fabrication of the CoreValve device. While some oxidation was inevitable; the very spikey thermograms produced were attributed to residual stresses arising from shock cooling associated with the rapid water quench. Rapid cooling of the specimens is intended to prevent any post heat-treatment precipitation from occurring. second round of testing was completed involving heat treating the test specimens on a foil tray and then allowing the specimens and the foil tray to cool together out of the furnace in room temperature air. Again, the DSC results acquired from the slower cooled specimens exhibited spikey thermogram peaks, to remedy this a short etch was attempted to remove any residual stressed layer using a 4% HF, 32% HNO3, 64% H2O etchant. The DSC results of the slow-cooled, acid-etched specimens are provided in FIG. 31A and Table 11, the 'calibration' curve acquired from Ni content—As temperature relationships observed for the CoreValve ingot material are provided in FIG. 31b. Finally, the estimated Ni contents for the four sizes of wire are provided in Table 12.

TABLE 11

Transformation temperatures for the solutionized wire specimens, each data point represents the average of n = 3 replicates.

| Diameter | Transformation Temperature (° C.) | | | | | |
|---|---|---|---|---|---|---|
| | $M_s$ | $M_f$ | $M_p$ | $A_s$ | $A_f$ | $A_p$ |
| 0.406 | −40.38 | −44.45 | −43.82 | −24.44 | −21.47 | −22.39 |
| 0.639 | −40.30 | −47.48 | −44.62 | −29.95 | −22.92 | −24.91 |
| 0.764 | −44.31 | −46.20 | −45.09 | −27.70 | −23.99 | −24.67 |
| 0.888 | −41.19 | −44.14 | −42.33 | −27.99 | −21.51 | −22.49 |

The wt. % Ni estimated using the $A_s$ values listed in Table 11 for the solutionized specimens and the relationship from the 'calibration' plot (FIG. 31B) are provided in Table 12.

TABLE 12

Estimated wt. % Ni using the As values listed in Table 11 for the solutionized specimens and the relationship from the 'calibration' plot (FIG. 18b.), each data point represents the average of n = 3 replicates. Note, the 0.406 mm Ø was labelled as 56% Ni + 44% Ti.

| Wire Size Ø (mm) | Estimated Wt. % Ni |
|---|---|
| 0.406 | 55.927 |
| 0.639 | 55.944 |
| 0.764 | 55.937 |
| 0.888 | 55.937 |

Although the estimated differences in wt. % Ni are small and are not considered reliable in absolute terms, the higher As value for the Ø=0.639 wire suggests that the Ni content is slightly elevated in this particular size of wire.

The DSC data discussed immediately above concerns solutionized specimens, all four sizes of heat-treated wire were also analyzed using DSC, full and partial cycle scans were employed. As described earlier in Test Method 5, partial cycle comprises of heating the specimen to 100° C. followed by cooling to a temperature of −20° C. which is intermediate between Rf and Ms, i.e., T (Rf+Ms)/2. Subsequently on heating the specimen transforms directly from R-phase to austenite without implicating the R'-phase. In this manner, any overlapping of the R'-phase and austenite peaks can be resolved to yield latent heats and more precise transformation temperature for each peak. Previous studies plus data provided in Section 7.0 clearly show that transformations may commence at substantially different temperatures than those indicated by the standard start temperature metric which is derived using simple triangular-like tangent-line intercept constructions. The same applies for the finish temperatures, in other words the transformations reach completion at a substantially different temperature than that indicated by the standard finish temperature. On the basis of this knowledge the true initiation and completion points of the transformations in the tails of the exo- and endo-therms were identified to ensure that a particular phase could be thermally stabilized prior to 3-Point bend testing. Heating and cooling was completed at a rate of 10° C. per minute. The full cycle thermograms for all wire sizes in their heat-treated conditions are provided in FIG. 32, mean values of transformation start and finish temperatures are provided in Table 13, temperature at the onset and end of the transformations, i.e., the extreme tails of the transformations, i.e., maxima and minima temperature of each transformation are provided in Table 14.

TABLE 13

Mean values of transformation start and finish temperatures from n = 3 specimen replicates for each size of wire. These values represent the temperatures derived using the conventional construction lines defining the 'straight' portion of the endotherms and exotherms approximating them to a net 'triangular' shape.

| Nominal Ø (mm) | $T^{M-R}$ [R'] | | $T^{R-M}$ [M] | | $T^{R-P}$ [A] | | $T^{P-R}$ [R] | |
|---|---|---|---|---|---|---|---|---|
| | $R'_s$ | $R'_f$ | $M_s$ | $M_f$ | $A_s$ | $A_f$ | $R_s$ | $R_f$ |
| 0.406 | −7.17 | 11.38 | −63.06 | −101.40 | 14.47 | 20.32 | 18.59 | 12.08 |
| 0.635 | −6.03 | 12.68 | −58.35 | −84.12 | 11.37 | 17.91 | 16.12 | 8.78 |
| 0.762 | −8.01 | 12.11 | −56.83 | −105.28 | 13.73 | 20.24 | 18.64 | 11.01 |
| 0.889 | −8.41 | 14.41 | −52.32 | −107.67 | 14.21 | 21.41 | 19.83 | 11.58 |

TABLE 14

Mean values of transformation start and finish temperatures from n = 3 specimen replicates for each size of wire, the Min. and Max. values are the minimum and maximum values from the pooled data, i.e., four sizes of wire and three replicates = 12 specimen replicates. These values represent the extreme tails of the transformations, i.e., maxima and minima temperature of each transformation.

| Nominal Ø (mm) | $T^{R-P}$ [A] | | $T^{P-R}$ [R] | | $T^{R-M}$ [M] | | $T^{M-R}$ [R'] | |
|---|---|---|---|---|---|---|---|---|
| | Trans Start | Trans Finish | Trans Start | Trans Finish | Trans Start | Trans Finish | Trans Start | Trans Finish* |
| 0.406 | 10.16 | 25.83 | 26.32 | 2.53 | −57.54 | −107.76 | −16.15 | 33.64 |
| 0.635 | 7.11 | 23.11 | 23.77 | 1.07 | −52.18 | −96.56 | −14.63 | 30.27 |
| 0.762 | 9.28 | 26.72 | 27.33 | 1.35 | −50.88 | −105.53 | −17.02 | 34.50 |
| 0.889 | 9.25 | 27.69 | 28.93 | 2.54 | −47.58 | −104.95 | −17.30 | 35.22 |
| Min. | 7.00 | 23.00 | 23.15 | 0.64 | −58.21 | −108.80 | −17.82 | 29.89 |
| Max. | 10.35 | 27.99 | 29.95 | 3.31 | −46.70 | −95.48 | −14.16 | 36.06 |

The thermal scheme provided in Table 15 was followed to stabilize austenite and R-phase during the 3-point bend tests.

TABLE 15

Temperature excursions scheme used to define the initial material condition. The red arrows designate heating, the blue cooling. In each case (A. & B.) the final temperature represents the test temperature.

| Initial Material Condition @ TEST T | Start Temp | Step 1 | Step 2 | Step 3 |
|---|---|---|---|---|
| A. Austenitic | Room Temp | → A Trans Finish | → R Trans Finish | → A Trans Finish |
| B. R-Phase | Room Temp | → A Trans Finish | → R Trans Finish | — |

Values of transformation target temperatures selected for the tests are provided in Table 16. These values are common values used for all wire sizes. Despite small differences in the transformation temperatures of the different sized wires, the transformations are sufficiently similar to allow a common set of cooling heat; schedules to achieve, the desired initial condition. The load is removed during the thermal ramps.

TABLE 16

Selected values of transformation start and finish temperatures. These values are common values used for all wire sizes. Despite small differences in the transformation temperatures of the different sized wires, the transformations are sufficiently similar to allow common cooling/heat schedules to achieve the desired initial condition.

| Initial Material Condition @ TEST T | Start Temp | Step 1 | Step 2 | Step 3 |
|---|---|---|---|---|
| A. Austenitic | Room Temp | → 35° C. | → ° C. | → 35° C. |
| B. R-Phase | Room Temp | → 35° C. | → ° C. | — |

The TA Instruments Q800 DMA is designed primarily for use in dynamic mode and not for de facto use as a miniature conventional mechanical tester. Due to software limitations, it was not feasible to run the quasi-static testing in the desired strain-controlled mode and a target force and load rate needed to be prescribed in place of target strains and strain rates. Since standard beam theory demands some linkage between force and displacement which cannot be known a priori, additional specimens representing "four corners" of the test matrix were run in advance of commencing the planned study. Preliminary moduli acquired from the 0.016" and 0.035" diameter wires tested over a 3.5 mm span plus 0.016" and 0.035" wire diameters tested over a 15 mm span were used to construct a relationship between modulus and L/d ratio. Curve fitting was used to derive an equation for the line of best fit, the equation was then used to crudely forecast the target force and load rates in an attempt to achieve a maximum engineering strain of 0.4% and an isothermal strain rate of 10-4s-1. The achieved strains and strain rates for each span plus wire diameter combinations are reported in Table 17. The maximum strain achieved for any wire diameter span combination in the austenitic state was <0.80%, all strain rates were <4.46×10-4/s.

The 3-point bend test was completed in accordance with Test Method 2, i.e., at 35° C. in force-controlled mode with the dynamic loading control deactivated, load was applied using a steady ramp up to a maximum force of 6N, Apparent flexural modulus was computed via the beam equation (Equation A1) using the gradient of the force-displacement plot plus appropriate. 2nd moment calculation for the circular cross-section wires (Equation 7A).

$$I_{(x_c)} = \frac{\pi}{4} r^4 \qquad \text{Equation 7A}$$

TABLE 17

Post-test (35° C.) assessment of maximum achieved strains and strain rates for each span plus wire diameter combination.

| | | Ø = 0.016" (0.407 mm) | | Ø = 0.025" (0.639 mm) | | Ø = 0.030" (0.764 mm) | | Ø = 0.035" (0.888 mm) | |
|---|---|---|---|---|---|---|---|---|---|
| Span (mm) | | Max. Strain % | Strain Rate ×10⁻⁴/s | Max. Strain % | Strain Rate ×10⁻⁴/s | Max. Strain % | Strain Rate ×10⁻⁴/s | Max. Strain % | Strain Rate ×10⁻⁴/s |
| 3.5 | | 0.70 | 3.07 | 0.71 | 3.28 | 0.56 | 2.03 | 0.44 | 1.37 |
| 5 | | 0.70 | 3.94 | 0.70 | 3.84 | 0.61 | 3.36 | 0.77 | 4.10 |

TABLE 17-continued

Post-test (35° C.) assessment of maximum achieved strains and strain rates for each span plus wire diameter combination.

| | Ø = 0.016" (0.407 mm) | | Ø = 0.025" (0.639 mm) | | Ø = 0.030" (0.764 mm) | | Ø = 0.035" (0.888 mm) | |
|---|---|---|---|---|---|---|---|---|
| Span (mm) | Max. Strain % | Strain Rate ×10$^{-4}$/s | Max. Strain % | Strain Rate ×10$^{-4}$/s | Max. Strain % | Strain Rate ×10$^{-4}$/s | Max. Strain % | Strain Rate ×10$^{-4}$/s |
| 10 | 0.66 | 3.55 | 0.79 | 4.10 | 0.65 | 3.59 | 0.73 | 4.09 |
| 15 | 0.63 | 1.78 | 0.78 | 4.46 | 0.63 | 3.56 | 0.67 | 2.47 |

5.3 Results—Method 5.

Figure 33:
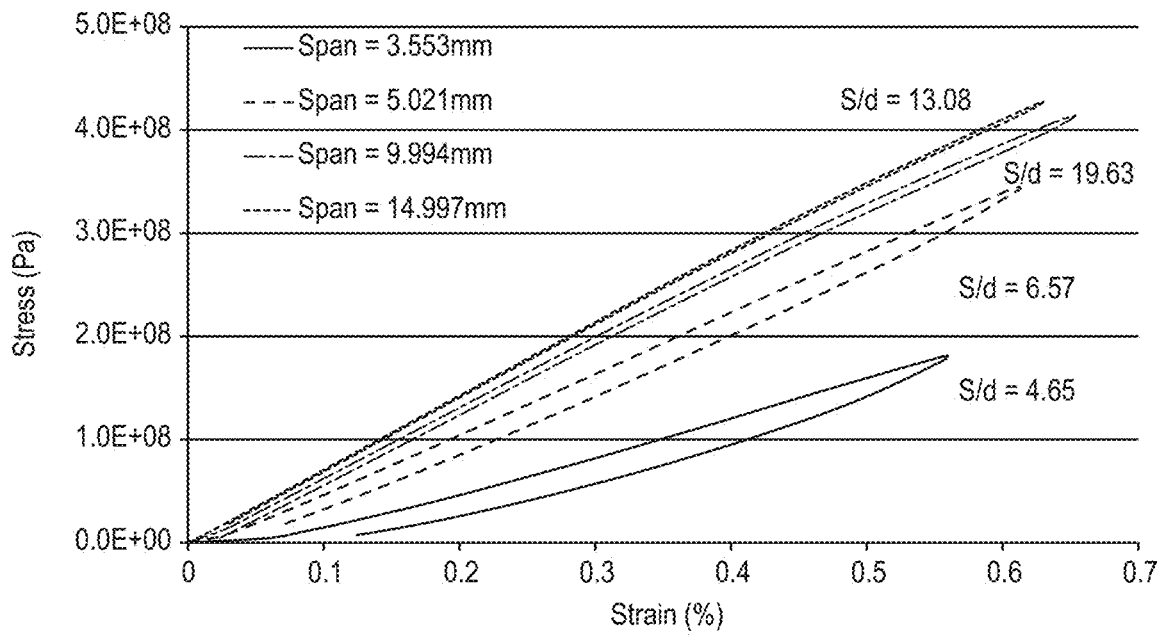
FIG. 33 is a plot of stress versus strain (%) during loading and unloading for 0.739 mm Ø NiTi wire specimens in 3-Point bending, at 35° C., four different span lengths (span lengths provided in Legend).

Stress versus strain (%) during loading and unloading for 0.739 mm Ø NiTi wire specimens in 3-Point bending at 35° C. for the four different span lengths are provided in FIG. 33, Note increasing hysteresis from the largest to smallest span coincident with an increasing shear-to-bend stress ratio. The span length to specimen depth is provided as a relative metric, smaller ratio equates with greater shear.

Figure 34:
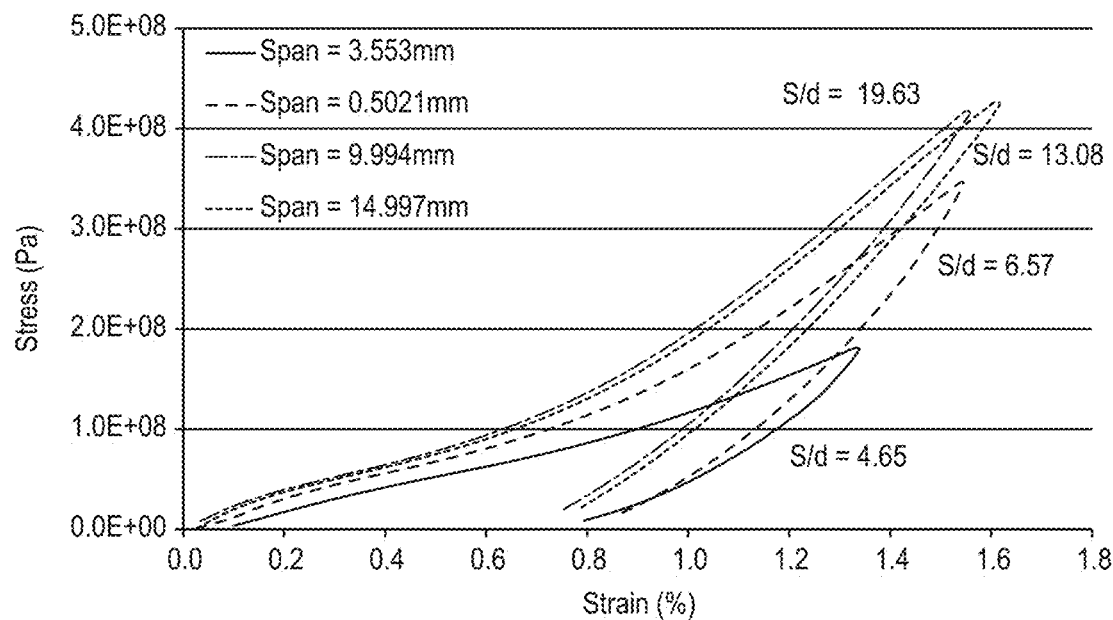
FIG. 34 is a plot of stress versus strain (%) during loading and unloading for 0.739 mm Ø NiTi wire specimens in 3-Point bending, at 0° C., four different span lengths (span lengths provided in Legend). R's=−8.01, R'f 12.11, As=13.73, and Af=20.24.

Stress versus strain (%) during loading and unloading for 0.739 mm Ø NiTi wire specimens in 3-Point bending at 0° C. for four different span lengths are provided in FIG. 34. Note increasing flattening equating with increased 'softness' from the largest to smallest span coincident with an increasing shear-to-bend stress ratio. The span length to specimen depth is provided as a relative metric, smaller ratio equates with greater shear. R's=−8.01, R'f 12.11, As=13.73, and Af=20.24.

Figure 35:
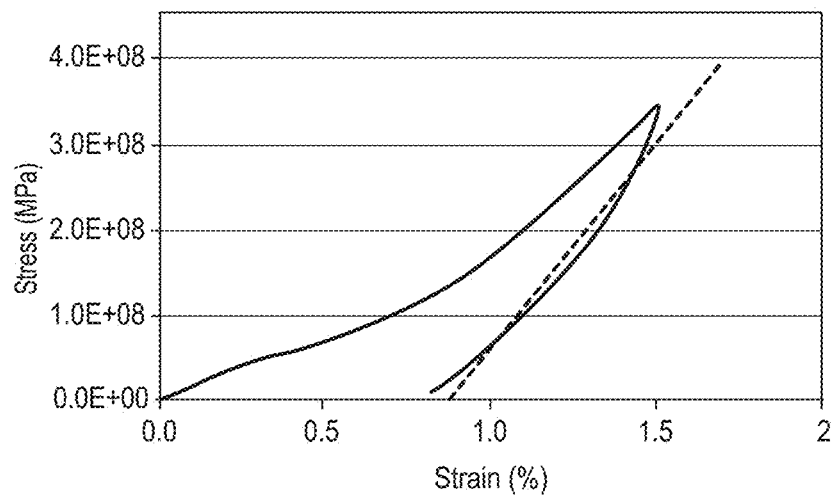
FIG. 35 is a plot of stress versus strain (%) during loading and unloading for 0.739 mm Ø NiTi wire specimens in 3-Point bending, at 0° C., span length of 5.021 mm. The dashed line is a simple regression (least squares) fit to the unloading data, the gradient of this line represents a crude secant modulus.

FIG. 35 shows the stress versus strain 04) during loading and unloading for 0.739 mm Ø NiTi wire specimens in 3-Point bending, at 0° C., span length of 5.021 mm. The dashed line is a simple regression (least squares) fit to the unloading data, note that all data points from the unloading data are used to plot the simple regression, the gradient of this line represents a crude secant modulus.

Table 18 provides the apparent flexural modulus during loading (Ea) at 3.5° C., and the secant modulus during unloading (ER secant) at 0° C. for all specimen diameter plus span combinations. All values were computed via the beam equation using the gradient of the force-displacement plot plus appropriate 2nd moment calculation for the circular cross-section wires.

TABLE 18

Apparent flexural modulus during loading (Ea) at 35° C., and the secant modulus during unloading (ER secant) at 0° C. for all specimen diameter plus span combinations.

| Wire Ø (mm) | Span Length (mm) | | | | | | | |
|---|---|---|---|---|---|---|---|---|
| | 3.553 | | 5.021 | | 9.994 | | 14.997 | |
| | $E_a$ | $E_R$ secant | $E_a$ | $E_R$ secant | $E_a$ | $E_R$ secant | $E_a$ | $E_R$ secant |
| 0.407 | 51.50 | 43.06 | 57.82 | 49.37 | 65.42 | 48.25 | 69.29 | 43.57 |
| 0.639 | 33.84 | 28.88 | 49.60 | 37.50 | 54.48 | 38.26 | 54.68 | 36.08 |
| 0.764 | 32.88 | 28.37 | 55.57 | 45.41 | 64.14 | 48.97 | 68.30 | 48.73 |
| 0.888 | 25.06 | 21.93 | 47.13 | 43.89 | 58.81 | 47.32 | 63.94 | 46.24 |

Figure 36:
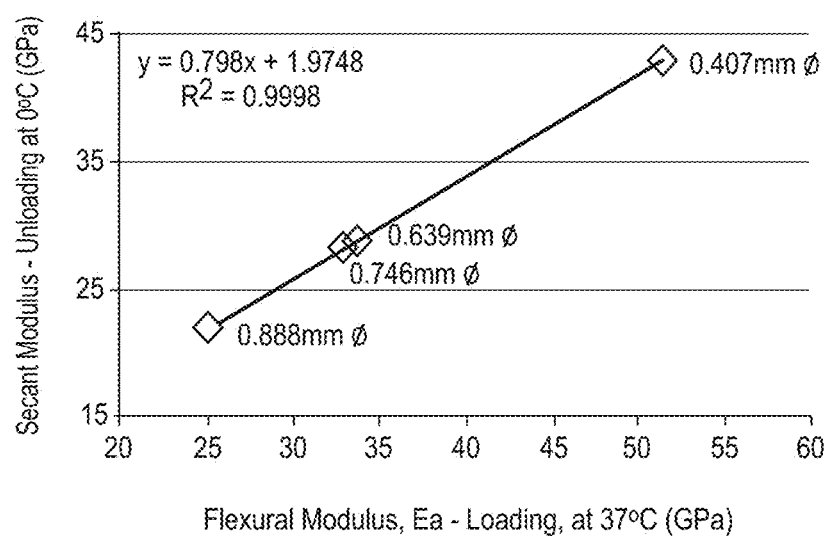
FIG. 36 is a plot of flexural modulus Ea (loading) at 35° C. and secant modulus ER (unloading) at 0° C. for all specimen diameters tested using the shortest span length (L=3.554 mm).

FIG. 36 shows good agreement between AFM (Ea) acquired during loading at 35° C. and ER secant at 0° C. for all specimen diameters tested using the shortest span length (L=3.554 mm) with an R2 of close to 1.0. It is speculated that the observed good agreement achieved at the smallest span for the pooled material diameters occurs because the increased shear acts to overwhelm any other differentiating factor, i.e., the magnitude of shear is sufficient to force a stress-induced transformation of the R-phase for all specimen diameters over the smallest span.

Figure 32:
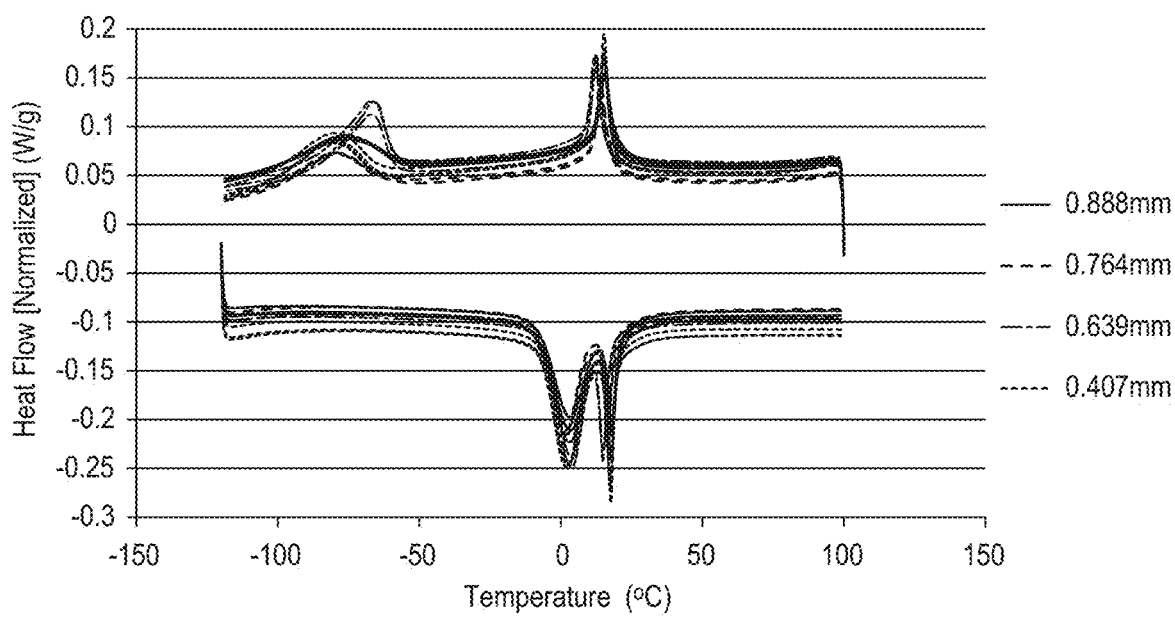
FIG. 32 is a DSC full cycle thermograms for all wire sizes in heat-treated condition, n=3 thermograms for each wire size. While some amount of vertical shift and horizontal spread in the latent heat and start and finish temperatures is typically observed amongst replicates in a given population, by inspection the there is good agreement of peak temperatures. It is noteworthy that the 0.639 mm wire thermograms (heating and cooling) differ significantly from the other three wire sizes.

FIGS. 37A-D show the apparent flexural modulus at 35° C. for each specimen tested, plots are provided for each wire diameter, pooling of different diameter wires on a common span length plot is avoided since the compositions and thermomechanical histories of the wires of a given diameter are not known and therefore they may possess different material properties, refer to FIG. 32.

Figure 38:
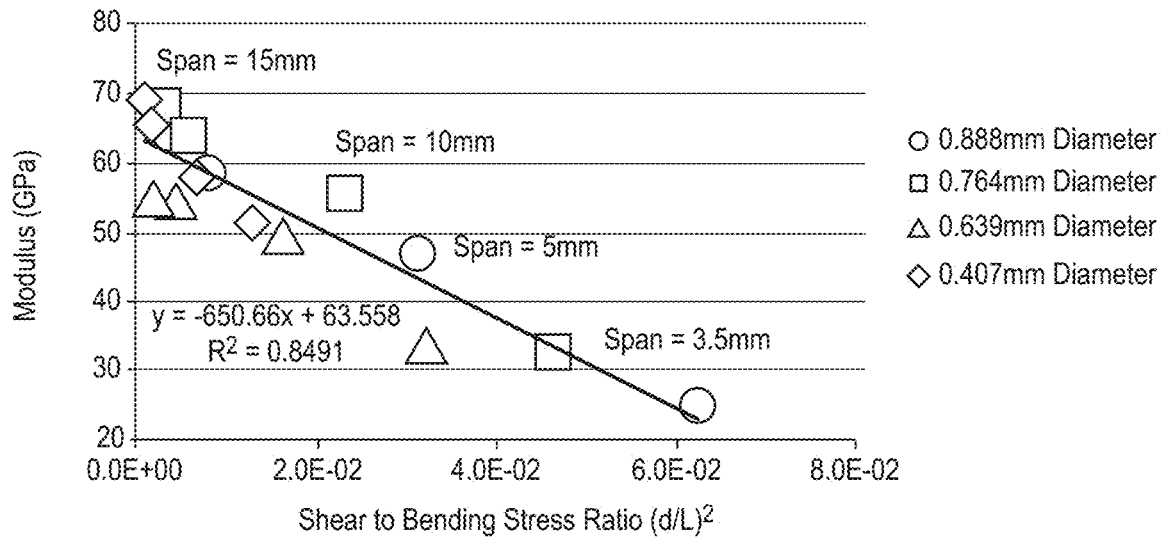
FIG. 38 is a plot of flexural modulus versus the shear to bending ratio for deflection of NiTi wire specimens (diameters provided) in 3-Point bending, at 35° C., four different span lengths (span lengths provided). The intercept value given by the simple regression line of best fit provides an estimate of the averaged flexural modulus for the pooled wire diameters at a hypothetical condition of zero shear.
Figure 39:
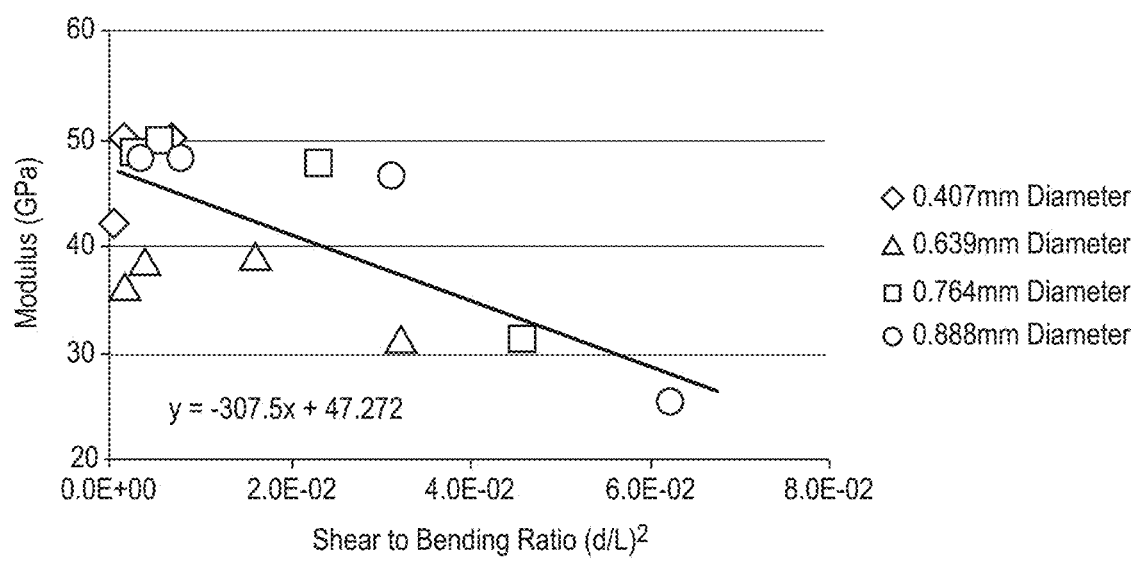
FIG. 39 is a plot of flexural secant modulus during unloading versus the shear to bending ratio for deflection of NiTi wire specimens (diameters provided) in 3-Point bending, at 0° C., four different span lengths (span lengths provided). The intercept value given by the simple regression line of best fit provides an estimate of the averaged flexural secant modulus during unloading modulus for the pooled wire diameters at a hypothetical condition of zero shear.
Figure 41A:
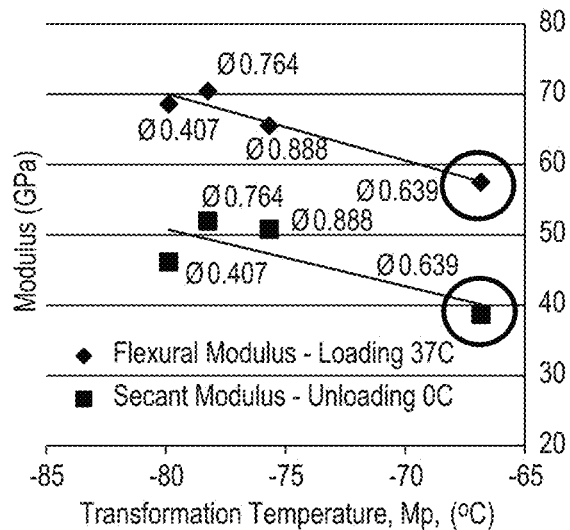
FIG. 41A is a plot of flexural modulus (loading at 37° C.) and secant modulus (unloading at 0° C.) both extrapolated to their hypothetical zero shear stress conditions versus Mp.
Figure 41B:
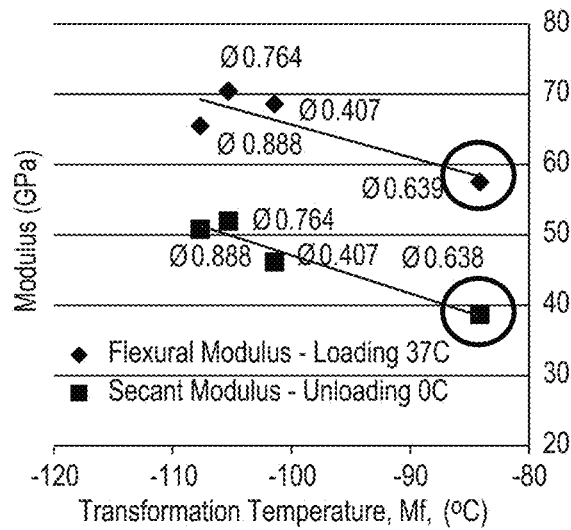
FIG. 41B is a plot of flexural modulus (loading at 37° C.) and secant modulus (unloading at 0° C.) both extrapolated to their hypothetical zero shear stress conditions versus Mf.
Figure 41C:
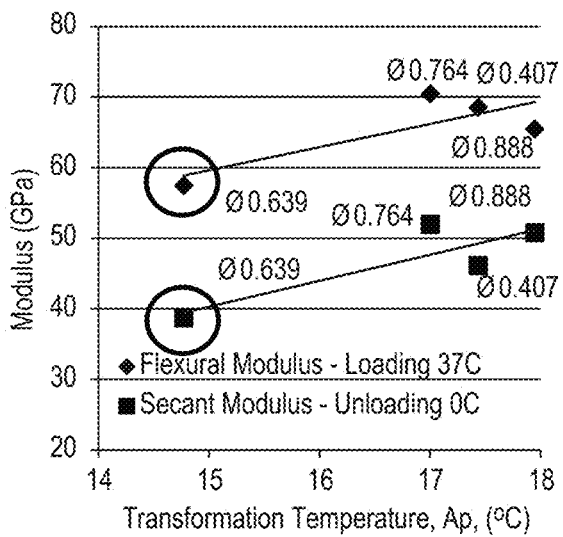
FIG. 41C is a plot of flexural modulus (loading at 37° C.) and secant modulus (unloading at 0° C.) both extrapolated to their hypothetical zero shear stress conditions versus Ap.
Figure 41D:
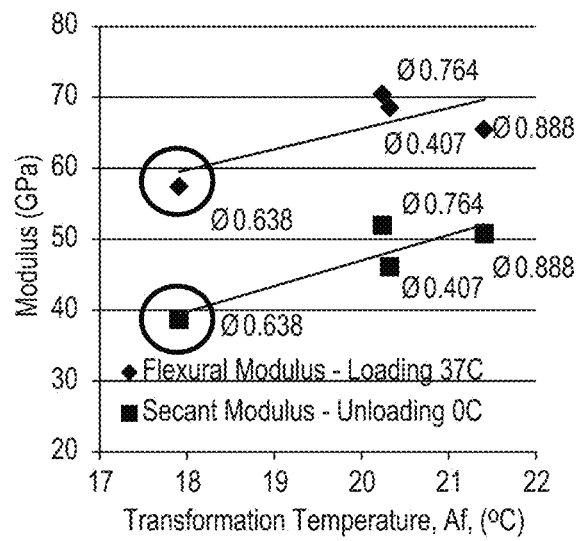
FIG. 41D is a plot of flexural modulus (loading at 37° C.) and secant modulus (unloading at 0° C.) both extrapolated to their hypothetical zero shear stress conditions versus Af.
Figure 42A:
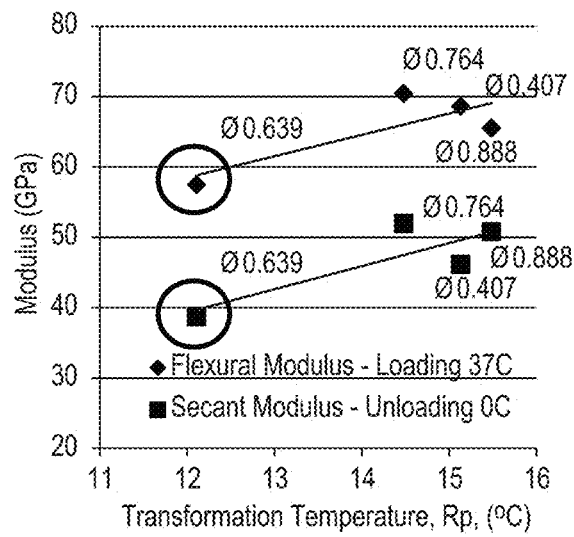
FIG. 42A is a plot of flexural modulus (loading at 37° C.) and secant modulus (unloading at 0° C.) both extrapolated to their hypothetical zero shear stress conditions versus Rp.
Figure 42B:
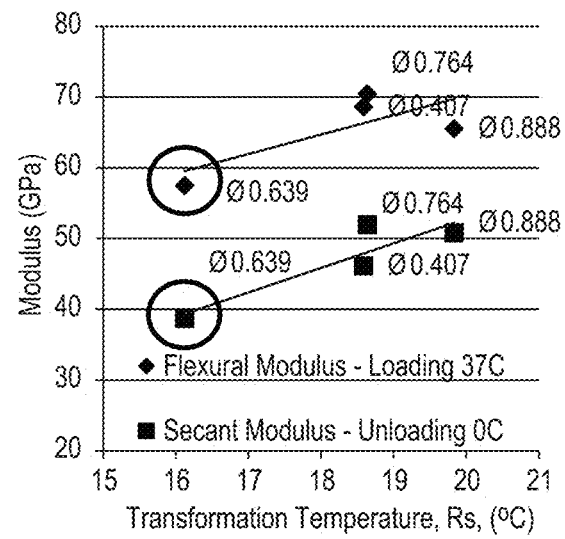
FIG. 42B is a plot of flexural modulus (loading at 37° C.) and secant modulus (unloading at 0° C.) both extrapolated to their hypothetical zero shear stress conditions versus Rs.
Figure 42C:
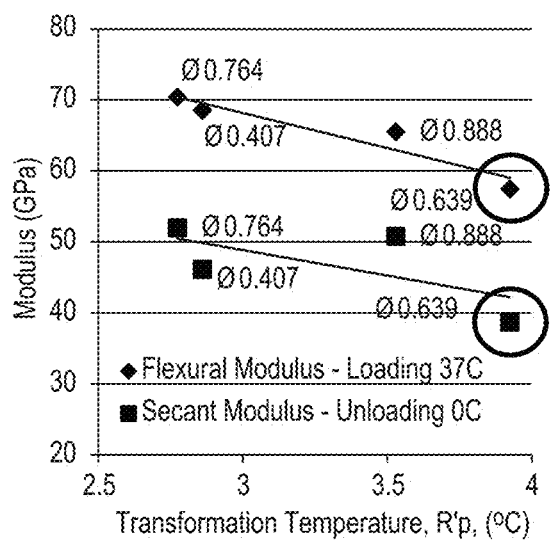
FIG. 42C is a plot of flexural modulus (loading at 37° C.) and secant modulus (unloading at 0° C.) both extrapolated to their hypothetical zero shear stress conditions versus R'p.
Figure 42D:
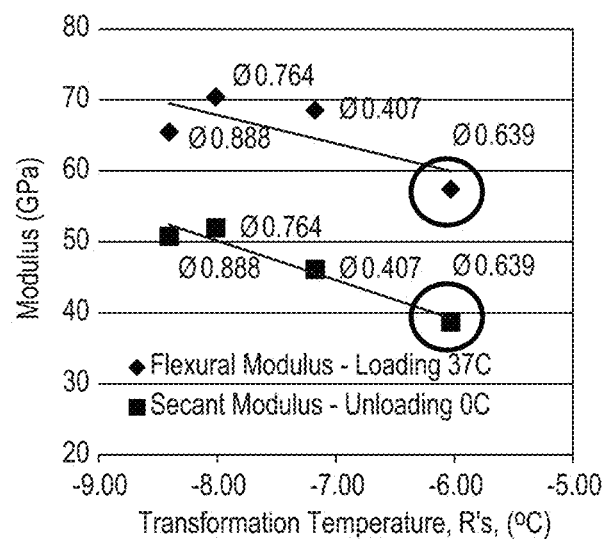
FIG. 42D is a plot of flexural modulus (loading at 37° C.) and secant modulus (unloading at 0° C.) both extrapolated to their hypothetical zero shear stress conditions versus R's.

A simple regression (least squares) line of best fit is provided for each wire size with R2 values typically greater than 0.95 (FIGS. 37A-D), in each case the intercept on the x-axis represents an extrapolated hypothetical condition of zero shear stress contribution. For each wire size it is hypothesized that the intercept value represents close to a 'true' flexural modulus of the austenite phase. The pooled data from FIGS. 24a-24d is plotted to yield an average intercept value of approximately 64 GPa at 37° C. (refer to FIG. 38). An analogous pooled data plot plus averaged modulus of approximately 47 GPa is also provided for the secant modulus observed during unloading for specimens tested at a temperature of 0° C., refer to FIG. 39. It is noteworthy that this value (47 GPa) is very close to the average value 44 GPa quoted by Kusy and Stush (Ref. 10) from their survey of flexural testing completed for orthodontic applications. For the smallest 0.407 mm Ø wire tested across the largest span 14.997 mm (L/d 36), and for the 0.764 mm Ø wire tested across the same span length of 14.997 mm (L/d 20) the moduli of 69 and 68 GPa respectively are close to those values achieved via standard axial tensile testing of larger specimens using a clip-on strain gauges, i.e., 68-72 GPa.

FIGS. 40A-D provide the flexural moduli observed during loading at 37° C. and secant moduli observed during unloading at 0° C. are plotted together for each wire diameter as a function of span length. By inspection the moduli at 0° C. and 37° C. follow very similar trends, although it is recognized that secant moduli established from the none-linear unloading data are crude, good agreement of ER with AFM (Ea) demonstrates that the R-phase is implicated in the observed AFMs.

Figure 37A:
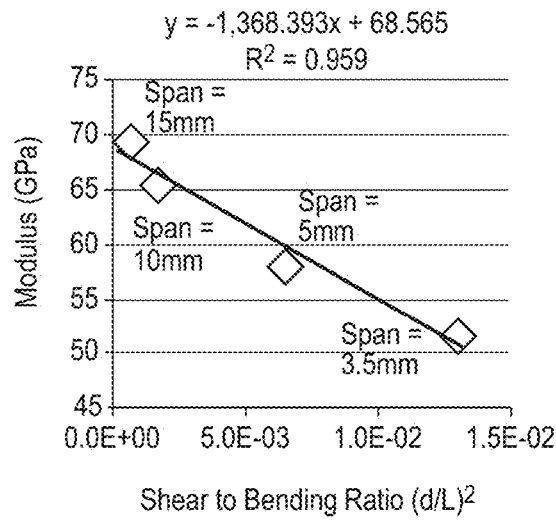
FIG. 37A is a plot of flexural modulus vs. shear to bending ratio for 0.407 mm Ø NiTi wire in 3-Point Bend at 35° C.
Figure 37B:
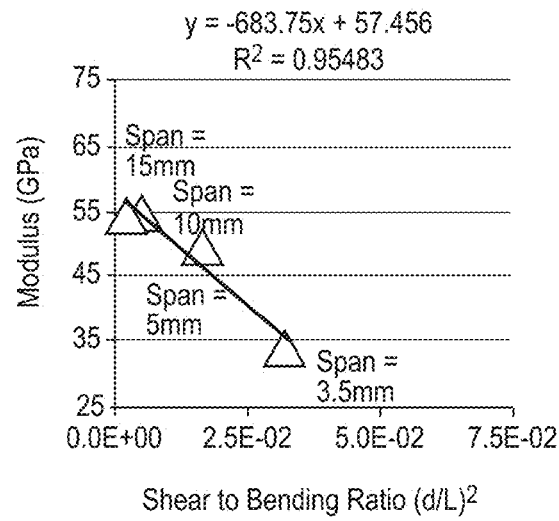
FIG. 37B is a plot of flexural modulus vs. shear to bending ratio for 0.639 mm Ø NiTi wire in 3-Point Bend at 35° C.
Figure 37C:
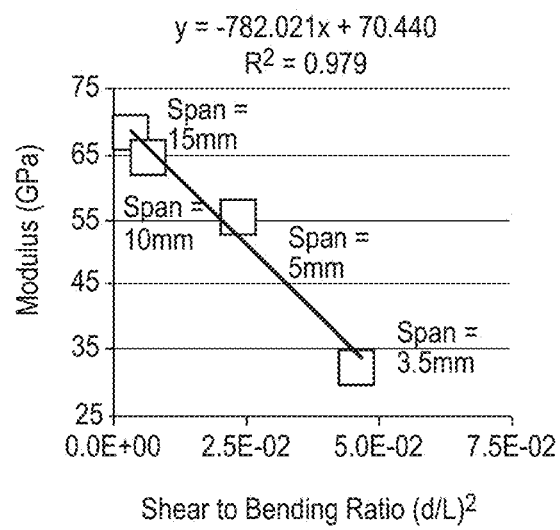
FIG. 37C is a plot of flexural modulus vs. shear to bending ratio for 0.764 mm Ø NiTi wire in 3-Point Bend at 35° C.
Figure 37D:
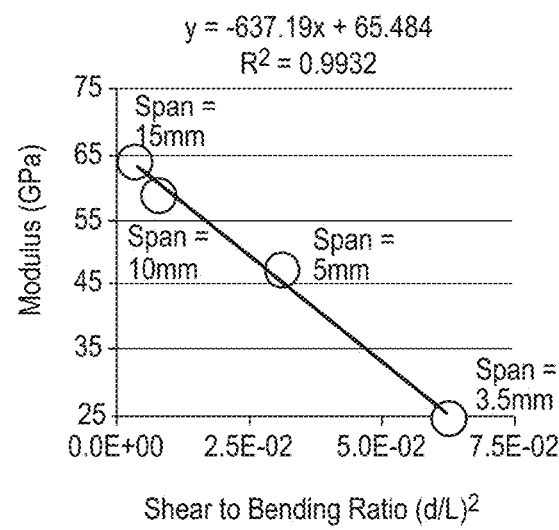
FIG. 37D is a plot of flexural modulus vs. shear to bending ratio for 0.888 mm Ø NiTi wire in 3-Point Bend at 35° C.

By inspection of Table 18 and FIG. 32, by comparison of FIG. 37C with FIGS. 37A, B, and D, and by comparison of FIGS. 40A-D, the 0.639 mm Ø wire exhibits slightly different transformation behaviour and different mechanical behaviour versus specimens of the other three wire diameters. The following plots, viz., FIGS. 41A-D and FIGS. 42A-D provide plots the flexural modulus (loading at 37° C.) and secant modulus (unloading at 0° C.) both extrapolated to their hypothetical zero shear stress conditions versus various transformation temperatures to highlight possible correlations between the anomalous behaviour of the 0.639 mm Ø wire and selected parameters. The 0.639 mm Ø wire is ringed in green on the following FIGS. 41A-D, and FIGS. 42A-D.

6.0 Three-Point Bend Testing of Heat-Treated 0.764 mm Ø Round Wire Specimens 6.1 Introduction The testing reported in Section 5 was completed on four sizes of round wire specimens all possessing close to near equiatomic Ni and Ti, with each wire size being subjected to a common heat-treatment, all specimens possessed similar transformation properties. In the following testing the relative propensity for shear softening during 3-Point bend Testing at a test temperature just above Af is determined as function of six (6) different heat-treatments on a common size of wire (0.764 mm Ø). The heat-treatments are intended to modify the microstructure via precipitation of a nickel-rich phase and in the case of the solutionized specimens, via a combination of dissolution of Ni rich precipitates and thermal annihilation of dislocations. Manipulation of the microstructure results in different transformation sequences, latent heats and transformation temperatures which are readily identified via DSC which can then be correlated with apparent flexural modulus. Two span lengths were selected, 5.021 mm and 14.997; bending the specimens over the shorter span length (S/L ratio=6.57) results in threefold (3λ) greater shear than the longer span length (S/L ratio=19.63).

6.2 Test Method 6

Figure 43:
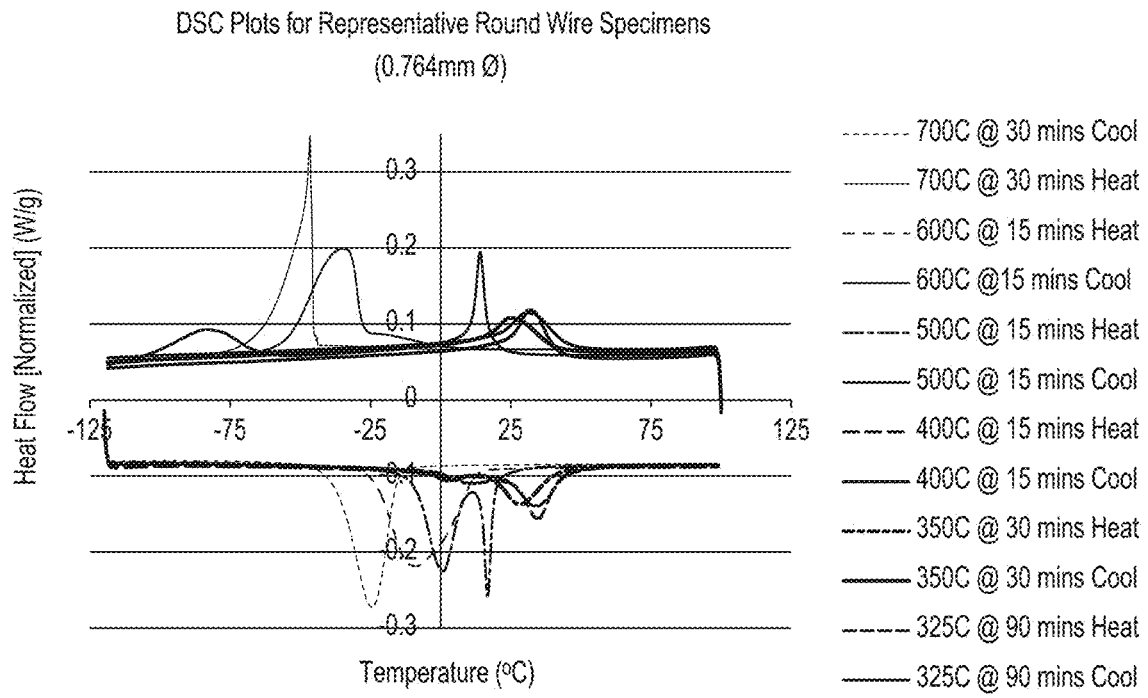
FIG. 43 is a plot of a full heat/cool cycle DSC thermograms for specimens produced from a fixed wire diameter of 0.764 mm heat-treated per the time and temperatures provided in the legend.

As discussed in Section 5, previous studies (e.g., the study reported in Section 7) have shown that phase transformations may commence and continue to completion at sub-stantially different temperatures than those indicated by the standard start/finish temperature metric which is derived using simple triangular-like tangent-line/intercept constructions on DSC thermogram plots. On the basis of this knowledge the true initiation and completion points of the transformations in the tails of the exo- and endotherms were identified using DSC. This was done to ensure appropriate thermal stabilization of the austenite phase prior to 3-Point bend testing. Representative full cycle thermograms for 0.764 mm Ø wire possessing a variety of heat treatments are provided in FIG. 30. The transformations for all heat treatments with the exception of the solutionized specimens (600° C. for 15 mins) exhibit a forward A→R→M transformation sequence on cooling and a reverse M→R→A transformation on heating. The M phase is absent except on the 400° C., 600° C. and 700° C. specimens, it was assumed that the heat treatment has stabilized the austenite phase thereby demanding more undercooling than was provided by the DSC at −125° C., however, some M phase transformation must have necessarily occurred, see note immediately following FIG. 43. The Mean values of transformation start and finish temperatures are provided in Table 19, temperature at the onset and end of the transformations, i.e., the extreme tails of the transformations, i.e., maxima and minima temperature of each transformation are provided in Table 20.

TABLE 19

Mean values of transformation start and finish temperatures from n = 5 specimen replicates for each heat treatment (fixed wire diameter = 0.764 mm). These values represent the temperatures derived using the conventional construction lines defining the 'straight' portion of the endotherms and exotherms approximating them to a net 'triangular' shape.

| Temp (° C.) | Time (s) | $T^{R-P}$ [A] | | $T^{P-R}$ [R] | | $T^{R-M}$ [M] | | $T^{M-R}$ [R'] | |
|---|---|---|---|---|---|---|---|---|---|
| | | $A_s$ | $A_f$ | $R_s$ | $R_f$ | $M_s$ | $M_f$ | $R'_s$ | $R'_f$ |
| 325 | 90 | 21.9 | 44.8 | 4404 | 19.0 | — | — | −2.4 | 8.2 |
| 350 | 30 | 15.6 | 39.8 | 39.8 | 12.3 | — | — | −7.5 | 4.2 |
| 400 | 15 | 26.6 | 42.8 | 41.7 | 24.2 | — | — | −1.2 | 19.1 |
| 500 | 15 | 13.6 | 19.7 | 17.7 | 10.8 | −62.4 | −106.8 | −9.4 | 8.7 |
| 600 | 15 | −23.7 | 12.3 | 2.1 | — | −27.4 | −54.7 | — | 8.3 |
| 700 | 30 | −37.5 | −15.6 | −2.5 | — | −45.1 | −54.4 | — | −3.3 |

NOTE:
The italicized values of Rs and R'f were derived from partial cycle DSC, for both the 600° C. and 700° C. populations the forward and reverse R-phase transformations were weak and diffuse rendering these values (italicized) less reliable.

TABLE 20

Mean values of transformation start and finish temperatures from n = 5 specimen replicates for each heat treatment (fixed wire diameter = 0.764 mm). These values represent the extreme tails of the transformations, i.e., maxima and minima temperature of each transformation.

| Temp (° C.) | Time (s) | $T^{R-P}$ [A] | | $T^{P-R}$ [R] | | $T^{R-M}$ [M] | | $T^{M-R}$ [R'] | |
|---|---|---|---|---|---|---|---|---|---|
| | | Trans Start | Trans Finish | Trans Start | Trans Finish | Trans Start | Trans Finish | Trans Start | Trans Finish |
| 325 | 90 | 18.8 | 48.6 | 51.8 | 8.9 | — | — | −4.3 | 9.8 |
| 350 | 30 | 12.4 | 44.0 | 48.2 | 0.9 | — | — | −9.6 | 5.8 |
| 400 | 15 | 22.1 | 49.1 | 49.6 | 13.0 | — | — | −3.6 | 19.4 |
| 500 | 15 | 8.2 | 23.8 | 24.9 | 4.3 | −111.2 | −54.1 | −16.8 | 11.5 |
| 600 | 15 | −43.8 | 18.8 | — | — | 10.0 | −87.5 | — | — |
| 700 | 30 | −47.3 | −11.3 | — | — | −42.6 | −74.9 | — | — |

The presence of R' in all specimens indicates that some transformation into the martensite phase must have necessarily occurred during the cooling step. Example: R-phase is observed as a small 'hump' to the side of the 600° C. specimen VI-phase transformation, upon heating the R'-phase occurs simultaneously with the austenite transformation but is readily separated via partial cycle DSC.

The thermal scheme provided in Table 21 was followed to thermally stabilize the austenite phase during the 3-point bend tests, the temperature cycle is intend to hold the specimen at a temperature above which the R-phase would preferentially form in the stress-free condition. The objective is to ascertain the relative ease of shear inducing the R-phase transformation as a function of transformation sequence and temperature arising from the various heat treatments. For example, it is assumed that a correctly solutionized specimen initially possesses zero R-phase, therefore it is further assumed that it will also possess the highest apparent modulus approaching that anticipated for B2 austenite NiTi (70 GPa) both at the longer span length of 14.9971 m and at an extrapolated shear-to-bend ratio close to zero [Although the shorter span length might be incapable of promoting a shear-induced softening of the R-phase, depression of the neutral axis during bending resulting from the shear may result in a small artificial softening elect due to a breakdown in linear elastic beam theory]. Note that relative plateau stresses of the specimens are not considered in this stud although it is recognized that they will be different. It is the intention of the 3-Point bend Study to remain in the "elastic" proportional region of the stress-strain curve in each case and where possible avoid any excursions onto the loading plateau.

TABLE 21

Temperature excursions scheme used to define the initial material condition (austenite). The red arrows designate heating, the blue cooling. The final temperature (Step 3) represents the test temperature.

| Initial Material Condition @ TEST T | Start Temp | Step 1 | Step 2 | Step 3 |
|---|---|---|---|---|
| Target = Austenitic | Room Temp | → A Trans Finish | → R Trans Finish | → A Trans Finish |

NOTE: For appropriately solutionized specimens the R-phase should be absent and therefore only two thermal Steps are required to take the specimens from room temperature up to the target thermally-stabilized austenite condition.

Values of transformation target temperatures selected tier the tests are provided in Table 22. These values are different for each beat treatment with the exception of 325° C. and 400° C. heat treatments which are identical (but purely coincidental). Although a heat treatment of 325° C. for 90 minutes results in a very similar transformation pattern as that resulting from a 350° C. 30 minutes duration heat treatment, the tails of the transformation are slightly different therefore raising the possibility for differences in AFM, accordingly, despite similarities, both were maintained for testing.

TABLE 22

Selected values of transformation start and finish temperatures for performing the tests. The intention of the thermal cycling is to ensure that transformations are fully exhausted in all cases and that the 3-Point bend Tests are completed with specimens in their fully transformed austenitic condition [A total of four additional specimens were tested at a test temperature = Af, results are provided in Table 23].

| Heat Treatment | Start Temp | Step 1 | Step 2 | Step 3 |
|---|---|---|---|---|
| 325 | Room Temp | → 55° C. | → 0° C. | → 60° C. |
| 350 | Room Temp | → 55° C. | → −10° C. | → 60° C. |
| 400 | Room Temp | → 55° C. | → 0° C. | → 60° C. |
| 500 | Room Temp | → 30° C. | → −5° C. | → 35° C. |

TABLE 22-continued

Selected values of transformation start and finish temperatures for performing the tests. The intention of the thermal cycling is to ensure that transformations are fully exhausted in all cases and that the 3-Point bend Tests are completed with specimens in their fully transformed austenitic condition [A total of four additional specimens were tested at a test temperature = Af, results are provided in Table 23].

| Heat Treatment | Start Temp | Step 1 | Step 2 | Step 3 |
|---|---|---|---|---|
| 600 | Room Temp | → 25° C. | → −50° C. | → 30° C. |
| 700 | Room Temp | → −75° C. | → −5° C. | — |

Initial inspection of DSC data for the 700° C. specimens did not reveal any obvious signs of R-phase transformation. Therefore, the thermal scheme for those specimens was prescribed as a two Step process.

Heating and cooling per Table 22 were completed at a rate of 10° C. per minute. Testing was completed using span lengths of 5 mm and 15 mm using a TA Instruments Q800 DMA. The Q800 is designed primarily for use in dynamic mode and not as a miniature conventional mechanical tester. As discussed in Section 5, due to software limitations it is not feasible to run the quasi-static testing in the desired strain-controlled mode, instead, a target force and load rate need to be prescribed in place of target strains and strain rates. Since beam theory demands some linkage between force and displacement which cannot be known a priori, and because the specimens are all heat-treated differently and therefore because it is anticipated that all five populations will behave differently under load, moduli can't be predicted without running tests on specimens from all five populations. If tests were completed on all populations, the loads would still require real-time adjustment to avoid excursions onto the loading plateau which is also likely to be different for each population assuming a Clausius Clapeyron relationship based on Af temperatures, refer to Table 19. Some approximations and explicit assumptions were made to expedite testing and facilitate progress.

It is anticipated that the stress induced martensite (SIM) plateau occurs somewhere around 1.0% strain and that the macroscopic manifestation of R-phase if present will be observed to commence at a strain >0.7%. To preserve specimens and excessive pre-testing characterization, a low modulus was assumed for all specimens regardless of heat-treatment. The lowest secant modulus of approximately 30 GPa as observed for the thermally stabilized R-phase in the former study described in Section 5 was adopted across all populations. In doing so, it was anticipated that since there is a high probability that all specimens tested above their Af will likely be stiffer than specimens with stabilized R-phase—because they are being tested above the tail-end of the austenite transformation, then the likelihood of stress-inducing any martensite phase via either A-to-M or R-to-M transformation is low. The reason why this selection of a common modulus for all specimens remains valid is because the intention of the test is to remain in the elastic regime and collect sufficient Force versus Displacement data with which to deduce modulus, via the beam equation. So long as there are sufficient data points and no excursion on to the plateau or into the macro-R-phase region immediately preceding the plateau, the modulus derivation will be reliable and useful for comparative analysis purposes. It was hypothesized that a target strain of 0.6% would avoid macroscopic manifestation of R-phase softening (if it has the propensity to occur), i.e. staying below 0.6% strain would avoid that characteristic bending towards the onset of the plateau while still capturing its more clandestine and insidious contributions lower in the so-called "elastic region". Stress-induced R-phase contributions may occur at stresses as low as 5 MPa and therefore remain undetected.

Using the beam equation, stress in the 3-Pt. Bend Test is given as $$\sigma = \frac{FL}{\pi r^3} \qquad \text{Equation 8A}$$

Since $E=\sigma/\varepsilon$ and by simple rearrangement $\sigma=E\times\varepsilon$, given a fixed modulus (30 GPa), and a fixed target strain=0.006 (0.6%) it is possible to solve for force (N) for the two span lengths.

$$F=(E\times\varepsilon\times\pi\times r^3)/L \qquad \text{Equation 9A}$$

Although a common isothermal strain rate of $10{-}4s{-}1$ is preferred, some deviation from this target is anticipated given the necessary approximation of elastic modulus. Apparent flexural modulus will be computed via the beam equation (Equation A1) using the gradient of the force-displacement plot plus appropriate 2nd moment calculation for the circular cross-section wires (Equation 7B).

6.3 Results Test Method 6

TABLE 23

Summary results for 0.764 mm wire specimens possessing a variety of heat treatments (temperatures and times), specimen replicates from each population were tested over tow span lengths 5 mm and 15 mm using quasi-static DMA, apparent flexural modulus values (Ea) were computed via linear elastic beam equations using force and displacement data. The two end columns provide an indication of proximity of the selected test temperature to the end of the reverse R'-phase transformation (R'f) and the start of the forward R-phase transformation (Rs). For each heat treatment condition, the test temperature represents the very tail end of the austenite reverse transformation; i.e., T > Af. In all cases, some M-phase transformation was present the DSC cooling scan. Absence of values for Ms and Mf indicates that the M-phase was diffuse such that quantitative evaluation was not possible.

| Temp (C.) | Time (s) | Span (mm) | Ea (GPa) | Repl (n) | As | Af | Rs | Rf | Ms | Mf | R's | R'f | End aus. | End R' | Test T | TT-R' end | TT-Rs |
|---|---|---|---|---|---|---|---|---|---|---|---|---|---|---|---|---|---|
| | | | | | | | | | Degrees Centigrade | | | | | | | | |
| 325 | 90 | 5 | 65 | 2 | 21.9 | 44.8 | 44.4 | 19.0 | — | — | -2.4 | 8.2 | 48.6 | 9.8 | 60 | 50.2 | 15.6 |
| 325 | 90 | 15 | 77 | 3 | 21.9 | 44.8 | 44.4 | 19.0 | — | — | -2.4 | 8.2 | 48.6 | 9.8 | 60 | 50.2 | 15.6 |
| 350 | 30 | 5 | 67 | 3 | 15.6 | 39.8 | 39.8 | 12.3 | — | — | -7.5 | 4.2 | 44 | 5.8 | 60 | 54.2 | 20.2 |
| 350 | 30 | 15 | 78 | 3 | 15.6 | 39.8 | 39.8 | 12.3 | — | — | -7.5 | 4.2 | 44 | 5.8 | 60 | 54.2 | 20.2 |
| 400 | 15 | 5 | 63 | 3 | 26.6 | 42.8 | 41.7 | 24.2 | — | — | -1.2 | 19.1 | 49.1 | 19.4 | 60 | 40.6 | 18.3 |
| 400 | 15 | 15 | 79 | 2 | 26.6 | 42.8 | 41.7 | 24.2 | — | — | -1.2 | 19.1 | 49.1 | 19.4 | 60 | 40.6 | 18.3 |
| 500 | 15 | 5 | 56 | 2 | 13.6 | 19.7 | 17.7 | 10.8 | -62.4 | -106.8 | -9.4 | 8.7 | 23.8 | 11.5 | 35 | 23.5 | 17.3 |
| 500 | 15 | 15 | 71 | 2 | 13.6 | 19.7 | 17.7 | 10.8 | -62.4 | -106.8 | -9.4 | 8.7 | 23.8 | 11.5 | 35 | 23.5 | 17.3 |
| 600 | 15 | 5 | 60 | 2 | -23.7 | 12.3 | 2 | — | -27.4 | -54.7 | — | 9 | 18.8 | 18 | 30 | 12 | 28 |
| 600 | 15 | 15 | 78 | 3 | -23.7 | 12.3 | 2 | — | -27.4 | -54.7 | — | 9 | 18.8 | 18 | 30 | 12 | 28 |
| 700 | 30 | 5 | 54 | 3 | -37.5 | -15.6 | -8 | — | -45.1 | -54.4 | — | -1 | -11.3 | 5 | -5 | 10 | 3 |
| 700 | 30 | 15 | 74 | 3 | -37.5 | -15.6 | -8 | — | -45.1 | -54.4 | — | -1 | -11.3 | 5 | -5 | 10 | 3 |

TABLE 24

Summary results for 0.764 mm wire specimens possessing a variety of heat treatments (temperatures and times) tested at lower test temperature T = Af than the specimens tested in the main study (Tables 21 and 22). The two end columns provide an indication of proximity of the test temperature relative to the end of the reverse R'-phase transformation (R'f) and the start of the forward R-phase transformation (Rs). In all cases, M-phase was present. The absence of values for Ms and Mf indicates that the M-phase was diffuse such that quantitative evaluation was not possible.

| Temp (C.) | Time (s) | Span (mm) | Ea (GPa) | Repl (n) | As | Af | Rs | Rf | Ms | Mf | R's | R'f | End aus. | End R' | Test T | TT-R' end | TT-Rs |
|---|---|---|---|---|---|---|---|---|---|---|---|---|---|---|---|---|---|
| | | | | | | | | | Degrees Centigrade | | | | | | | | |
| 325 | 90 | 5 | 56 | 1 | 21.9 | 44.8 | 44.4 | 19.0 | — | — | -2.4 | 8.2 | 48.6 | 9.8 | 44.8 | 35.0 | 0.4 |
| 350 | 30 | 5 | 55 | 1 | 15.6 | 39.8 | 39.8 | 12.3 | — | — | -7.5 | 4.2 | 44.0 | 5.8 | 39.8 | 34.0 | 0.0 |
| 400 | 15 | 5 | 51 | 1 | 26.6 | 42.8 | 41.7 | 24.2 | — | — | -1.2 | 19.1 | 49.1 | 19.4 | 42.8 | 23.4 | 1.1 |
| 400 | 15 | 15 | 61 | 1 | 26.6 | 42.8 | 41.7 | 27.2 | | | -1.2 | 19.1 | 49.1 | 19.4 | 42.8 | 23.4 | 1.1 |

TABLE 25

Comparison of results for 0.764 mm wire specimens possessing a variety of heat treatments (temperatures and times) at two test temperatures, TT > Af and TT = Af . The two end columns provide an indication of proximity to the very end of the reverse transformation and the start of the forward transformation relative to test temperature. The Δ Ea values are the differences between the apparent elastic modulus determined at the two test temperatures, the Δ T.T. values are the differences in test temperatures. In all cases, M-phase was present, absence of values for Ms and Mf indicates that the M-phase was diffuse such that quantitative evaluation was not possible.

| Temp (C.) | Time (s) | Span (mm) | Ea (GPa) | Repl (n) | As | Af | Rs | Rf | Ms | Mf | R's | R'f | End aus. | End R' | Test T | TT-R' end | TT-Rs |
|---|---|---|---|---|---|---|---|---|---|---|---|---|---|---|---|---|---|
|  |  |  |  |  |  |  |  |  | Degrees Cenigrade |  |  |  |  |  |  |  |  |
| 325 | 90 | 5 | 65 | 2 | 21.9 | 44.8 | 44.4 | 19.0 | — | — | -2.4 | 8.2 | 9.8 | 60 | 50.2 | 50.2 | 15.6 |
| 325 | 90 | 5 | 56 | 1 | 21.9 | 44.8 | 44.4 | 19.0 | — | — | -2.4 | 8.2 | 9.8 | 44.8 | 35.0 | 35.0 | 0.4 |
|  |  | Δ Ea | 14% |  |  |  |  |  |  |  |  |  | Δ T.T | 15 C. |  |  |  |
| 350 | 30 | 5 | 67 | 3 | 15.6 | 39.8 | 39.8 | 12.3 | — | — | -7.5 | 4.2 | 5.8 | 60 | 54.2 | 54.2 | 20.2 |
| 350 | 30 | 5 | 55 | 1 | 15.6 | 39.8 | 39.8 | 12.3 | — | — | -7.5 | 4.2 | 5.8 | 39.8 | 34.0 | 34.0 | 0.0 |
|  |  | Δ Ea | 18% |  |  |  |  |  |  |  |  |  | Δ T.T | 20 C. |  |  |  |
| 400 | 15 | 5 | 63 | 3 | 26.6 | 42.8 | 41.7 | 24.2 | — | — | -1.2 | 19.1 | 19.4 | 60 | 40.6 | 40.6 | 18.3 |
| 400 | 15 | 5 | 51 | 1 | 26.6 | 42.8 | 41.7 | 24.2 | — | — | -1.2 | 19.1 | 19.4 | 42.8 | 23.4 | 23.4 | 1.1 |
|  |  | Δ Ea | 19% |  |  |  |  |  |  |  |  |  | Δ T.T | 17 C. |  |  |  |
| 400 | 15 | 15 | 79 | 2 | 26.6 | 42.8 | 41.7 | 24.2 | — | — | -1.2 | 19.1 | 19.4 | 60 | 40.6 | 40.6 | 18.3 |
| 400 | 15 | 15 | 61 | 1 | 26.6 | 42.8 | 41.7 | 24.2 | — | — | -1.2 | 19.1 | 19.4 | 42.8 | 23.4 | 23.4 | 1.1 |
|  |  | Δ Ea | 22% |  |  |  |  |  |  |  |  |  | Δ T.T | 17 C. |  |  |  |

Figure 44:
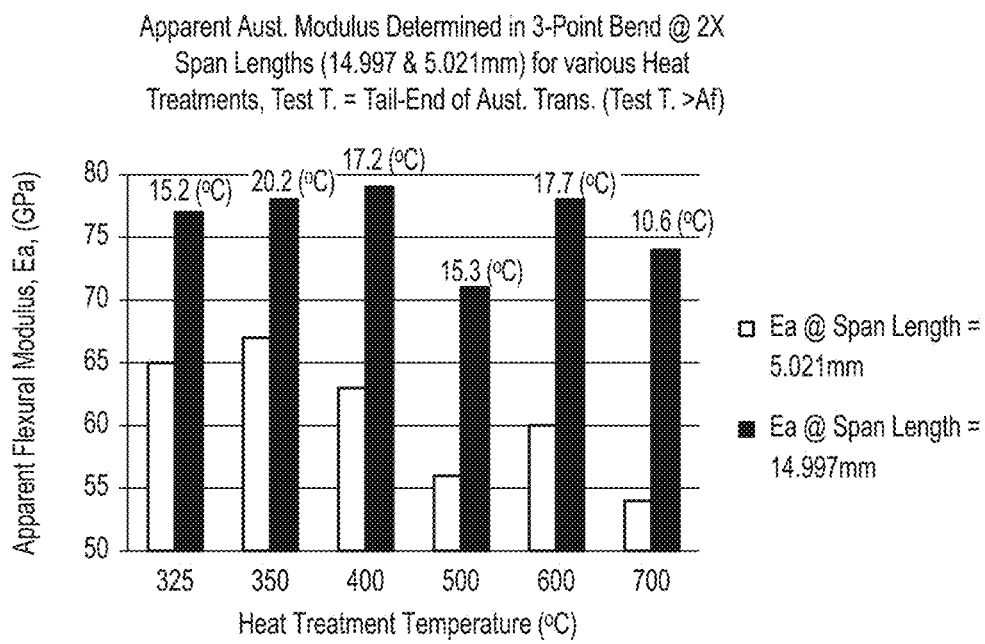
FIG. 44 is a plot of apparent flexural modulus determined in 3-point bend using quasi-static DMA for 0.764 mm Ø wire specimens possessing a variety of heat treatments (temperatures and times), specimen replicates from each population were tested over two span lengths 5 mm (red) and 15 mm (green), apparent modulus values were computed via linear elastic beam equations using force and displacement data. For each heat-treatment condition, the test temperature represents the very tail end of the austenite reverse transformation, i.e., T>Af.

FIG. 44 is a plot of apparent flexural modulus determined in 3-point bend using quasi-static DMA for 0.764 mm Ø wire specimens possessing a variety of heat treatments (temperatures and times), specimen replicates from each population were tested over two span lengths 5 mm (red) and 15 mm (green), apparent modulus values were computed via linear elastic beam equations using force and displacement data. For each heat-treatment condition, the test temperature represents the very tail end of the austenite reverse transformation, i.e., T>Af.

Figure 45:
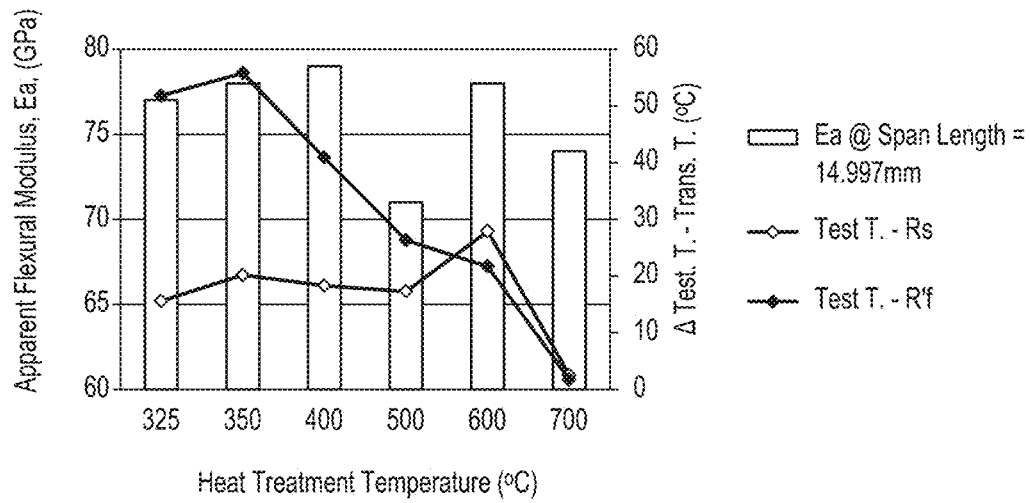
FIG. 45 is a plot of apparent flexural modulus determined in 3-point bend using quasi-static DMA for 0.764 mm Ø wire specimens possessing a variety of heat treatments (temperatures and times) and a span length of 15 mm. The test temperature represents the very tail end of the austenite reverse transformation, i.e., T>Af. The overlaid black and cyan lines indicate the proximity of the test temperature to the end of the reverse R'-phase transformation (R'f) and the start of the forward R-phase transformation (Rs).

FIG. 45 is a plot of apparent flexural modulus determined in 3-point bend using quasi-static DMA for 0.764 mm Ø wire specimens possessing a variety of heat treatments (temperatures and times) and a span length of 15 mm. The test temperature represents the very tail end of the austenite reverse transformation, i.e., T>Af. The overlaid lines indicate the proximity of the test temperature to the end of the reverse R'-phase transformation (R'f) and the start of the forward R-phase transformation (Rs).

Figure 46:
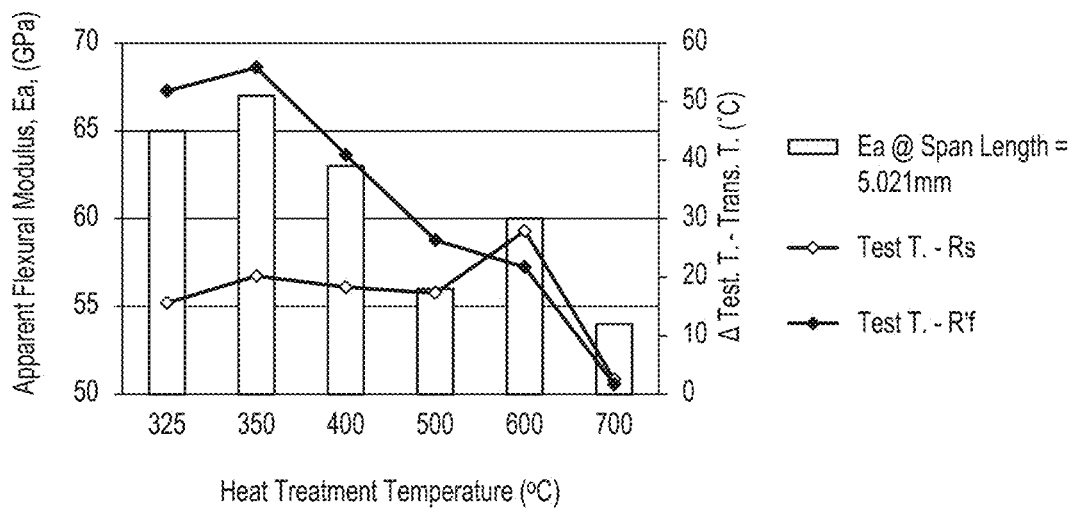
FIG. 46 is a plot of apparent flexural modulus determined in 3-point bend using quasi-static DMA for 0.764 mm Ø wire specimens possessing a variety of heat treatments (temperatures and times) and a span length of 5 mm. The test temperature represents the very tail end of the austenite reverse transformation, i.e., T>Af. The overlaid black and cyan lines indicate the proximity of the test temperature to the end of the reverse R'-phase transformation (R'f) and the start of the forward R-phase transformation (Rs).

FIG. 46 is a plot of apparent flexural modulus determined in 3-point bend using quasi-static DMA for 0.764 mm Ø wire specimens possessing a variety of heat treatments (temperatures and times) and a span length of 5 mm. The test temperature represents the very tail end of the austenite reverse transformation, i.e., T>Af. The overlaid lines indicate the proximity of the test temperature to the end of the reverse R'-phase transformation (R'f) and the start of the forward R-phase transformation (Rs).

Figure 47:
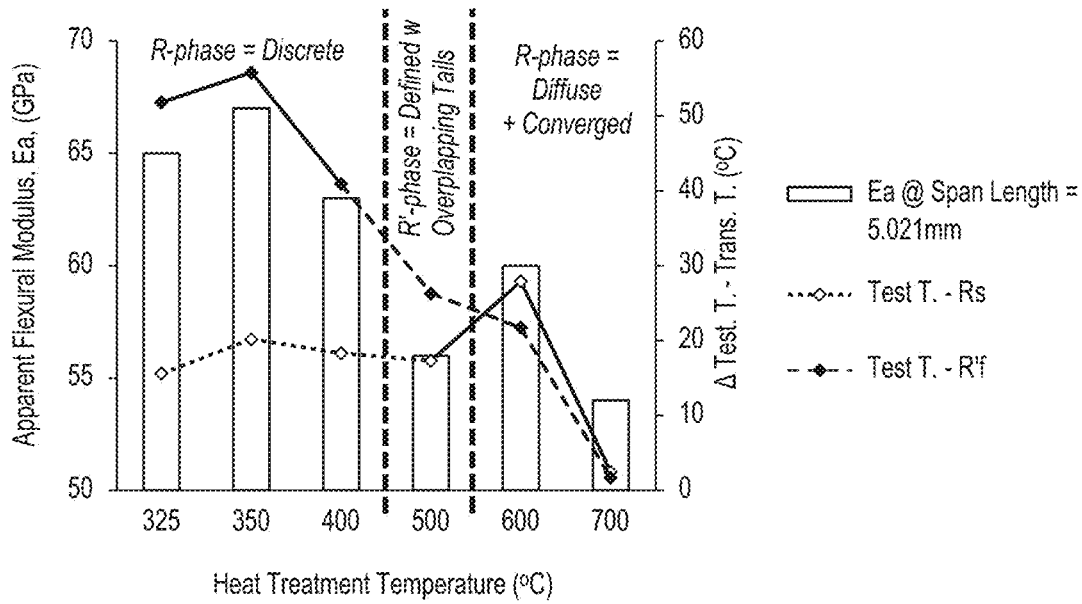
FIG. 47 is a plot of apparent flexural modulus determined in 3-point bend using quasi-static DMA for 0.764 mm Ø wire specimens possessing a variety of heat treatments (temperatures and times) and a span length of 5 mm. The test temperature represents the very tail end of the austenite reverse transformation, i.e., T>Af. The overlaid black and cyan lines indicate the proximity of the test temperature to the end of the reverse R'-phase transformation (R'f) and the start of the forward R-phase transformation (Rs).

With reference to FIG. 47, note greater correlation between apparent flexural modulus and proximity of test temperature to the reverse R'-phase finish temperature (R'f) for specimen populations where the forward R-phase occurring as a discrete exotherm. Also note greater correlation between Ea and proximity of test temperature and the forward R-phase start temperature (Rs) for forward R-phase occurring as a diffuse and converged M-phase/R-phase exotherm. The 500° C. heat treatment resulted in a well-defined R'-phase endotherm exhibiting some convergence with the austenite peak, in this particular case, proximity of test temperature to both R'-phase and R-phase appear equally well correlated.

6.4 Discussion Test Method 6

Time and resource constraints did not allow for sufficient test replicates to statistically power Study #6, 80% being a typical target [Statistical power can be thought of as the ability to determine the relationship between the variables, i.e., time and temperature of heat treatment with transformation temperatures and subsequently AFM based on sample data and have confidence that the observed correlations are the same as in the wider continuous population]. Despite lack of statistical power, consistency of trending in various data sets suggests that the results even from single replicate tests are none-the-less informative for the purpose of drawing general conclusions. It is apparent that selection of the initial test temperature at an average of 15° C. higher than Af (minimum=11° C. & maximum=20° C.) for all heat-treatment populations stifled expression of the R-phase. In a real-world context, the use temperature (37° C.) is typically 10-20° C. higher than the device Af, as such, results expressed in terms of AFM versus heat-treatment temperature are a reasonable representation of the range of behaviors one might anticipate for the various heat-treatments, regardless of whether the heat-treatments represent useful "heat-setting" schedules. All force-displacement plots were close to linear thereby suggesting all tests remained in the elastic regime, this is further supported by the maximum stress achieved in any test remaining below 190 MPa which is assumed to be well below the threshold necessary for stress inducing martensite transformation.

FIG. 44 clearly shows a significant difference in apparent flexural modulus across the range of heat treatments populations as a function of span length thereby agreeing with the results of former studies, corroborating an exaggerated shear-softening of the R-phase.

The presence of a diminutive/diffuse R-phase in the 600° C. heat-treatment population was not anticipated but readily apparent from closer scrutiny of the DSC plots. The 600° C. specimens exhibited a significant "bump" immediately preceding and partially converged with the martensite transformation, refer to FIG. 43. Presence of a very diffuse stress-induced R-phase is speculated to arise in the 700° C. populations by virtue of the very low AFM results achieved for this particular population. Results observed for the 600 and 700° C. specimen populations are counter to what was anticipated at the start of the study, since the higher temperatures typically result in absence of the R-phase in DSC data.

Figure 48:
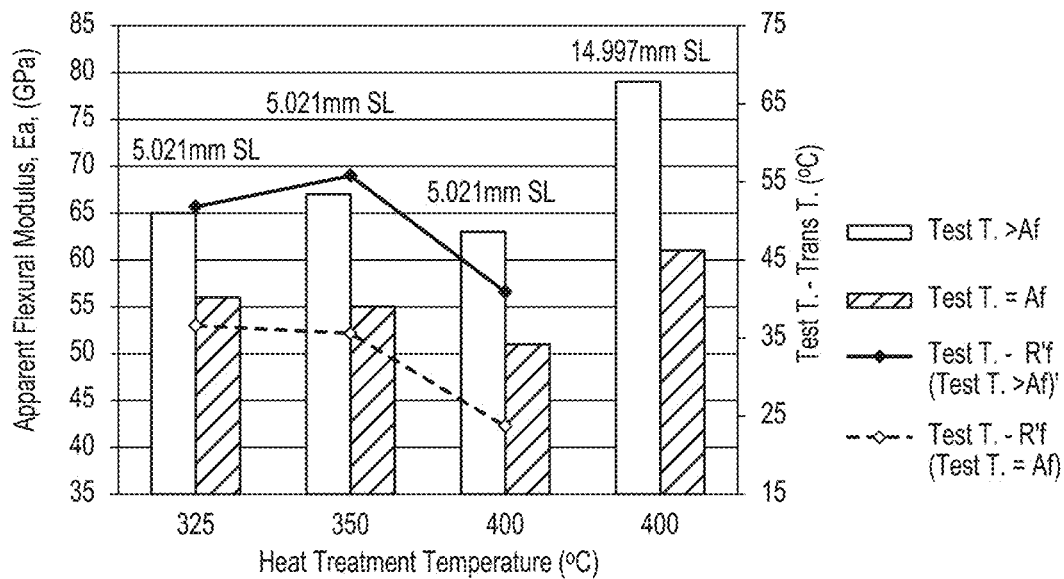
FIG. 48 is a plot of apparent flexural modulus determined in 3-point bend using quasi-static DMA for 0.764 mm Ø wire specimens possessing a variety of heat treatments (temperatures and times) and span lengths of 5 mm (red) and 15 mm (green). The test temperatures represent the very tail end of the austenite reverse transformation, i.e., T>Af (horizontal hatch), and T=Af (speckled). The overlaid solid black and dashed lines indicate the proximity of the test temperature to the end of the reverse R'-phase transformation (R'f). Note reasonable correlation between the trending in apparent flexural modulus at both test temperatures (red columns dashed & speckled columns) with proximity of test temperature relative to the reverse R'-phase transformation temperature (R'f).

FIG. 48 shows a plot of apparent flexural modulus determined in 3-point bend using quasi-static DMA for 0.764 mm Ø wire specimens possessing a variety of heat treatments (temperatures and times) and span lengths of 5 mm (red) and 15 mm (green). The test temperatures represent the very tail end of the austenite reverse transformation, i.e., T>Af (horizontal hatch), and T=Af (speckled). The overlaid solid black and dashed lines indicate the proximity of the test temperature to the end of the reverse R'-phase transformation (R'f). Note reasonable correlation between the trending in apparent flexural modulus at both test temperatures (red columns dashed & speckled columns) with proximity of test temperature relative to the reverse R'-phase transformation temperature (R'f).

Figure 49:
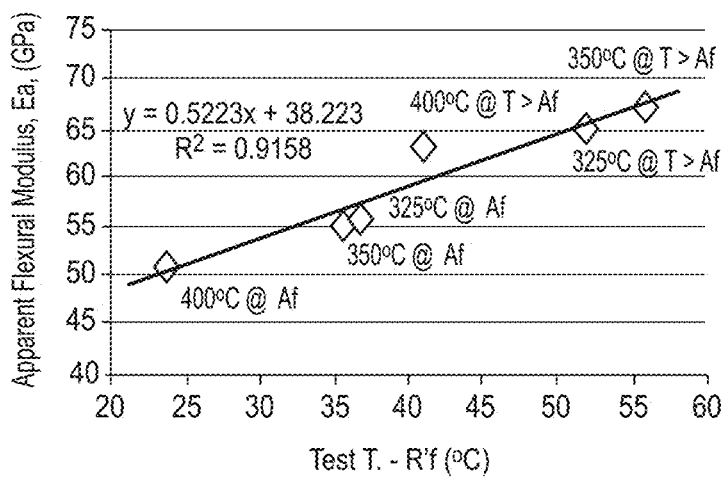
FIG. 49 is a plot of apparent flexural modulus determined in 3-point bend using quasi-static DMA for 0.764 mm Ø wire specimens possessing a variety of heat treatments (temperatures and times) and span length of 5 mm versus Test T.–R'f. The x-axis (Test T.–R'f) indicates the proximity of the test temperature to the end of the reverse R'-phase transformation (R'f). Specimens were tested at two test temperatures; (a.) the very tail end of the austenite reverse transformation, i.e., T>Af, and Test T=Af. The number of replicates for each data point is provided in Table 23.

FIG. 49 shows a plot of the apparent flexural modulus (span length=5 mm) versus Test T.-R'f, the R2 value is around 0.9 indicating a fairly good correlation between AFM (Ea) and R'f and hence an opportunity to manipulate occurrence of the R-phase to modulate modulus. It is speculated that judicious selection of heat-treatment regimens and Af tuning operations may have some potential to shift the R-phase transformations up and down in temperature and thereby maneuver the R/R'-phase closer to or further away from the use temperature (37° C.) while still allowing operation above Af. Accordingly, a more diverse impact of R-phase could be realized allowing modification of stiffness via thermomechanical processing.

Figure 50:
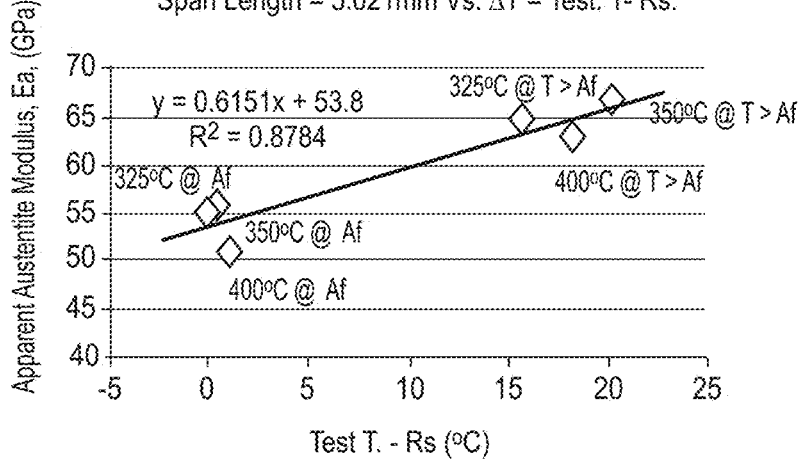
FIG. 50 is a plot of apparent flexural modulus determined in 3-point bend using quasi-static DMA for 0.764 mm Ø wire specimens possessing a variety of heat treatments (temperatures and times) and span length of 5 mm versus Test T.–Rs. The x-axis (Test T.–Rs) indicates the proximity of the test temperature to the start of the forward R-phase transformation (Rs). Specimens were tested at two test temperatures; (a.) the very tail end of the austenite reverse transformation, i.e., T>Af, and Test T=Af. The number of replicates for each data point is provided in Table 23.

FIG. 50 shows a plot of apparent flexural modulus determined in 3-point bend using quasi-static DMA for 0.764 mm Ø wire specimens possessing a variety of heat treatments (temperatures and times) and span length of 5 mm versus Test T.-Rs. The x-axis (Test T.-Rs) indicates the proximity of the test temperature to the start of the forward R-phase transformation (Rs). Specimens were tested at two test temperatures; (a.) the very tail end of the austenite reverse transformation, i.e., T>Af, and Test T=Af.

Figure 51:
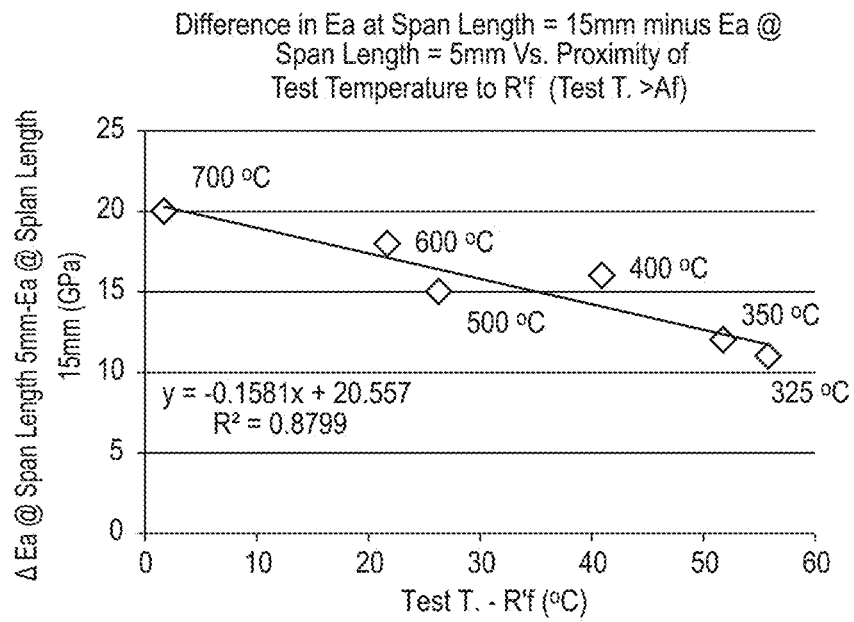
FIG. 51 is a plot of the difference in apparent flexural modulus (Δ Ea) acquired at two span lengths (5 mm and 15 mm) for a variety of heat treatments (temperatures and times) plotted versus Test T.–R'f. The x-axis (Test T.–R'f) indicates the proximity of the test temperature to the finish of the reverse R'-phase transformation (R'f). All specimens were tested at the very tail end of the austenite reverse transformation, i.e., T>$A_f$. The number of replicates for each data point is provided in Table 23. The plot shows a general trending of greater proximity of R'f to the test temperature for the higher-temperature heat-treatment which in turn correlates with a more pronounced shear-softening effect commensurate with greater difference in Ea between the two span lengths.

FIG. 51 shows the difference between the apparent flexural modulus acquired at the two test spans (5 mm and 15 mm) plotted versus Test T.-R'f representing the proximity of the test temperature to the start of the reverse R'-phase transformation. FIG. 51 clearly shows that the specimens heat-treated at 700° C. (initially assumed to be a solutionized condition with zero R-phase) shows the greatest difference in Ea as function of span length thereby suggesting (a.) the presence of R-phase; and (b.) clearly showing substantial impact of the proximity of test temperature to R'f.

7.0 Mitral TCV Inflow Stiffness Testing 7.1 Introduction

Figure 52:
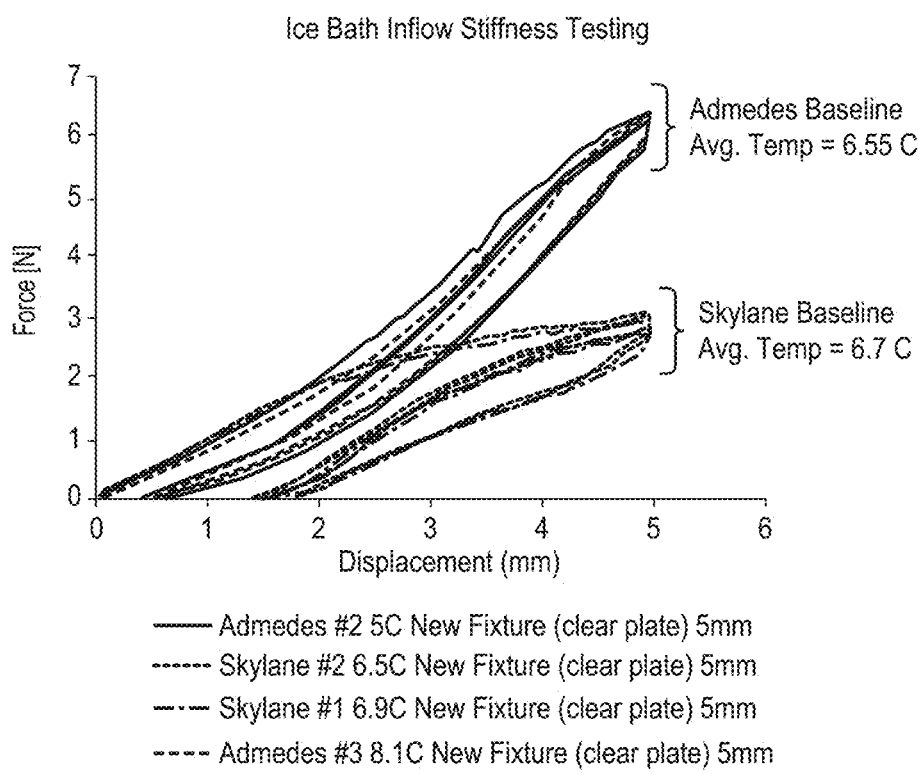
FIG. 52 is force versus displacement plots for the inflow portions of n=2 Rev. 54 Baseline Mitral TCV frames fabricated by Admedes Schuessler GmbH, and n=2 Rev. 54 Baseline Mitral TCV frames fabricated internally at the Medtronic, Inc. in Santa Rosa, Calif. (Skylane).

During implant studies of Baseline Mitral TCV it was noted that the frames "seemed really hard to deform compared to previous experience with the Skylane fabricated frames". Quantitative stiffness testing was completed using ice-bath @ T 7° C., n=2 each Admedes and Skylane were tested. The test involved feeding the outflow portion of the Mitral TCV frame through a plastic flange so that the inflow portion which 'flowers' out from the main valve housing sits on the flat flange face. Subsequently the frames were gripped at the opposite end (outflow) and the force necessary to displace the frame downwards was reported. The force therefore represents the resistance of the inflow to deformation. The results of this testing are provided in FIG. 52. The pre-implant experience was corroborated by the bench test data.

Figure 53:
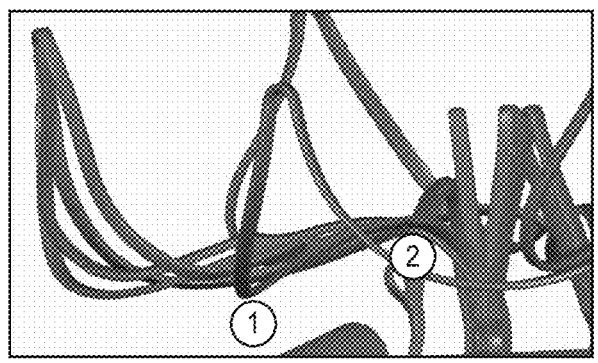
FIG. 53 is a micro-CT reconstruction viewed in Geomagic 3D software, the faint white dots above positions 1 and 2 (yellow circles) define the two points between which the measurements were made. Measurements were made from the lowest point on the underside of inflow strut (point 1) to the underside of the highest point of the arch (point 2).

Geometric differences between the Admedes and Skylane frames were assessed to gauge their impact on the observed differences in stiffness. A single Admedes and Skylane frame were scanned using micro CT and the reconstructions were interrogated using Geomagic 3D software, measurements were made of the difference in height (y plane) between the lowest point on the underside of inflow strut (point 1) to the underside of the highest point of the arch (point 2), refer to Skylane specimen #2 shown in FIG. 53. Eight (8) locations were measured on each Admedes and a Skylane Mitral frame. The results of the geometric assessment are provided in Table 26. The measured difference Skylane vs. Admedes was approximately 0.7 mm. Difference in heights (y plane) between the lowest point on the underside of inflow strut (point 1) to the underside of the highest point of the arch (point 2) was 2.707 mm (Admedes) and 2.015 mm a difference of approx. 0.7 mm.

TABLE 26

Measured dimensional differences between inflow geometries of Rev. 54 Baseline Mitral TCV fabricated by Skylane Vs. Admedes.

| Measurement | Manufacturer | |
|---|---|---|
| Replicate | Admedes | Skylane |
| 1 | 2.592 | 2.028 |
| 2 | 2.842 | 2.187 |
| 3 | 2.671 | 2.095 |
| 4 | 2.704 | 1.95 |
| 5 | 2.639 | 1.863 |
| 6 | 2.683 | 1.994 |
| 7 | 2.718 | 1.946 |
| 8 | 2.803 | 2.058 |
| Mean | 2.707 | 2.015 |
| St. Dev. | 0.082 | 0.1 |

7.2 Test Method 7.

Notwithstanding the recognized difference in geometry, a combination of DSC and DMA was used to investigate whether the observed differences in stiffness were also in some portion attributable to differences in material properties. Full and partial cycle DSC testing was completed on three (n=3) specimens each frame cut from each of the six Rev. 54 Baseline Mitral TCV frames (n=3 Admedes and n=3 Skylane). The DSC testing was completed in the same manner as discussed in Method 5 to determine start, finish and peak transformation temperature. All DMA testing was completed using a TA Instruments Q800 DMA. It is not possible to run the preferred quasi static testing in temperature scan mode therefore the following thermal schedule was employed in the default dynamic mode.

1. Equilibrate at 50° C.
2. Isothermal for 3.00 min
3. Ramp 3.00° C./min from +50° C. to −100.00° C. whilst applying a 20 μm displacement-sinusoidal load at 1 Hz.

A further limitation of the TA Q800 software renders it only capable of accepting dimension for rectangular, square, and circular cross sections. The inflow struts sections are isosceles trapezoid, all specimens were necessarily approximated to a net rectangular 2nd moment of area.

7.3 Results—Method 6.

Transformation temperatures for the n=3 Admedes and n=3 Skylane specimens are provided in Table 27. Despite the data possessing greater variability than anticipated within a discrete population of n=3 DSC replicates and across the pooled specimens from a given vendor, clear differences in trends are observed between the Admedes and Skylane frames.

TABLE 27

Transformation temperatures, start, finish, and peak, all measurements made using a TA Instruments Discovery DSC, the temperatures are derived using full and partial thermal cycles. Data provided for n = 3 inflow strut replicates cut from n = 3 Admedes-fabricated and n = 3 Skylane-fabricated Rev. 54 Baseline Mitral TCV frames.

| Specimen Replicate File | Mass | $R'_s$ | $R'_f$ | $M_s$ | $M_f$ | $A_s$ | $A_f$ | $R_s$ | $R_f$ | $A_p$ | $R_p$ | $M_p$ | $R'_p$ |
|---|---|---|---|---|---|---|---|---|---|---|---|---|---|
| Admedes 1A(2)__Plots.xlsx | 7.9 | −6.5 | 3.6 | −51.3 | −73.8 | −1.8 | 11.6 | 9.8 | −7.2 | 5.6 | 1.2 | −60.8 | −1.4 |
| Admedes 1B__Plots.xlsx | 8.3 | −6.9 | 3.7 | −50.5 | −73.1 | −3.1 | 9.3 | 8.8 | −8.5 | 4.0 | 0.1 | −60.0 | −1.7 |
| Admedes 1C__Plots.xlsx | 8.9 | −6.3 | 5.1 | −49.4 | −73.0 | −1.6 | 10.2 | 9.6 | −6.1 | 5.3 | 1.5 | −58.4 | −0.4 |
|  |  | −6.6 | 4.1 | −50.4 | −73.3 | −2.1 | 10.4 | 9.4 | −7.3 | 4.9 | 0.9 | −59.7 | −1.2 |
| Admedes 2A(1)__Plots.xlsx | 8.3 | −7.8 | 2.4 | −52.7 | −75.6 | −2.3 | 11.6 | 10.5 | −8.7 | 5.0 | 0.4 | −62.8 | −2.5 |
| Admedes 2B__Plots.xlsx | 8.4 | −8.2 | 2.8 | −52.1 | −75.1 | −2.9 | 11.5 | 10.2 | −7.9 | 4.7 | 0.1 | −62.2 | −2.7 |
| Admedes 2C(1)__Plots.xlsx | 8.7 | −8.5 | 2.4 | −52.6 | −77.4 | −3.5 | 11.5 | 10.9 | −8.8 | 4.2 | −0.3 | −62.3 | −3.1 |
|  |  | −8.2 | 2.5 | −52.4 | −76.0 | −2.9 | 11.5 | 10.5 | −8.4 | 4.6 | 0.1 | −62.4 | −2.8 |
| Admedes 3A__Plots.xlsx | 8.1 | −6.4 | 3.9 | −51.4 | −72.3 | −1.9 | 12.4 | 10.9 | −7.2 | 5.9 | 1.8 | −61.0 | −1.5 |
| Admedes 3B__Plots.xlsx | 7.6 | −7.4 | 3.2 | −51.3 | −73.2 | −2.8 | 11.8 | 10.6 | −8.4 | 4.5 | 0.1 | −60.9 | −2.1 |
| Admedes 3C__Plots.xlsx | 8.4 | −8.6 | 2.4 | −52.1 | −75.9 | −4.2 | 9.9 | 8.8 | −10.2 | 3.4 | −1.1 | −61.6 | −3.4 |
|  |  | −7.5 | 3.2 | −51.6 | −73.8 | −3.0 | 11.4 | 10.1 | −8.6 | 4.6 | .03 | −61.1 | −2.3 |
| Skylane 1A(1)__Plots.xlsx | 7 | 0.4 | 12.2 | −47.3 | −74.0 | 10.7 | 20.5 | 19.2 | 7.6 | 15.7 | 12.6 | −58.4 | 7.2 |
| Skylane 1B(1)__Plots.xlsx | 7.4 | 0.9 | 13.0 | −46.9 | −72.6 | 11.1 | 19.9 | 18.7 | 8.0 | 15.7 | 12.9 | −57.6 | 7.9 |
| Skylane 1C__Plots.xlsx | 7.3 | 1.2 | 12.7 | −46.9 | −75.0 | 10.9 | 20.9 | 19.6 | 7.8 | 15.9 | 12.9 | −57.6 | 7.8 |
|  |  | 0.8 | 12.6 | −47.0 | −73.9 | 10.9 | 20.5 | 19.2 | 7.8 | 15.8 | 12.8 | −57.9 | 7.7 |
| Skylane 2A(1)__Plots.xlsx | 6.8 | 1.6 | 12.7 | −46.4 | −75.1 | 10.9 | 20.1 | 18.7 | 8.0 | 15.8 | 13.1 | −56.9 | 8.0 |
| Skylane 2B__Plots.xlsx | 6.8 | 1.5 | 12.4 | −45.7 | −71.2 | 10.5 | 20.0 | 18.6 | 7.7 | 15.6 | 12.8 | −56.6 | 7.9 |
| Skylane 2C__Plots.xlsx | 6.2 | 2.7 | 13.3 | −46.0 | −70.7 | 10.8 | 21.1 | 19.6 | 7.7 | 16.3 | 13.3 | −55.7 | 8.5 |
|  |  | 1.9 | 12.8 | −46.0 | −72.3 | 10.7 | 20.4 | 18.9 | 7.8 | 15.9 | 13.1 | −56.4 | 8.1 |
| Skylane 3A__Plots.xlsx | 7.3 | 2.1 | 13.0 | −45.8 | −70.7 | 11.1 | 20.1 | 19.1 | 7.9 | 16.0 | 13.1 | −56.2 | 8.1 |
| Skylane 3B__Plots.xlsx | 7.5 | 6.5 | 20.1 | −37.3 | −59.8 | 12.8 | 21.9 | 20.1 | 10.3 | 17.6 | 15.1 | −47.0 | 12.8 |
| Skylane 3C(1)__Plots.xlsx | 6.4 | 6.6 | 18.6 | −38.0 | −62.8 | 13.2 | 22.2 | 20.6 | 10.7 | 18.0 | 15.3 | −47.6 | 12.8 |
|  |  | 5.1 | 17.2 | −40.4 | −64.4 | 12.4 | 21.4 | 20.0 | 9.6 | 17.2 | 14.5 | −50.3 | 11.2 |

Skylane inflow struts exhibit an M→R→A reverse transformation sequence (heating) whereas Admedes inflow struts exhibit M→A, a summary is provided in Table 28.

TABLE 28

Transformation sequences observed for n = 3 inflow cut from the Rev. 54 Baseline Mitral TCV fabricated by Skylane Vs. Admedes.

| Manufacturer | Replicate | Transformation Sequences | |
|---|---|---|---|
|  |  | Forward | Reverse |
| Admedes | 1 | A→R→M | M→A |
| Admedes | 2 | A→R→M | M→A |
| Admedes | 3 | A→R→M | M→A |
| Skylane | 1 | A→R→M | M→R→A |
| Skylane | 2 | A→R→M | M→R→A |
| Skylane | 3 | A→R→M | M→R→A |

Figure 54:
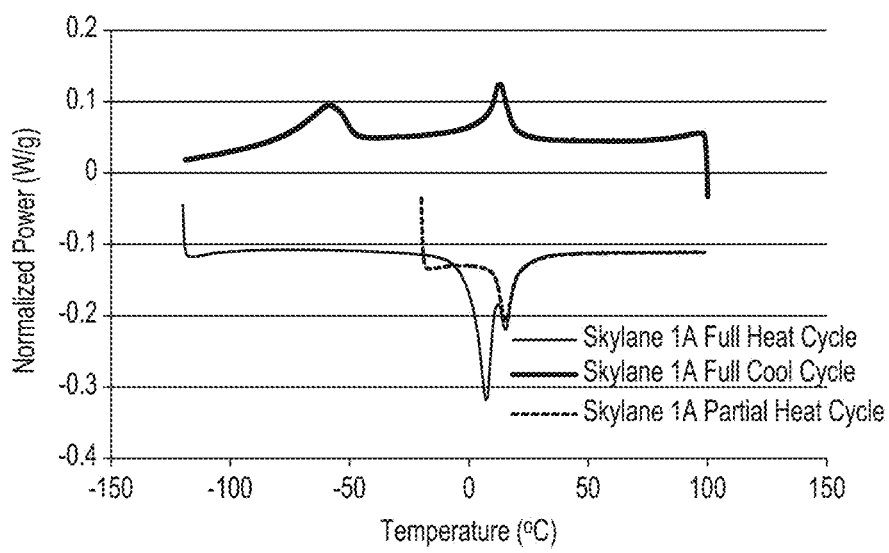
FIG. 54 is a DSC thermogram for a representative Skylane-fabricated Rev. 54 Baseline Mitral TCV inflow strut specimen (1A), the partial cooling cycle is omitted. The R'-phase and austenite endotherms are partially overlapped as evidenced by small bifurcation.

FIG. 54 shows a DSC thermogram for a representative Skylane-fabricated Rev. 54 Baseline Mitral TCV inflow strut specimen (1A), the partial cooling cycle is omitted. The R'-phase and austenite endotherms are partially overlapped as evidenced by small bifurcation.

Figure 55:
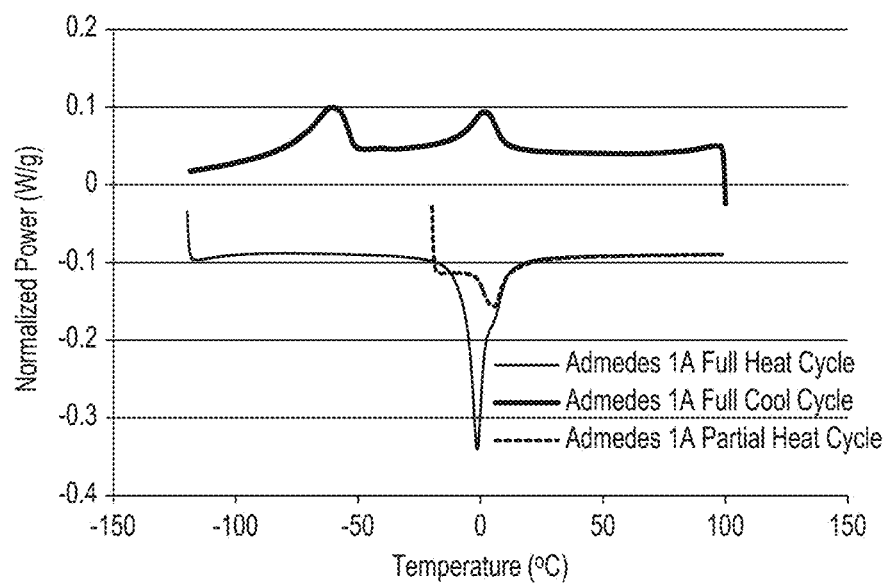
FIG. 55 is a DSC thermogram for a representative Admedes-fabricated Rev. 54 Baseline Mitral TCV inflow strut specimen (1A), the partial cooling cycle is omitted. The R'-phase and austenite endotherms converge into a single endotherm, while there is a bulge at the side of the peak associated with the R'→A endotherm, there is no evidence of bifurcation.

FIG. 55 shows a DSC thermogram for a representative Admedes-fabricated Rev. 54 Baseline Mitral TCV inflow strut specimen (1A), the partial cooling cycle is omitted. The R'-phase and austenite endotherms converge into a single endotherm, while there is a bulge at the side of the peak associated with the R'→A endotherm, there is no evidence of bifurcation.

Figure 56:
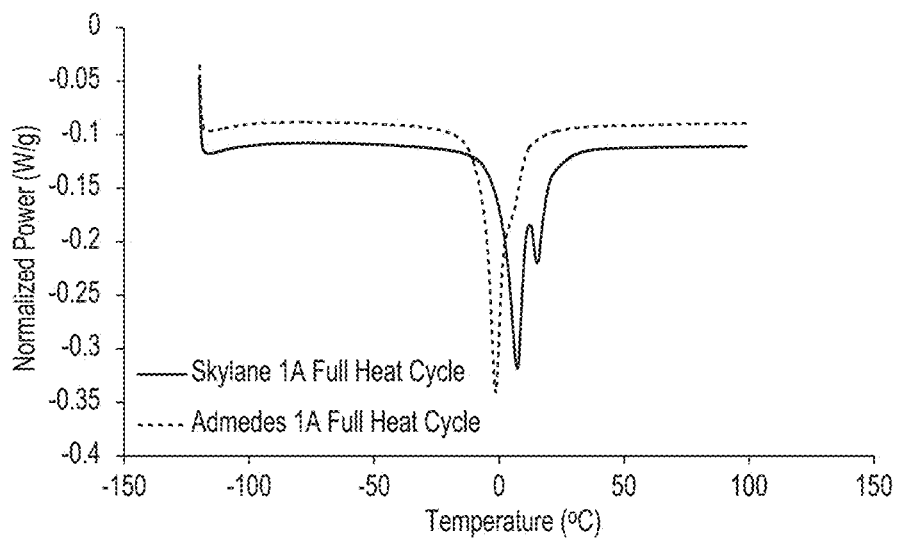
FIG. 56 is a plot of full heat cycle DSC endotherm peaks for representative Admedes-fabricated and Skylane-fabricated Baseline Mitral TCV inflow strut specimens (both specimens=#1A). Convergence (Admedes) and lack of convergence (Skylane) of the R'-phase and austenite endotherms are clearly shown.

FIG. 56 shows a plot of full heat cycle DSC endotherm peaks for representative Admedes-fabricated and Skylane-fabricated Baseline Mitral TCV inflow strut specimens (both specimens=#1A). Convergence (Admedes) and lack of convergence (Skylane) of the R'-phase and austenite endotherms are clearly shown.

Figure 58:
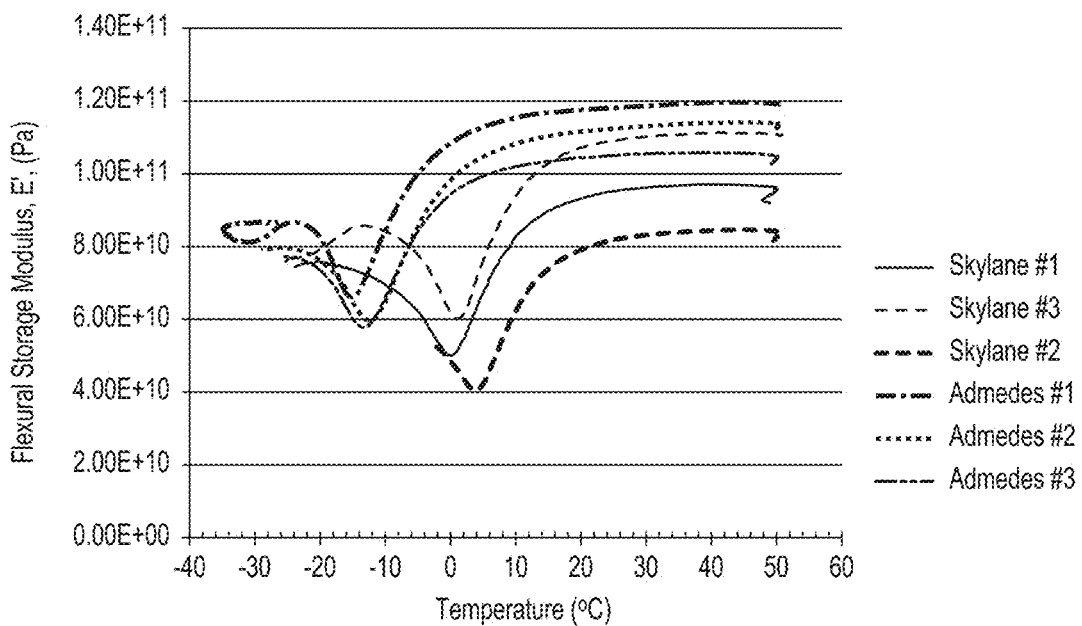
FIG. 58 is a plot of flexural storage modulus vs. temperature in 3-point bending mode for inflow struts cut from n=3 Admedes and n=3 Skylane manufactured Rev. 54 Baseline Mitral TCV frames.

FIG. 58 provides flexural storage modulus vs. temperature plots for n=3 Admedes and n=3 Skylane specimens.

Figure 57:
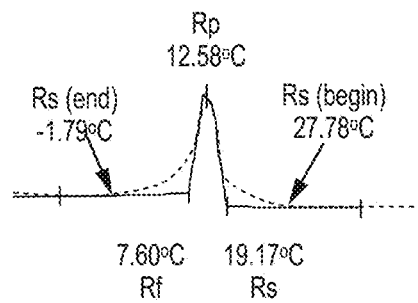
FIG. 57 is a schematic plot differentiating between 'standard' transformation start and finish temperatures and those temperatures representing the very beginning and end of the transformation, i.e., the tails.
Figure 59A:
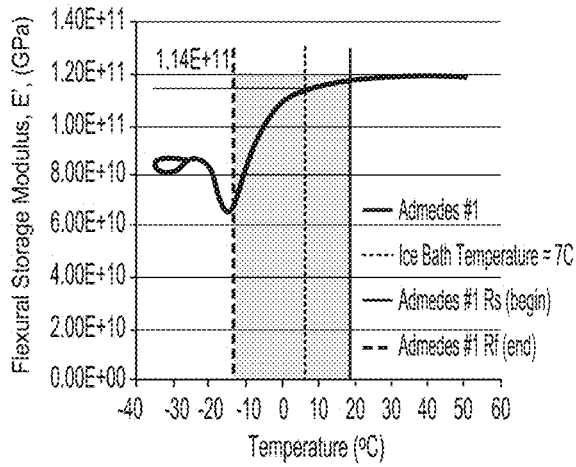
FIG. 59A is a flexural storage modulus vs. temperature plot Admedes #1.
Figure 59B:
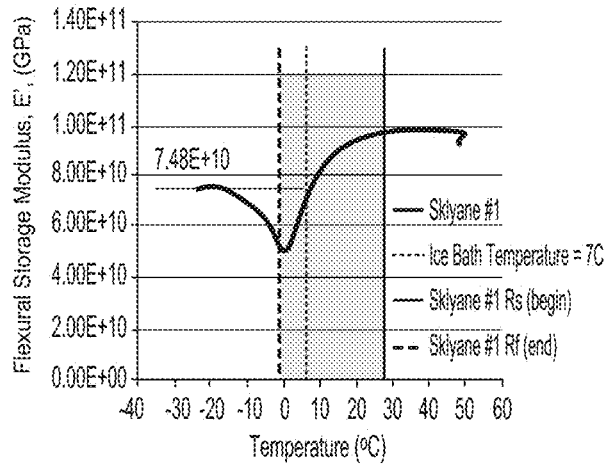
FIG. 59B is a flexural storage modulus vs. temperature plot Admedes #2.
Figure 59C:
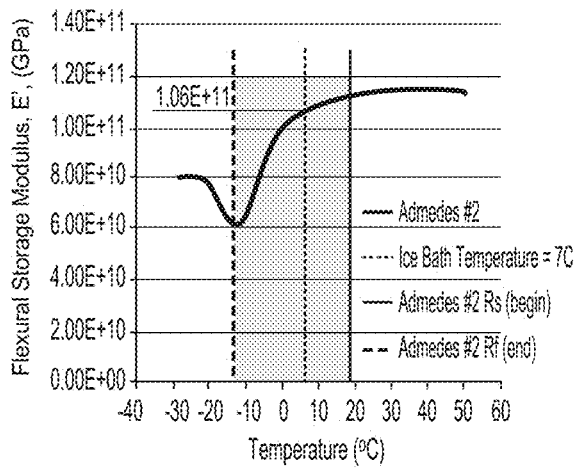
FIG. 59C is a flexural storage modulus vs. temperature plot Admedes #3.
Figure 59D:
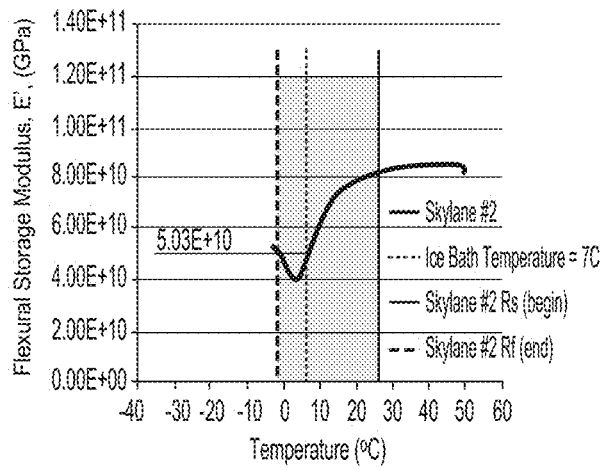
FIG. 59D is a flexural storage modulus vs. temperature plot Skylane #1.
Figure 59E:
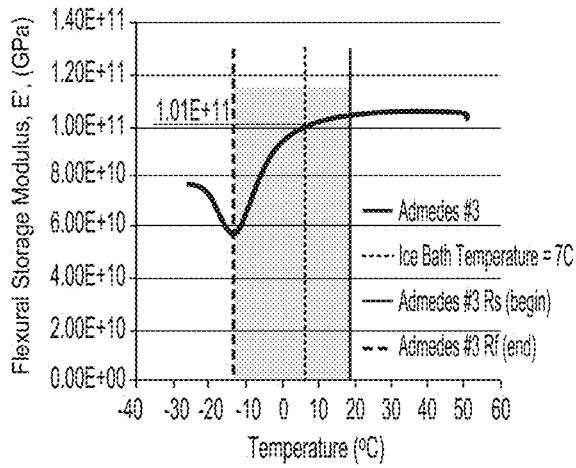
FIG. 59E is a flexural storage modulus vs. temperature plot Skylane #2.
Figure 59F:
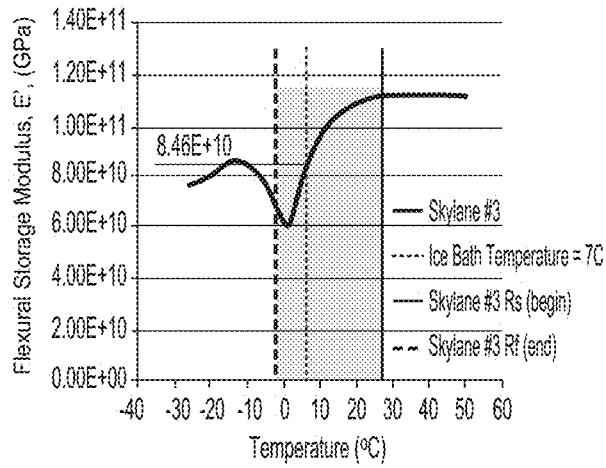
FIG. 59F is a flexural storage modulus vs. temperature plot Skylane #3.

Individual flexural storage modulus vs. temperature plots are provided for inflow struts cut from n=3 Admedes and n=3 Skylane manufactured Rev. 54 Baseline Mitral TCV frames FIG. 59A-F, in each case the modulus at 7° C. representing the ice-water bath temperature are indicated on each plot. The individual results are summarized in Table 29. In FIG. 59A-C, the pink overlay rectangle delineates the entire temperature range for the R-phase exotherm starting at the very onset on the transformation and diminishing at the very end tail of the exotherm as shown schematically in FIG. 57. Likewise, the green overlay rectangles in FIG. 59D-F delineate the entire temperature range for the R-phase transformation.

TABLE 29

Summary of flexural storage modulus results at 7° C. for n = 3 inflow cut from the Rev. 54 Baseline Mitral TCV fabricated by Skylane vs. Admedes.

| Specimen Replicate | E' Storage @ 7° C. (GPa) | |
|---|---|---|
|  | Skylane | Admedes |
| 1 | 85 | 114 |
| 2 | 75 | 101 |
| 3 | 50 | 106 |
| Mean | 70 | 107 |

7.4 Discussion Test Method 6.

The R-phase transformation exhibited by Admedes inflow struts occurs at a lower temperature than Skylane struts, approx. 10° C. lower. The R-phase possesses a lower elastic modulus than the austenitic phase. At a temperature of 7° C. in the ice water bath, the Skylane inflow strut material is approximately 25-35% less stiff than the Admedes inflow strut material. The lower temperature of the R-phase transformation observed in the Admedes specimens is implicated in their greater stiffness as observed during chilled-loading in pre-clinical use and as corroborated via bench testing at 7° C. using iced water. Assuming that the raw tabes from which the Skylane and Admedes Mitral TCV were fabricated are similar e.g. Ni-content, the reported differences in loading forces between Skylane and Admedes inflow observed during pre-clinical use are attributable to either differences in thermomechanical processing or slight differences in chemical composition. The impact of the dimensional also needs to be taken into consideration although their impact appears secondary to the observed shift in material properties at the depressed temperature.

The flexural storage modulus computed using dynamic DMA testing concurrent with temperature cycling routinely report excessively high dynamic moduli for the NiTi specimens. The root cause of this phenomenon has not been established. A number of factors that may contribute to the observed discrepancy, these are briefly discussed below:

1. Force Track compensation function of the DMA software results in significant displacement modulation concurrent with abrupt stiffness changes coincident with the transformations. For the cpTa, no phase transformation is observed, during tests on non-hystoelastic materials, the DMA software has no need to compensate for any significant real-time material-driven "softening" of the specimen, i.e., phase transformation, accordingly the modulus values reported for cpTa as determined in dynamic mode are in alignment with those reported in the literature.

Figure 60:
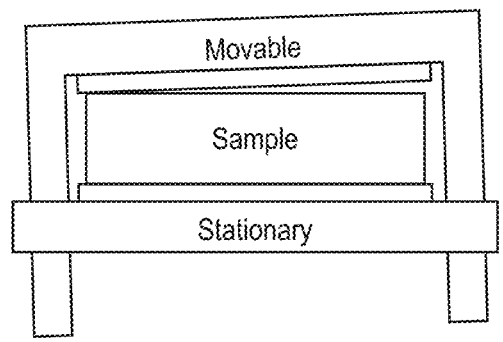
FIG. 60 is a schematic drawing of poor sample clamping during a DMA flexural test associated with specimen twist.

2. When the DMA is used in continuous mechanical oscillation mode at constant frequency and amplitude using the 3-point bending fixtures, it is assumed that the sample has good contact with the clamps. However, if there is a twist in the sample, no matter how subtle, the contact is less than adequate. For relatively rigid/high modulus materials, such as NiTi, the inadequate contact leads to erroneous evaluations of modulus, FIG. 60 illustrates this effect in an exaggerated form. Even very small twists in the specimen are capable of causing the effects shown in FIG. 60, such that the storage modulus seems to increase. This occurs as the beam starts to conform to the clamp geometry. The clamp then experiences the full width of the specimen responding to the oscillations.

7.5 Conclusion Test Method 6.

The lower temperature of the R-phase transformation observed in the Admedes specimens is implicated in their greater stiffness as observed during chilled-loading in pre-clinical use and as corroborated via bench testing at 7° C. using iced water.

D. Threshold Aspect Ratios (L/d) for Optimal Force-Controlled and Displacement-Controlled Durability in Nitinol Devices Scaffolds and supports fabricated from shape-memory and superelastic alloys used in vascular applications, e.g., stents, frames, and endografts are subjected to a combination of displacement- and force-controlled loading. However, it is evident that one mode often predominates throughout the device or in a portion or zone of the device. For applications such as orthopedic/spinal implants the systems are ostensibly force-controlled but typically displacement-limited. Either displacement-controlled or force-controlled fatigue loading conditions arise as a function of the system as a result of both the extrinsic loading plus design & material interactions. There are essentially two fundamental methods to improve fatigue durability depending on the predominant fatigue mode: (a.) force-controlled—make the structure stiffer to resist the imposed loads; or (b.) displacement-controlled—make the structure more compliant to better accommodate or distribute the imposed deformations. Many different structural beam geometries exist in current Nitinol implants. However, to our knowledge, none of these structural beam members have been specifically engineered to inhibit the R-phase transformation in vivo, thereby promoting the desired stiffness through a combination of microstructural refinement and geometric design of the structural beam elements.

It has been discovered that a unique combination of the geometry and metallurgy of nitinol can promote a desirable stiffening of an entire implant, or sub-components within that implant. When nitinol structural beams are loaded in bending, the minor shear component acts to stress-induce the austenite to R-phase transformation and ensuing reorientation of the R-phase variants, these events 'soften' the structural beams. For a nominally fixed length (L) of structural beam loaded in bending the apparent flexural modulus (AFM) of nitinol softens such that slimmer structural beams exhibit larger moduli than thicker structural beams of the same length, which is in contrast to conventional metal structural beams for which the AFM is independent of the cross-sectional area. In an analogous manner, for fixed depth of structural beam (d), AFM scales proportionally with length, i.e., AFM α L/d for nitinol that transitions to R-phase.

R-phase can be promoted or inhibited by, for example, the choice of shape-setting temperature and time. Generally, higher temperatures inhibit and lower temperatures promote the R-phase.

1. Geometric Manipulation for Stiffening (favoring Force-Controlled Fatigue Conditions)

Figure 61:
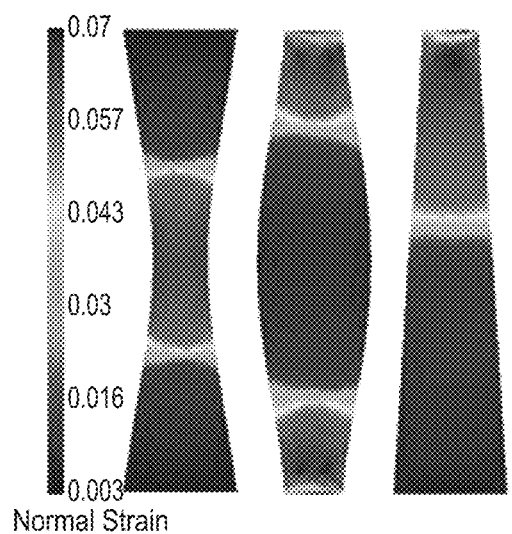
FIG. 61 is an image showing strain localization stress.

If the thermo-mechanical processing is fixed, then to achieve the greatest possible stiffness, regional slimming of individual elements (e.g. struts) can be achieved by modifying the cross-section across the element—symmetrical and non-symmetrical tapered, hour-glassed, and barreled structural beams. Those elements with serpentine profiles and/or a non-uniform 2nd moment of area tend to focus strain energy and cause strain localization. This strain localization stress induces transformation at the smallest cross-sections opposing the imposed loads and thereby promotes a focal R-phase softening, refer to FIG. 61 where red contours equate with strain localizations.

In cases were R-phase softening is undesirable, uniform prismatic structural beam elements (rather than tapered) may be employed. When prismatic beams are used, strain localization and concomitant shear-softening events are avoided in devices where greater stiffness and superior load-controlled fatigue performance are sought. While symmetrical/uniform structural beams are preferred for load-controlled fatigue durability, non-symmetrical/non-uniform structural beams may be employed. Regardless of structural beam configuration, the dimensions of the structural beam may be readily manipulated to achieve the desired stiffness.

Figure 62:
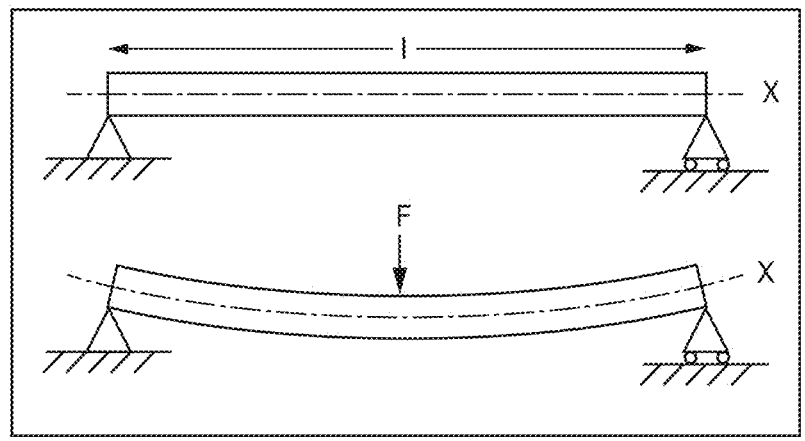
FIGS. 62-63 are schematic drawings illustrating bending and shear stresses during bending of a structural beam element.
Figure 63:
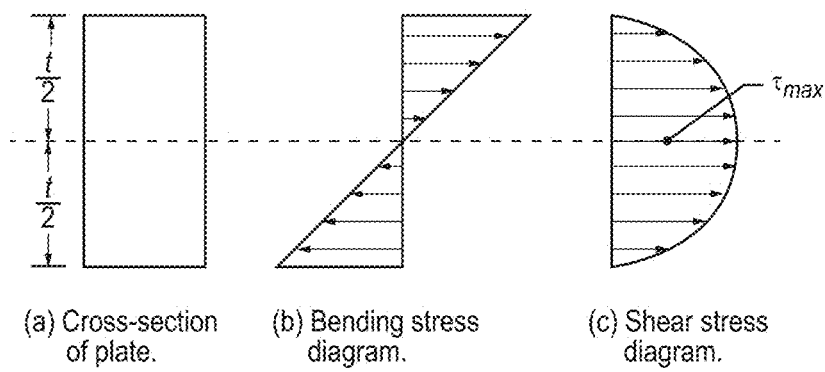

With reference to FIGS. 62-63, during bending of structural beam elements the top fibers will be in compression and the bottom fibers will be in tension, but the shear stress is zero at the extreme fibers and maximum at the center.

The ratio of the shear contribution to the bending contribution is given by Equation 1B.

$$\frac{PLh^2/40GI}{PL^3/24EI} = \frac{3h^2E}{5L^2G} \quad \text{Equation 1B}$$

By inspection of Equation 1B, the importance of the shear term scales as $(h/L)^2$, where 'h' is interchangeable with 'd', i.e., quadratically with the span length-to-height ratio.

Preferably the breadth (a.k.a width) of the beam element is greater than depth (a.k.a height) such that the imposed loading occurs over the flatwise orientation as opposed to the edgewise orientation. Beam geometry with a length-to-depth ratio typically greater than 8:1 is used to minimize the shear forces in the beam, thereby inhibiting the R-phase transformation which is a shear-dominated phase transformation. Depth refers to that dimension of the device resisting a majority of the imposed barb loading forces. The most desirable or optimum threshold ratio may be determined experimentally or deduced from a suitable mathematical model, e.g., finite element analysis (FEA).

If the beam is too short relative to its depth shear softening will detract from the overall stiffness whereas if the beam is too long relative to its depth the section modulus will detrimentally impact the stiffness. While designing the beam geometry, the breadth (or width) dimension is also controlled to maintain the polar moment of area and thereby avoid excessive twisting which might otherwise promote concomitant non-desirable off-axis/out-of-plane shear-softening. Preferably the breadth (a.k.a width) of the appendage feature is greater than depth (a.k.a height) such that the imposed loading occurs over the flatwise orientation as opposed to the edgewise orientation.

For a fixed microstructure, the preferred depth-to-length ratio may be derived in manifold ways. It may be readily determined using flexural testing over multiple span ratios in a desired loading mode e.g. cantilever structural beam testing such that a maximum achievable apparent flexural modulus is determined at the desired use temperature by means of a simple 'least squares' fitting of such data. Subsequently a target percentage of the maximum achievable apparent flexural modulus (AFM) is settled on. Taking the equation describing the relationship between AFM and L/d or $(d/L)^2$, a suitable aspect ratio can be determined which is then used as a direct design input to define the dimensions of the structural beam element, thereby affording the preferred stiffness, where stiffness will be a compound function of both AFM and moment of area.

In summary, regardless of how the R-phase manifests and at what temperature it occurs, geometric design is used to confer optimal stiffness.

2. Geometric Manipulation for Greater Compliance (favoring Displacement-Controlled Fatigue Conditions)

In an analogous but opposite manner to that described above, if the thermo-mechanical processing is notionally fixed, then regional slimming of individual elements (e.g. struts) can be employed to better distribute/accommodate strains. This can be achieved by deliberately modifying the cross-section across the element with tapered elements, e.g., hour-glassed, and serpentine beams. Those elements with regionally slimmed profiles and/or a non-uniform 2nd moment of area tend to better distribute imposed mechanical loads. As described above in "Geometric Manipulation for Stiffening", tapered, hour-glassed, and barreled structural beams tend to focus strain energy and promote strain localization. Beam geometry with a length-to-depth ratio typically less than 8:1 may be used to enhance the shear forces in the beam, thereby promoting the R-phase transformation which is a shear-dominated phase transformation. If the beam is too short relative to its depth section modulus effects will detract from the overall achievable compliance. While designing the beam geometry, the breadth (or width) dimension may also be controlled to maintain a desired polar moment of area and thereby control the propensity for twisting which might otherwise promote concomitant off-axis shear-softening.

3. Metallurgical Manipulation for Stiffness Control

If a structural beam geometry is fixed, the metallurgy may be manipulated to either inhibit (or reduce) the occurrence of the R-phase to stiffen the beam, or to promote (or increase) the occurrence of the R-phase to soften the beam. This may be achieved by controlling the time, temperature, stresses and strains during the shape setting process. For a fixed thermo-mechanical process, the geometry is designed in such a way to reduce the shear forces, thereby minimizing the influence of any R-phase that may persist in the nitinol component. Specifically, thermal treatments in the range of 300-525° C. for 15-600 seconds promotes a separation of the R-phase from the Austenite-phase as characterized by the heating cycle in DSC. This separation inhibits R-phase transformation in vivo.

In summary, for a fixed geometry of structural beam element with fixed moments of area, thermal processing may be preferentially manipulated to confer desired stiffness.

4. Combined Geometric and Metallurgical Manipulation for Stiffness Control

Realistically, designers will be limited in their choice of geometric beam profiles and/or thermo-mechanical treatments. Therefore, a compromise of pairing the geometry with thermo-mechanical heat treatment may be employed to achieve the desired stiffness. In other words, the thermo-mechanical processing of an implant device may be preferentially driven to satisfy other performance aspects and not necessarily to satisfy a desired material condition to optimize the structural beam elements for maximum stiffness.

E. Nitinol Geometry for Enhances Stiffness and Durability

Implantable Nitinol medical devices often rely on fixation barbs to secure the implant in its desired anatomical position. Other devices may include appendage structures that project from the main superstructure, e.g., synch eyelets. Unlike the superstructure of the implant which may require some amount of compliance for optimized performance, appendages such as fixation barbs exhibit maximum anchoring ability for fixation and long-term fatigue durability by virtue of their rigidity, i.e., their non-deformable and stiff properties. In an analogous manner, synch eyelets benefit from greater rigidity. Many different fixation barb and appendage geometries exist in current Nitinol implants. However, such barbs have not been specifically engineered to inhibit the R-phase transformation in vivo, thereby promoting the desired stiffness through a combination of microstructural refinement and geometric design of the barb.

It has been discovered that a unique combination of the metallurgy and geometry of Nitinol can promote a desirable stiffening of an entire implant, or sub-components within that implant. For example, R-phase can be promoted or inhibited by the choice of shape-setting temperature and time. Generally, higher temperatures inhibit and lower temperatures promote the R-phase.

When nitinol beams are loaded in bending, the minor shear component acts to stress-induce the austenite to R-phase transformation and ensuing reorientation of the R-phase variants, these events 'soften' the beams and do so in a counterintuitive manner. For a nominally fixed length (L) of beam loaded in bending, whereas for conventional metal beams the apparent flexural modulus (AFM) is independent of the cross-sectional area, the AFM of nitinol softens such that slimmer beams exhibit larger moduli than thicker beams of the same length. In an analogous manner, for fixed depth of beam (d), AFM scales proportionally with length, i.e., AFM α L/d.

On the basis of these findings, to produce rigid, non-deformable, and 'stiff' fixation barbs or other projecting appendage feature, the metallurgy may be manipulated by the appropriate selection of thermal aging time, temperature, and deformation to inhibit (or minimize) the occurrence of the R-phase in vivo. The thermo-mechanical processing of an implant device may be preferentially driven to satisfy other performance aspects and not necessarily to satisfy a desired material condition to optimize/maximize the fixation barb stiffness. Regardless of how the R-phase manifests and at what temperature it occurs, geometric design is used to confer optimal stiffness. Notwithstanding, for a fixed geometry of fixation barb or other projecting appendage feature with fixed moments of area, thermal processing may be preferentially manipulated to confer enhanced stiffness.

To achieve the enhanced stiffness, regional slimming in the form of symmetrical and non-symmetrical tapered, hour-glassed, and barreled structural beams, e.g., those with serpentine profiles and non-uniform 2nd moment of area focus strain energy and cause strain localization which acts to stress-induce transformation at the smallest cross-sections opposing the imposed loads and thereby promote a focal R-phase softening. Instead uniform prismatic structural beam elements are preferentially employed. In any case, strain localization and concomitant shear-softening events are avoided or reduced in devices where greater stiffness and superior stress-controlled fatigue performance are sought. While symmetrical/uniform structural beams are preferred, non-symmetrical/non-uniform structural beams may be employed. Regardless of structural beam configuration, the dimensions of the structural beam may be readily manipulated to achieve the desired stiffness.

For a fixed thermo-mechanical process, the geometry is designed in such a way to reduce the shear forces, thereby reducing the influence of any R-phase that may persist in the nitinol component. Specifically, thermal treatments in the range of 300-525° C. for 15-600 seconds promotes a separation of the R-phase from the Austenite-phase as characterized by the heating cycle in DSC. This separation inhibits R-phase transformation in vivo. Furthermore, a barb geometry with a length-to-depth ratio typically greater than 8:1 is used to reduce the shear forces in the barb, thereby inhibiting the R-phase transformation which is a shear-dominated phase transformation. Depth refers to that dimension of the device resisting a majority of the imposed barb loading forces. The most desirable or optimum threshold ratio may be determined experimentally or deduced from a suitable mathematical model, e.g., finite element analysis (FEA).

If the barb is too short relative to its depth shear softening may detract from the overall stiffness whereas if the barb is too long relative to its depth the section modulus may detrimentally impact the stiffness. While designing the fixation barb or other projecting appendage feature, the breadth (or width) dimension may also be controlled to maintain the polar moment of area and thereby avoid excessive twisting which might otherwise promote concomitant non-desirable off-axis/out-of-plane shear-softening.

Preferably the breadth (a.k.a width) of the appendage feature is greater than depth (a.k.a height) such that the imposed loading occurs over the flatwise orientation as opposed to the edgewise orientation.

For a fixed microstructure, the preferred depth-to-length ratio may be derived in a number of ways. It may be readily determined using flexural testing over multiple span ratios in a desired loading mode e.g. cantilever beam testing such that a maximum achievable apparent flexural modulus is determined at the desired use temperature by means of a simple 'least squares' fitting of such data. Subsequently a target percentage of the maximum achievable apparent flexural modulus (AFM) may be settled on. Taking the equation describing the relationship between AFM and L/d or $(d/L)^2$, a suitable aspect ratio may be determined which may then be used as a direct design input to define the dimensions of the fixation barbs or projecting appendage feature, e.g., cinch eyelet, thereby affording a preferred stiffness, where stiffness will be a compound function of both AFM and moment of area.

Figure 64:
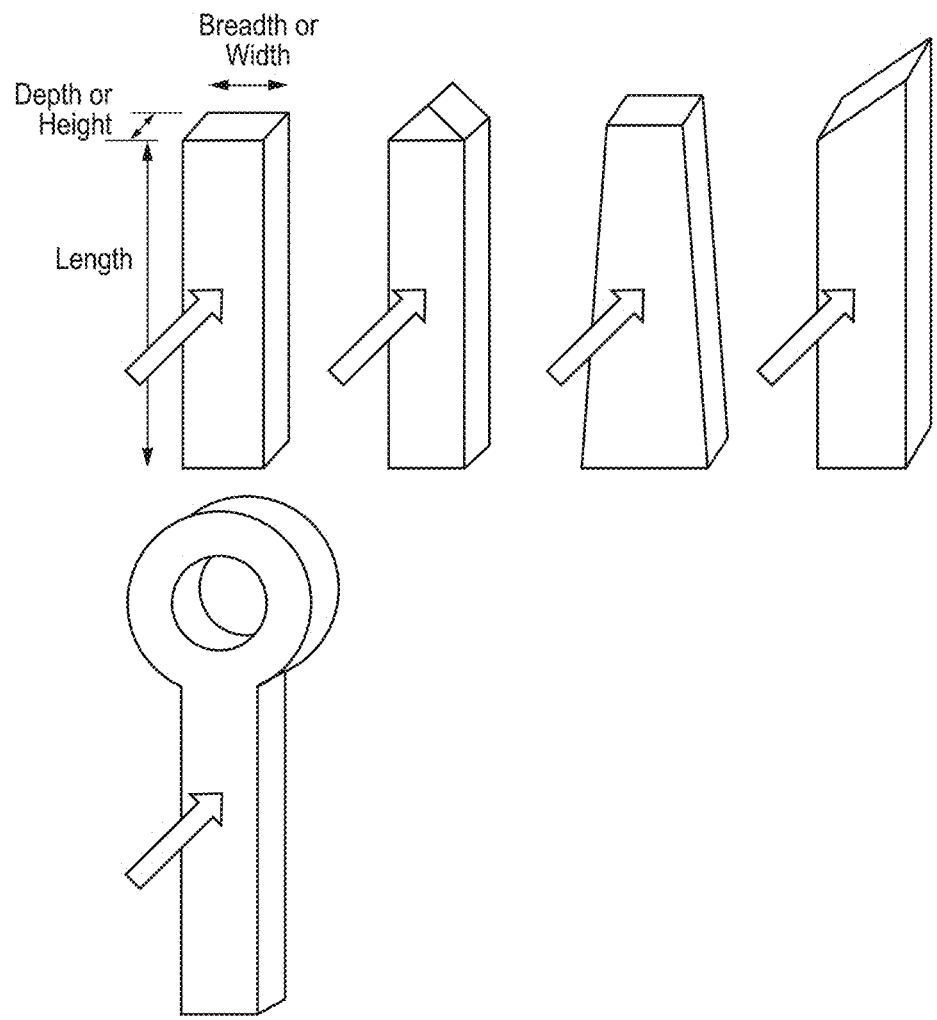
FIG. 64 is schematic drawings of four basic fixation barb shapes and an eyelet appendage.

FIG. 64 shows four basic fixation barb shapes and an eyelet appendage. Using the fixation barbs for examples, in all four cases it is assumed that the imposed force/displacement acts across the depth or height dimension (yellow arrow). The Breadth or Width dimension is nominated as that dimension normal to the imposed load. In the schematic per the preferred configuration breadth or width is greater than depth or height (d>b) such that the fixation barbs are loaded in a so-called flatwise orientation. Designing the fixation barb or projecting appendage such that loading occurs in the flatwise orientation is preferred but not necessary.

F. Predict Relative Fatigue Performance of SMA Articles

The present disclosure describes, among other things, experiments that have determined that ductility and toughness are more important than strength in determining fatigue resistance of SMAs, particularly those that are compressed or loaded prior to or during use or during recaptured post-deployment. Such compression or loading may act to promote an inhomogeneous distribution of plastic strain which may lead to undesirable local stress concentrations and large slip offsets at surfaces or interfaces depending on the properties inferred by the prevailing microstructure. For example, compression or loading may introduce micro-cracks regardless of material strength. As described herein, the ability to resist propagation of initial cracks and the ability to resist inhomogeneous distribution of plastic strains may be more relevant to fatigue performance than the ability of a stronger material to resist initiation of such inhomogeneities or micro-cracks, particularly when the SMA is pre-loaded prior to use, or is subjected to post-deployment recapture, or the like.

The SMAs may be processed or worked to provide the material with properties that provide superior fatigue resistance. However, as described herein, material that has already been processed or worked may be selected by obtaining relatively straight forward stress-strain data for the material, such as uniaxial stress-strain data. The stress analyses presented herein focus on the plastic portion of the engineering stress-strain curve with the exception of the martensite modulus which is used to establish the yield stress via a percentage offset construction. Those materials that exhibit properties that confer increased ductility or toughness may be selected as materials that are likely to exhibit superior fatigue resistance.

As described herein, a number of factors have been identified as contributing to superior fatigue-resistance. These factors include a critical stress for cross slip, yield strength, toughness, strain at ultimate tensile strength, UTS to yield stress ratio and the Voce saturation stress. More particularly, it has been found that SMA materials having lower critical stress for cross slip may result in superior fatigue performance. SMA materials processed such that they exhibit lower yield strength or stress may result in superior fatigue resistance. SMA materials processed such that they exhibit increased toughness may result in superior fatigue performance. SMA materials processed to possess increased strain at ultimate tensile strength may result in superior fatigue performance. SMA materials possessing an increased ultimate tensile strength to yield strength ratio may result in superior fatigue performance. Any one or more of these factors may be evaluated for determining or predicting whether the SMA material or article formed therefrom may exhibit superior fatigue resistance. These factors may be of increased importance in cases in which the SMA article is preloaded prior to chronic use or fatigue testing.

In embodiments, a SMA material or article having any one or more of (i) a critical stress for cross slip below a predetermined critical stress value; (ii) a yield stress below a predetermined yield stress value; (iii) a toughness greater than a predetermined toughness value; (iv) a strain at ultimate tensile strength (UTS) greater than a predetermined value, (v) a UTS/yield strength ratio below a predetermined value, or (vi) a Voce saturation stress below a predetermined value is used. Such predetermined values may be established in any suitable manner, such as by selecting such stress-strain values of similar SMA material that have performed well in fatigue testing.

Values for critical stress for cross slip, yield strength, toughness, strain at ultimate tensile strength (UTS), UTS to yield strength ratio, or Voce saturation stress may be determined in any suitable manner. For example, critical stress for cross slip may be determined (i) from the intersection of tangent lines of transitions from a plot of strain hardening $\Theta$ ($\delta\sigma_P/\delta\varepsilon_P$) versus plastic stress ($\sigma_P$); (ii) from mathematical solution of equations describing the transitions from a plot of rate of strain hardening $\Theta$ ($\delta\sigma_P/\delta\varepsilon_P$) versus plastic stress ($\sigma_P$); (iii) the intersection of tangent lines of transitions from a plot of log-log plot of rate of strain hardening $\Theta$ ($\delta\sigma_P/\delta\varepsilon_P$) versus plastic strain ($\varepsilon_P$); (iv) from mathematical solution of equations describing the transitions from a plot of log-log plot of rate of strain hardening $\Theta$ ($\delta\sigma_P/\delta\varepsilon_P$) versus plastic strain ($\varepsilon_P$); or (v) the like.

A production SMA article may be selected as having, or predicted to have, superior fatigue resistance by subjecting a surrogate SMA article to stress-strain testing to identify whether the surrogate article exhibits properties predictive of superior fatigue resistance.

The surrogate article may be subjected to uniaxial stress-strain testing to determine whether the article exhibits one or more of (i) a critical stress for cross slip below a predetermined critical stress value; (ii) a yield stress below a predetermined yield stress value; (iii) a toughness greater than a predetermined toughness value; (iv) a (UTS) greater than a predetermined strain at ultimate tensile strength (UTS) value, (v) a UTS to yield strength ratio greater than a predetermined UTS to yield strength ratio value, or (vi) a Voce saturation stress below a predetermined Voce saturation stress value. If the surrogate article meets one or more, two or more, three or more, four or more, or all of the conditions, the production article corresponding to the surrogate article may be used with the prediction of superior fatigue resistance.

In embodiments, the surrogate article is preloaded prior to uniaxial stress-strain testing. The degree of preloading may be a degree of preloading to which the production article may be preloaded. In embodiments, the surrogate article is preloaded from about 5% to about 10%. It will be understood that if the article is configured to expand, preloading may comprise compressing the article. In embodiments, the surrogate article is not preloaded prior to uniaxial stress-strain testing.

The SMA materials and selection methods described herein may be used in any suitable article. In embodiments, the SMA material forms a structural scaffold of an implantable medical device or a component thereof. Examples of implantable medical devices or components of implantable medical devices for which it may be desirable to include SMA material include heart valves, stents, vascular grafts, aneurysm clips, suture clips, anti-embolic filters and shields and anchoring and fixation elements for soft and hard tissues. Such devices and components are typically compressed or deformed prior to delivery to obtain a low profile for implantation and then expand during or following delivery (e.g., due to change in temperature). Subsequently, the device may be recompressed to facilitate recapture to enable repositioning post-deployment or partial deployment.

While the results presented in the Examples below were from uniaxial stress-strain data regarding nitinol, the concepts identified and presented herein may be extrapolated to other SMAs. Examples of SMAs for which the concepts presented herein may apply include alloys containing gold-cadmium, silver-cadmium, copper-aluminum-nickel, copper-tin, copper-zinc, copper-zinc-silicon, copper-zinc-tin, copper-zinc-aluminum, iron-platinum, manganese-copper, iron-manganese-silicon, platinum alloys, copper-nickel-aluminum, copper-nickel-gadolinium, nickel-iron-gadolinium, titanium-palladium, nickel-titanium-niobium, nickel-gadolinium-gadolinium, nickel-titanium (nitinol), and the like.

In embodiments, the SMA may be subjected to thermo-mechanical processes to obtain a desired shape memory configuration. For example, the material may be heat-treated or cold worked. In embodiments, the SMA is wrought. For example, the SMA may be drawn as a tube or wire, rolled into a sheet, plate or ribbon, or the like.

In embodiments, the shape memory material described herein is nitinol. Nitinol may have any suitable atomic percentage of nickel and titanium. General requirements for nitinol composition and allowable trace elements are defined in the ASTM standard, ASTM F2063. Often, nitinol has roughly equiatomic percentages of nickel and titanium with nickel content typically between 49 and 51 atomic percent, such as 49% Ni/51% Ti, 50% Ni/50% Ti, 51% Ni/49% Ti or the like.

It was surprisingly found that fatigue test articles fabricated from slightly smaller diameter heat-drawn nitinol tubes outperformed fatigue test articles fabricated from slightly larger diameter heat-drawn nitinol tubes by a factor of 3× at $P_{0.5}$ (projected 50% fracture and 50% run out) at 10 million cycles.

Studies were performed to identify reasons for superior fatigue performance of the fatigue test articles fabricated from tube processed with a heat treatment regimen Process A versus Process B where both processes A and B were executed on a common tube size. Studies were performed to identify reasons for superior fatigue performance of the fatigue test articles fabricated from the slightly smaller diameter tubes relative to fatigue test articles fabricated from the slightly larger diameter tubes. Based on these studies, a model was developed to successfully predict the rank order of fatigue performance of specimens extracted from articles fabricated from tubes of varying diameters subjected to varying heat treatments. While based on a foundation of classical physical and mechanical metallurgy, this model is unconventional in that it focuses primarily on the plastic portion of the engineering stress-strain curve and dispenses with the elastic and superelastic or pseudoelastic (SE) 'flag' portion. One interesting counter-intuitive finding is that increased ductility, rather than increased strength (as conventional wisdom would predict), is important for fatigue resistance of self-expanding devices fabricated from shape memory material such as nitinol.

The purpose of this study was to investigate whether quantities derived from uniaxial stress-strain data acquired from surrogate heat-treated nitinol tube specimens can be used to predict relative fatigue performance of individual fatigue test articles extracted from production articles fabricated from the same tubing as the surrogate specimens.

The plastic flow behaviour of both as-drawn and heat-treated nitinol tubes have been characterized. Descriptive metrics (plastic flow properties) have been identified; different permutations of tube size and heat-treatment result in different flow stress and plastic flow behaviour. Log-log plots of true stress vs. true strain for nitinol tubes do not follow a simple power-law relationship: $\sigma=K\varepsilon^n$; instead, they exhibit dual-sloped plastic flow behaviour irrespective of their heat-treated condition. Ludwigson: $\sigma=K_1\varepsilon^{n1}+\exp(K_2+n_2\varepsilon)$ and Voce: $\varepsilon=1/n \ln((\sigma_s-\sigma)/\kappa)$ equations have been used to accurately describe the observed plastic flow and strain-hardening behaviour ($R^2 \approx 1$).

The rate of strain hardening has been explored using log $\Theta$ ($\delta\sigma_P/\delta\varepsilon_P$) versus log EP plots and $\Theta$ ($\delta\sigma_P/\delta\varepsilon_P$) versus plastic stress $\sigma_P$ plots. Three classically-defined flow regimes have been identified, namely, Stages I, II and III. Stage I flow is ill-defined for all specimens studied in this analysis as evidenced by the very large negative $n_2$ values (rate of decay of the $\Delta$ term=$\exp(K_2+n_2\varepsilon)$ in the Ludwigson equation. However, Stage II is well defined. Stage I therefore constitutes that behaviour immediately preceding Stage II. Values derived from Stage I are not drawn on for comparative purposes.

Critical stress and strain values marking the transition between Stages II and III flow have been derived. The critical stress and strain values represent the transition from a slip regime involving edge dislocations to one which allows dislocations to cross-slip onto adjacent planes via a screw-dislocation mechanism. In general, for most conventional engineering metals and alloys those factors that act to suppress cross-slip tend to increase the resistance to fatigue failure, i.e. increase fatigue strength. For preloaded nitinol fatigue test specimens, higher fatigue strength correlates with lower values of critical stress for cross-slip, and extended ductility and toughness.

Based on the studies presented herein, it is believed that upon loading prior to fatigue cycling e.g., crimping or recapture of self-expanding production articles, stress concentrations develop at plastic strain inhomogeneities associated with microstructural features, surfaces, and interfaces. Microstructures that act to concentrate plastic strain or that result in an inhomogeneous distribution of plastic strains lead to undesirable local stress concentrations and large slip offsets at surfaces and interfaces. Surfaces may be at the surface of the component, may be free surfaces or microstructural interfaces in the bulk of the device, or the like. As a consequence, post-crimp, self-expanding nitinol production articles typically possess a population of pre-nucleated sub-critical flaws. In this context, since the crack nucleation stage is essentially truncated, the ability of the matrix to resist crack growth is favoured by those microstructures that promote ductility and toughness which act to reduce stress concentrations.

This approach does not require the individual contributions of microstructural contributions such as texture, precipitation hardening, and grain size to be directly assessed and summed. Instead, data is acquired directly from uniaxial stress-strain data thereby dispensing with a priori knowledge of for example Taylor M-factors and precipitate size and distribution (in this particular context not to be confused with oxide or oxy-carbide inclusion size and distribution), and mean grain size. Accordingly, this approach minimizes or eliminates the need for metallurgical cross sectioning, grinding and polishing specimen preparation, diffraction measurements, scanning electron microscopy (SEM), transmission electron microscopy (TEM) or other sophisticated analytical techniques and instrumentation. The approach described herein provides a means of predicting the rank order of the displacement-controlled fatigue performance of articles based on parameters describing their plastic flow behaviors acquired from uniaxial tensile testing of the heat-treated tubing or other wrought sections from which they are derived.

The values of various parameters have been determined from Ludwigson and Voce law fits of plastic flow curves plus a combination of log $\Theta$ ($\delta\sigma_P/\delta\varepsilon_P$) versus log $\varepsilon_P$ plots and $\Theta$ ($\delta\sigma_P/\delta\varepsilon_P$) versus plastic stress $\sigma_P$ plots.

Correlation of plastic flow parameters derived from uniaxial stress-strain plots with fatigue performance facilitates prima facie prediction of fatigue performance as a function of tube diameter and wall thickness plus heat-treatment. One working hypothesis implicates the extent of plastic crack-tip blunting as a primary mechanism dictating fatigue performance of nitinol devices as observed in displacement-controlled fatigue testing of test specimens extracted from the frames. Another working hypothesis implicates plastic strain as the controlling parameter in each stage of fatigue, such that microstructures that homogenously distribute strain are desired, whereas microstructural features that concentrate plastic strain or that result in an inhomogeneous distribution of plastic strains lead to undesirable local stress concentrations and large slip offsets at surfaces and interfaces and accordingly, inferior fatigue performance.

For reasons of practicality, the mechanical properties (uniaxial stress-strain relation) of production articles fabricated from processed nitinol tubes are derived using surrogate test specimens. Tube test specimens are heat-treated in a manner commensurate with the thermal processing schedule associated with the thermo-mechanical shape-setting of the articles. The tube specimens are typically subjected to a preload cycle to a prescribed strain level and subsequently unloaded to reveal their superelastic (SE) behaviour i.e. loading and unloading plateau stresses prior to being pulled to failure. Mechanical properties of the tubes may be established using specimens fabricated from the tube, for example laser-cut dog bones specimens.

Strain-displacement relationships for the articles are derived using superelastic finite element analysis (FEA). FEA is employed to characterize the stress-strain response of the articles during simulated in vivo loading, and likewise for the purposes of establishing strain-displacement relationships defining boundary conditions for in vitro bench testing e.g. fatigue testing. The FEA employs a user-defined material subroutine (UMAT), the UMAT inputs comprise mechanical properties extracted from the elastic and superelastic (SE) or pseudoelastic 'flag' region of the engineering stress-strain relation up to the so-called martensite modulus region. Because the SE flag region is of primary importance for the purposes of FEA modeling, the plastic stress-strain curve beyond the so-called martensite modulus typically receives little or no scrutiny.

A difference in fatigue performance was observed for fatigue specimens processed using two different heat treatments Process A and Process B. A preliminary survey of tensile stress-strain data was completed comparing tubes heat-treated per Process A versus a Process B. Tubes processed via both processes A and B were heat-treated to obtain a low austenite finish temperature ($A_f$) material condition of 17±2° C. Uniaxial tensile testing was performed in general agreement with ASTM E8 and ASTM 2516. The test temperature was maintained at 37±2° C. (ASTM 2516 indicates 22±2° C.). An engineering strain rate of $10^{-4}\cdot\text{sec}^{-1}$ was employed to avoid adiabatic effects. Specimens were pre-loaded equivalent to 6% or 8% strain prior to unloading to zero and re-loading to failure (ASTM 2516 indicates 6% only). Upper plateau stress at 3.0% strain; lower plateau stress at 2.5% strain; strain to failure; and ultimate tensile stress (UTS) were recorded, refer to Table 1B. It was concluded that overall the mechanical properties of samples in both test groups were typical for superelastic nitinol tubing used in the manufacture of self-expanding medical devices. Based on these results it was assumed that the monotonic mechanical properties of the material from which the tubes are fabricated and manufactured into final tubing by and heat-treated using Process B processing was equivalent to properties established using Process A processing. Inspection of Table 1B reveals a small difference in UTS between the specimens processed using Process A versus those processed using Process B of approximately 5%. Since conventional wisdom would suggest enhancing the strength of SMAs would promote reversible twinning and detwinning and reduce the propensity for irreversible plastic deformation caused by permanent dislocation slip, the observation that the lower strength population albeit by only a small margin (specimens processed using Process A) exhibited superior fatigue performance versus those specimens processed using Process B was counter intuitive.

TABLE 1B

Uniaxial tensile test results, mean upper plateau stress (UPS), mean lower plateau stress (LPS), mean UTS, and mean strain at failure for surrogate tube tensile test specimens heat treated using Process A and Process B. The parenthetical 6% and 8% denote the first cycle preload.

| Population Identity | Mean UPS MPa @ 3.0% strain | Mean LPS, MPa @ 2.5% strain | Mean UTS (MPa) | Mean Strain to failure (%) |
|---|---|---|---|---|
| Process A (6%) | 410 | 165 | 1161 | 31 |
| Process A (8%) | 421 | 109 | 1182 | 23 |
| Process B (6%) | 421 | 190 | 1218 | 22 |
| Process B (8%) | 418 | 105 | 1220 | 25 |

Results of uniaxial tensile tests comparing Process A heat-treatment versus Process B heat-treatment schedules are presented in Table 1B. All tubes were heat-treated to obtain low austenite finish ($A_f$) transformation temperature (17±2° C.) material conditions, testing was performed in general agreement with ASTM E8 and ASTM 2156 (Test temperature 37±2° C., engineering strain rate $10^{-4}\cdot\text{sec}^{-1}$).

A comparison of the full stress strain plots from which the data in Table 1B was acquired revealed some subtle differences in trajectory and shape of the two sets of post-yield stress-strain curves (Process A versus Process B). This observation combined with the observation that the lower strength population exhibited superior fatigue performance versus those specimens processed using Process B provided the impetus for further scrutinizing the flow stress behavior of as-drawn and heat-treated nitinol tubes.

The remainder of this report focuses on differences in flow stress behavior of (i) as-drawn nitinol tubes (three sizes small diameter, mid diameter and large diameter) and (ii) heat-treated nitinol tubes and their plastic flow behavior.

The production articles are fabricated from approximately equiatomic (50 atm. % Ni+50 atm. % Ti) nitinol tubing. All tubing complies with requirements of ASTM F2063-05 (ASTM F2063 Standard Specification for Wrought Nickel-Titanium Shape Memory Alloy for Medical Devices and Surgical Implants). Raw ingot material is processed to incrementally reduce its wrought section; large section billets are swaged into round sections and gun drilled to yield a 'hollow'. Hollows are reduced in gross section by tube sinking (without a mandrel). Final drawing into finished tubing is completed at a later point in time. The tube typically receives a 30-40% cold work reduction during the last drawing step. The amount of cold work combined with any final annealing steps dictate the mechanical properties of the as-drawn tube. The finished tube is then processed into production articles.

Tube Sizes

The subject production articles are manufactured using net-common processing routes including tube drawing, laser cutting, thermo-mechanical shape-setting, and electropolishing. The target nominal and austenite finish temperature ($A_f$) tolerance is the same for all production articles (22±5° C.).

TABLE 2B

Tube size (diameter and wall thickness) plus nominal cross-sectional area and heat treatment designation (Process) for each article.

| Article | Heat Treatment Designation | Diameter | Wall Thickness | Nominal Cross-Section Area |
|---|---|---|---|---|
| A | Process A | mid | a | j |
| B | Process B | mid | a | j |
| C | Process C | mid | a | j |
| D | Process D | mid | a | j |
| E | Process E | mid | a | j |
| F | Process F | small | a | i |
| G | Process G | large | b | k |
| H | Process H | small | a | i |

In Table 2B, i<j<k, Process F is similar but not identical to Process H.

This report focuses on the flow stress behaviour of (i) the as-drawn nitinol tubes (three sizes small, mid and large); and (ii) heat-treated nitinol tubes (three sizes small, mid and large). The permutations of tube sizes and heat-treatment considered in this study are provided in Tables 3B-5B below.

TABLE 3B

Summary of the raw tube specimen data analyzed (no heat treatment), strain rate $1.25^{-2}\cdot\text{s}^{-1}$, test temperature 22 ± 2° C.

| Diameter Ø | Wall Thickness | Heat Treatment | Pre-Strain (%) | Mean $A_f$ (° C.) | Number of Replicates (n) |
|---|---|---|---|---|---|
| small | a | — | 6 | −7 | 4 |
| mid | a | — | 6 | −9 | 16[a] |
| large | b | — | 6 | −11 | 6[b,c] |

[a]Qty. 16 represents four (4) populations of n = 4 replicates.
[b]Qty. 6 represents two (2) populations of n = 3 replicates, one population (n = 3) were excluded due to test artifacts.
[c]Mechanical properties of the large diameter tubes were derived from laser-cut dogbones specimens due to force capacity limitations of available load cells.

TABLE 4B

Summary of the heat-treated tube data used to compare the Process A and Process B heat treatments, strain rate $10^{-4} \cdot s^{-1}$, test temperature $37 \pm 2°$ C.

| Diameter | Wall Thickness | Heat Treatment | Pre-Strain (%) | Mean $A_f$ (° C.) | Number of Replicates (n) |
|---|---|---|---|---|---|
| mid | a | Process A | 6 | 17 | 5 |
| mid | a | Process A | 8 | 17 | 4 |
| mid | a | Process B | 6 | 17 | 5 |
| mid | a | Process B | 8 | 17 | 4 |

TABLE 5B

Summary of heat-treated tube specimen data analyzed (variable tube dimension, heat treatment, and $A_f$), strain rate $10^{-4} \cdot s^{-1}$, test temperature $37 \pm 2°$ C.

| Diameter Ø (mm) | Wall Thickness (mm) | Heat Treatment | Pre-Strain (%) | Mean $A_f$ (° C.) | Number of Replicates (n) |
|---|---|---|---|---|---|
| small | a | Process F | 6 | 17 | 5 |
| small | a | Process D | 6 | 19 | 5 |
| mid | a | Process F | 6 | 15 | 5 |
| large | b | Process F | 6 | 14 | 5 |
| mid | a | Process E | 6 | 23 | 5 |
| small | a | Process H | 6 | 17 | 2 |
| small | a | Process H | 6 | 22 | 2 |

Experimental Approach

Stress-strain plots of work-hardening metals especially those without a sharply defined yield stress may be approximated by the Ramberg-Osgood relation:

$$\varepsilon = \frac{\sigma}{E} + \alpha \frac{\sigma_R}{E}\left(\frac{\sigma}{\sigma_R}\right)^m \quad \text{[Eq. 4C]}$$

where α and m are dimensionless constants, $\sigma_R$ is a reference stress. If m is very large, then ε remains small until σ approaches $\sigma_R$, and increases rapidly when σ exceeds $\sigma_R$ such that $\sigma_R$ may be regarded as an approximate yield stress. In the limit as m becomes infinite, the plastic strain is zero when $\sigma<\sigma_R$, and is intermediate when $\sigma=\sigma_R$, while $\sigma>\sigma_R$ would result in an infinite plastic strain which is impossible. Accordingly, this limiting case describes a perfectly plastic response with a yield stress $\sigma_R$. If the deformation is sufficiently large for the elastic strains to be neglected, then the Ramberg Osgood equation can be solved for σ in terms of ε:

$$\sigma = C\varepsilon^n \quad \text{[Eq. 5C]}$$

where $$C = \sigma_R\left(\frac{E}{\alpha\sigma_R}\right)^n \quad \text{[Eq. 6C]}$$

and n=1/m which is referred to as the strain hardening exponent.

The more familiar form of Eq. 5C as given by Ludwik is defined by the simple power-law relationship attributed to Hollomon1:

$$\sigma = K\varepsilon^n \quad \text{[Eq. 7C]}$$

where σ, ε, K and n are the true stress, true plastic strain, the strength coefficient, and the strain hardening exponent respectively.

Figure 65:
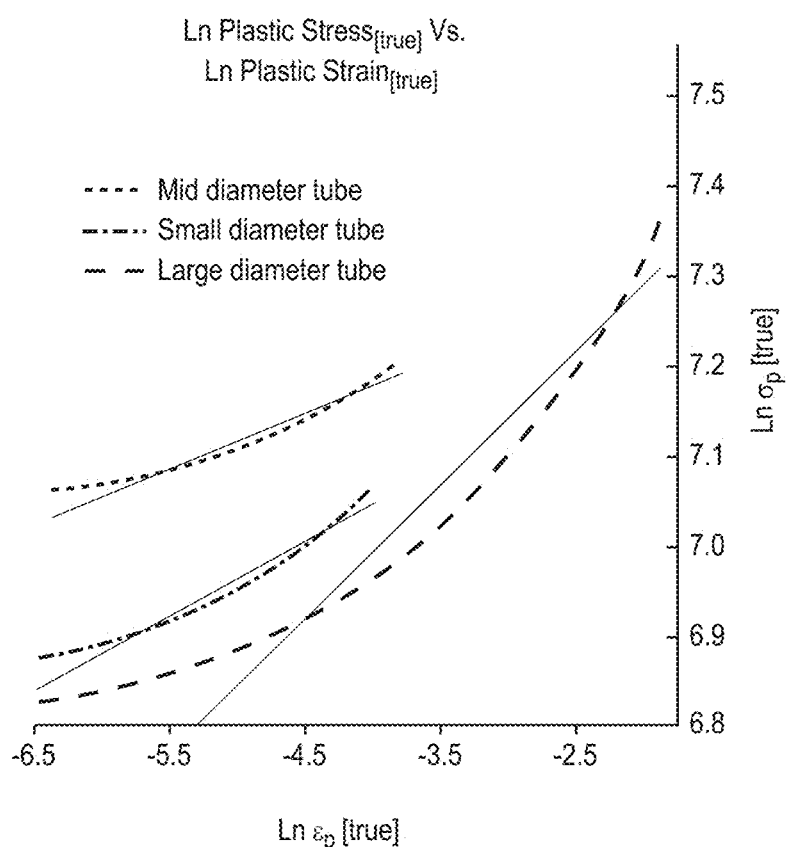
FIG. 65 is a log-log plot of true tensile stress and strain (normalized assuming zero strain at the yield point) for specimens of three different wrought as-drawn tube specimens with no heat-set thermal processing; the superimposed linear fits emphasize the non-linearity of these plots.

The flow behavior of many metals and alloys in the region of uniform plastic flow is described by this simple power-law fit, however, the log-log plots of true stress vs. normalized true strain reveals that equiatomic nitinol tube materials do not follow this simple power-law relationship. Instead, they exhibit dual-sloped plastic flow behavior irrespective of their heat-treated condition, refer to FIG. 65. A survey was undertaken to identify a more applicable equation to more accurately describe the dual-slope behavior exhibited by the nitinol tubes. The prime advantage of a well-fitting equation is that the parameters in it (which depend on material behavior) can be determined in a reproducible manner. A variety of alternative equations (other than the simple power law equation) have been derived as empirical laws. Parameters and constants in the various equations therefore do not necessarily possess inherent physical meaning, although they are effective at describing the measured range. In many cases, relationships correlating the fitting parameters and constants with physical properties and behaviour can be identified. Despite some recognized limitations, data fitting in this manner provides a consistent means of quantifying the flow behaviour and thereby provides a quantitative means of comparison. A number of different equations have been evaluated. $R^2$ values were used to determine how closely the function fits the experimental flow stress data. A $R^2$ value of 1 represents a perfect fit between the experimental data and the fit, whereas a value of 0 represents no statistical correlation between the data and the fit. The $R^2$ values for the various equations (often referred to as the goodness of fit) were computed as follows:

$$R^2 = 1 - \frac{\Sigma(Yi - Y'_i)^2}{\Sigma(Yi - \bar{Y})^2} \quad \text{[Eq. 8C]}$$

where Yi represents an individual data point value, Yi' represents the value obtained when the independent coordinate of this data point is input into the best-fit function. Therefore, Yi' represents the values of the data points projected onto the line of best fit (the ideal values). Y represents the average of the Yi values.

| | | |
|---|---|---|
| $\sigma = K\varepsilon^n$ | Hollomon | [Eq. 9C] |
| $\sigma = \sigma_o + K\varepsilon^n$ | Ludwik | [Eq. 10C] |
| $\varepsilon = \varepsilon_o + K\sigma^n$ | Swift | [Eq. 11C] |
| $\varepsilon = \frac{1}{n}\ln\left(\frac{\sigma_s - \sigma}{k}\right)$ | Voce | [Eq. 12C] |
| $\sigma = K_1\varepsilon^{n_1} + \exp(K_2 + n_2\varepsilon)$ | Ludwigson | [Eq. 13C] |

The Ludwigson model provides an accurate description of the flow curves with $R^2$ values typically greater than 0.99.

Figure 66:
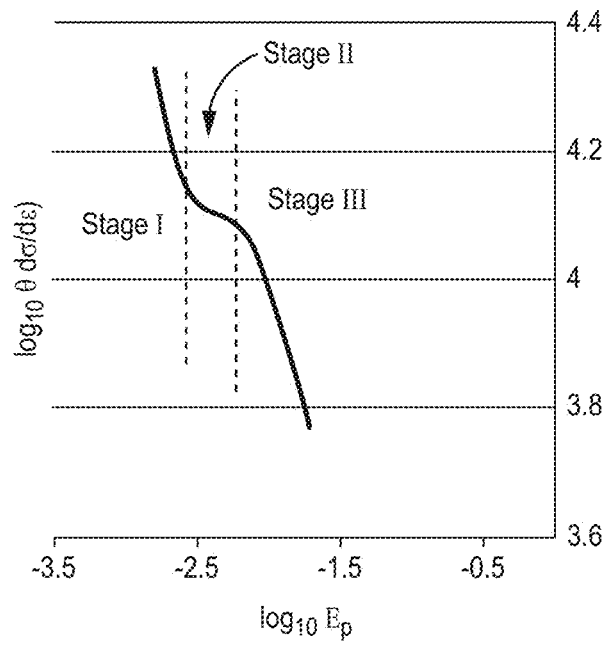
FIG. 66 is a plot of the rate of strain hardening log $\Theta$ ($d\sigma_P/d\varepsilon_P$) versus log $\varepsilon_P$ of a representative example from a wrought as-drawn tube specimen with no heat-set thermal processing.

Plots of the rate of strain hardening Θ ($\delta\sigma P/\delta\varepsilon_P$) versus $\varepsilon_P$ on log-log axes was used to identify different stages of plastic flow; a representative example from the current work is shown in FIG. 66. The flow curves for nitinol exhibit three distinct regions where changes in the different flow regimes coincide with abrupt changes in slope. The three stages of work hardening may be characterized as follows: (i) the initial transient portion where Θ decreases rapidly; (ii) a stage where Θ decreases gradually with $\varepsilon_P$ (Stage II); and (iii) a stage where Θ decreases due to the onset of dynamic recovery (Stage III).

By inspection, the Ludwigson model [Eq. 12C] comprises of two discrete terms, $K\varepsilon^N$ the Holloman (Ludwik) relation and a second delta term, $\Delta=\exp(K_2+n_2\varepsilon)$ [Eq. 13C]. The Holloman function provides a good fit for the higher strain flow behaviour whereas the Δ function provides a better description for the lower strain flow behaviour. The combination of these two terms therefore provides a good fit of the experimental data by preferentially fitting the Holloman function to the higher strain data and subsequently using the Ludwigson delta function to make up the difference between the lower strain data and the Holloman fit.

The transition from stage II to stage III flow is defined by a critical strain ($\varepsilon_c$). The critical strain delineates that strain below which planar slip is prevalent and above which cross slip becomes dominant based on the rate of strain hardening. The critical strain was derived by defining it as that location on the true plastic stress versus true strain curve where the value of delta function is less than an arbitrary small value of two percent (2%) of the value of the Holloman function, or:

$$\frac{e^{K_2+n_2\varepsilon}}{K_1\varepsilon^n} = 0.02 \qquad [\text{Eq. 14C}]$$

One limitation of a strain based approach for deriving plastic flow parameters is that the values of the constants can be sensitive to strain history. Since the flow stress is normally defined by the present state of a material and not by the path of attaining that state, the influence of the strain history sensitivity can be avoided altogether if the derivative Θ ($d\sigma_P/d\varepsilon_P$) is plotted versus true plastic stress $\sigma_P$, this approach was first discussed by Mecking and Lucke (H. Mecking and K. Lucke, Acta Metall. 17 (1969) 279).

The tube data was fitted with good agreement using the Voce equation ($R^2$ close to 1), the $d\sigma/d\varepsilon$ vs. $\sigma_P$ plot of the Voce-fitted data yields a straight line, hence, by solving the Voce equation [Eq. 12C] for strain [Eq. 2C] and substituting the derivative of the Voce equation (E. Voce, J. Inst. Metals, 74: 537 (1948)), the resulting equation is of a line with slope n and intercept −n·σs [Eq. 3C].

The Voce relation was solved to give values for the slope and the saturation stress as, the slope of the Voce plot n provides a consistent metric describing the slope of the linear portion of the flow curve equivalent to Stage III in plots of dσ/dε vs. $\sigma_P$. The value of n represents the rate of decay of strain hardening due to dynamic recovery upon reaching saturation.

Figure 67:
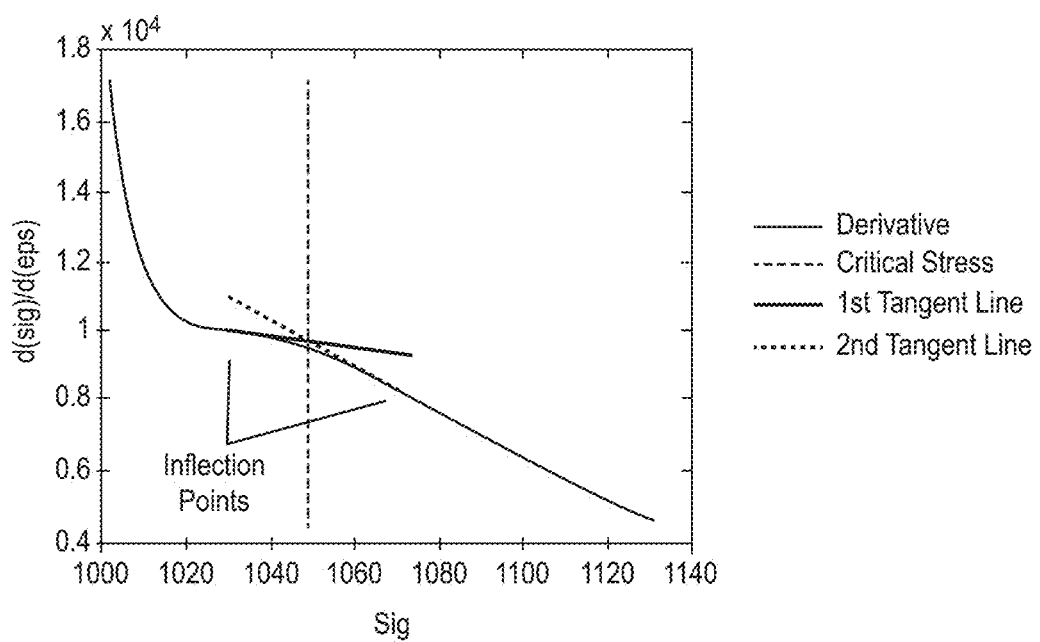
FIG. 67 is a plot of $\Theta$ ($d\sigma_P/d\varepsilon_P$) versus plastic stress $\sigma_P$ showing tangent construction lines used to derive the critical stress sc.

Critical stress ($\sigma_c$) values analogous to the critical strain values identified in the analyses were computed to identify the transition stress from stage II to stage III flow. In analogy with the critical strain, the critical stress delineates that stress below which planar slip is prevalent and above which cross slip becomes dominant based on the rate of strain hardening On a plot of the Θ ($d\sigma_P/d\varepsilon_P$) vs. true stress, tangent lines where constructed at inflection points found from the minima of the third derivative, the location of the critical stress is defined by the intersection of two tangent lines (see, FIG. 67).

Summary

The Ludwigson equation can be used to successfully describe the dual slope work hardening behaviour of equi-atomic nitinol tubes, in the as-drawn and heat-treated conditions.

Plots of rate of strain hardening expressed in terms of log Θ ($d\sigma_P/d\varepsilon_P$) versus log $\varepsilon_P$ can successfully delineate different flow regimes e.g. Stages II and III for polycrystalline nitinol specimens.

Plots of rate of strain hardening expressed in terms of Θ ($d\sigma_P/d\varepsilon_P$) versus plastic stress $\sigma_P$ can successfully delineate different flow regimes e.g. Stages II and III.

Critical strain values can be derived by defining the location on the true plastic stress versus true strain curve where the value of Ludwigson delta term is less than an arbitrary small value e.g. two percent (2%) of the value of the Holloman term.

Plots of rate of strain hardening expressed in terms of Θ ($d\sigma_P/d\varepsilon_P$) versus plastic stress $\sigma_P$ and log-log plots of Θ ($d\sigma_P/d\varepsilon_P$) versus plastic stress $\varepsilon_P$ can be used determine critical stress and strain for cross slip.

Numerical solutions and graphical tangent line constructions can be employed to identify values of critical stress and strain for cross slip.

The Voce equation can be used to identify values of saturation stress as and the slope of Stage III plastic flow given by nv.

Collectively, data gathered from a combination of log Θ ($d\sigma_P/d\varepsilon_P$) versus log $\varepsilon_P$ plots; Θ ($d\sigma_P/d\varepsilon_P$) versus plastic stress $\sigma_P$ plots; and Voce law fits can be used to describe and discriminate between differences in flow properties.

Data Analysis

Comparison of the Stress-Strain Relations

Figure 68:
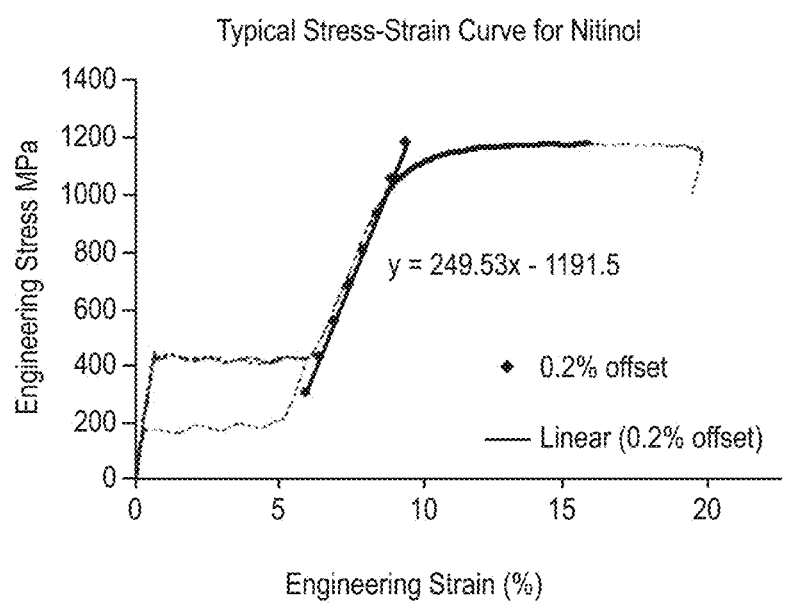
FIG. 68 is a plot of a typical tensile stress-strain plot for a heat-treated worked wrought specimen. The plastic region of interest is bounded by the yield stress and UTS, the data defined by the dotted line is discarded once the yield point has been identified.

FIG. 68 shows a typical tensile stress-strain plot for a heat-treated equiatomic nitinol tube specimen. The specimen is loaded to a prescribed pre-load (6% or 8%). Data derived from the portion defined by the bold solid line is employed for the purposes of this study. The data defined by the dotted line is discarded once the yield point has been identified.

The limit of the elastic range cannot be defined exactly, however, it can be approximated by a value of stress below which the amount of irreversible plastic deformation is considered negligible, and above which the plastic deformation predominates (This holds true for conventional materials but may be compromised since some plasticity may occur in the so called martensite modulus region, i.e. the martensite modulus region is not linearly elastic). Ignoring any plasticity in the modulus region, the transition between elastic and plastic behaviour occurs gradually for equiatomic nitinol, i.e., there is no well-defined yield as observed for many engineering steel grades. The threshold for this transition is defined as the yield or flow stress. Once the yield stress has been reached, the permanent deformation occurs by means of two processes, slip or glide and mechanical twinning (twinning in this context refers to mechanical deformation twins and not crystallographic twins such as those discussed in the context of the superelastic behavior). A 0.2% offset has been employed to define the yield stress, the ultimate tensile strength was derived from filtered data and is defined as the maximum stress value achieved during the tensile test. The data between an offset yield stress (e.g. 0.2%, 0.02%) and the UTS defines the plastic region.

Matlab Analysis

Each data set (refer to Tables 3B-4) was truncated to remove all of the pre-load cycle and leave only the stress-strain data from the start of the superelastic loading plateau to fracture. The data files were formatted uniformly with engineering stress and strain in two separate columns each data pair populating their own spreadsheet. A script was written in Matlab (version R2011b) to extract discriminating required plastic flow parameters. The Matlab code facilitated the batch processing of the data such that an indefinite number of data sets could be analyzed simultaneously in a consistent manner. Any suitable programming code may be used to facilitate batch processing and consistent data analyses.

Results

According to the Ludwigson model, at low strain levels there is a deviation Δ from the Hollomon relation. At a high strain level the Holloman relation describes the behaviour whereas at low strain levels the Δ term is more descriptive.

Figure 69B:
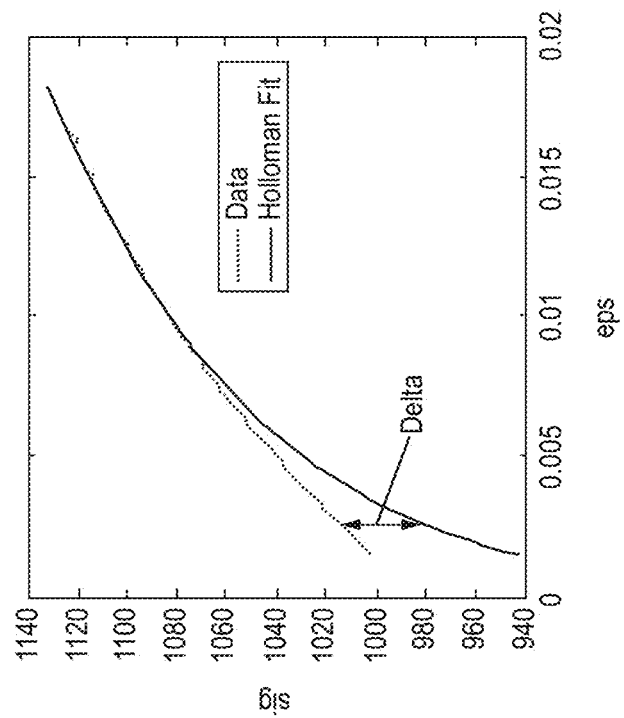
Figure 70:
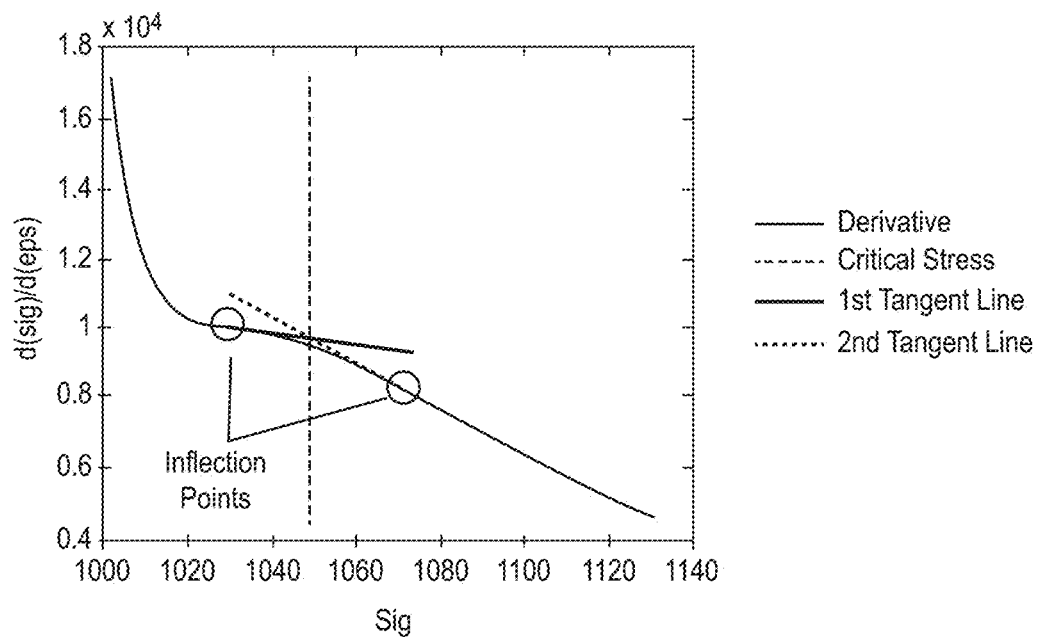
FIG. 70 is a plot of $\Theta$ ($d\sigma_P/d\varepsilon_P$) versus plastic stress $\sigma_P$ showing tangent construction lines used to derive the critical stress ac.

The transient threshold value of strain $\varepsilon_c$ can be defined as the strain at which the Δ term becomes very small in comparison with the Hollomon/Ludwik term. This critical strain value $\varepsilon_c$ can be evaluated by giving the ratio of the Δ term to the Hollomon term an arbitrary small value, in this case 0.02 (see FIGS. 69A and 69B). Once the critical strain $\varepsilon_c$ is found it is then possible to establish the corresponding critical stress defined by $\sigma = K_1 \varepsilon^{n1} + \Delta$ [Eq. 1F]. The values for critical stress have been derived from both a graphical solution of rate of strain hardening $\Theta$ ($d\sigma_P/d\varepsilon_P$) versus plastic stress $\sigma_P$ plots in the manner shown in FIG. 66 and FIG. 70, and by a direct mathematical solution from the Ludwigson fitted data per Eq. 1F.

TABLE 6B

Summary of selected variables (mean values) for heat-treated tube specimen populations, the rows have been nominally ranked as a function of yield strength in ascending order.

| HT Process | Ø | Pre Load | $A_f$ (° C.) | $\sigma_Y$ (MPa) | $\sigma_{UTS}$ (MPa) | $\varepsilon_Y$ | $\varepsilon_U$ | UTS/$\sigma_Y$ | $E_m$ (MPa) | $U_T$ J·m$^3$ | $\sigma_c$ (MPa) |
|---|---|---|---|---|---|---|---|---|---|---|---|
| F | small | 6 | 19 | 880 | 1176 | 0.084 | 0.25 | 1.34 | 21532 | 164 | 969 |
| D | small | 6 | 19 | 885 | 1161 | 0.086 | 0.26 | 1.31 | 20353 | 177 | 970 |
| F | large | 6 | 14 | 895 | 1145 | 0.088 | 0.24 | 1.28 | 19525 | 150 | 991 |
| H | small | 6 | 20 | 923 | 1168 | 0.084 | 0.18 | 1.27 | 23527 | 104 | 998 |
| E | mid | 6 | 23 | 1048 | 1228 | 0.089 | 0.15 | 1.17 | 22336 | 72 | 1104 |
| F | mid | 6 | 17 | 1098 | 1262 | 0.091 | 0.14 | 1.15 | 22418 | 58 | 1150 |

TABLE 7B

Summary of selected variables (mean values) for 29 mm P1 and P2 heat treated tube specimen populations, each with a 6 and 8% pre-load on the first cycle prior to pulling to failure on the second cycle. Note the discrepancy in the UTS reported in Table 7B versus those values reported in Table 1B is associated with the more accurate selection of the peak tensile strength afforded by the MatLab code used to process the data reported in Table 7B.

| HT Process | Ø | Pre Load | $A_f$ (° C.) | $\sigma_Y$ (MPa) | $\sigma_{UTS}$ (MPa) | UTS/$\sigma_Y$ | $\varepsilon_Y$ | $\varepsilon_U$ | $E_m$ (MPa) | $U_T$ J·m$^3$ | $\sigma_c$ (MPa) |
|---|---|---|---|---|---|---|---|---|---|---|---|
| A | mid | 6 | 17 | 939 | 1161 | 1.24 | 0.085 | 0.18 | 23276 | 98 | 1024 |
| A | mid | 8 | 17 | 961 | 1179 | 1.23 | 0.089 | 0.16 | 24542 | 77 | 1025 |
| B | mid | 8 | 17 | 996 | 1218 | 1.22 | 0.088 | 0.16 | 24878 | 79 | 1077 |
| B | mid | 6 | 17 | 1014 | 1218 | 1.20 | 0.087 | 0.15 | 22720 | 71 | 1092 |

TABLE 8B

Summary of selected variables (mean values) for "raw" as-drawn tube specimen populations (with no post-draw aging heat-treatment), the rows have been nominally ranked as a function of yield strength in ascending order.

| HT Process | Ø | Pre Load | $A_f$ (° C.) | $\sigma_Y$ (MPa) | $\sigma_{UTS}$ (MPa) | UTS/$\sigma_Y$ | $\varepsilon_Y$ | $\varepsilon_U$ | $E_m$ (MPa) | $U_T$ J·m$^3$ | $\sigma_c$ (MPa) |
|---|---|---|---|---|---|---|---|---|---|---|---|
| — | large | 6 | −11 | 958 | 1127 | 1.18 | 0.098 | 0.24 | 15160 | 164 | 1021 |
| — | small | 6 | −7 | 929 | 1176 | 1.27 | 0.087 | 0.19 | 21546 | 105 | 1024 |
| — | mid | 6 | −9 | 1043 | 1224 | 1.17 | 0.093 | 0.16 | 18696 | 79 | 1107 |
| — | mid | 6 | −9 | 1069 | 1247 | 1.17 | 0.093 | 0.15 | 20982 | 63 | 1132 |
| — | mid | 6 | −9 | 1114 | 1275 | 1.14 | 0.094 | 0.14 | 21011 | 56 | 1164 |
| — | mid | 6 | −9 | 1155 | 1302 | 1.13 | 0.096 | 0.15 | 20098 | 65 | 1224 |

TABLE 9B

Summary of mean Ludwigson and Voce parameters for heat-treated tube specimens, the rows have been maintained in ranked order per Table 6 as a function of yield strength in ascending order.

| HT Process | Ø | Pre Load | $A_f$ (° C.) | $K_1$ | $n_1$ | $K_2$ | $n_2$ | $\sigma_{S[Voce]}$ (MPa) | $n_{[Voce]}$ |
|---|---|---|---|---|---|---|---|---|---|
| F | small | 6 | 19 | 1655 | 0.105 | 4.98 | −518 | 1190 | −61 |
| D | small | 6 | 19 | 1555 | 0.094 | 4.88 | −482 | 1168 | −56 |
| F | large | 6 | 14 | 1545 | 0.097 | 4.79 | −321 | 1158 | −50 |

TABLE 9B-continued

Summary of mean Ludwigson and Voce parameters for heat-treated tube specimens, the rows have been maintained in ranked order per Table 6 as a function of yield strength in ascending order.

| HT Process | Ø | Pre Load | $A_f$ (° C.) | $K_1$ | $n_1$ | $K_2$ | $n_2$ | $\sigma_{S[Voce]}$ (MPa) | $n_{[Voce]}$ |
|---|---|---|---|---|---|---|---|---|---|
| H | small | 6 | 20 | 1614 | 0.092 | 4.99 | −574 | 1209 | −62 |
| E | mid | 6 | 23 | 1567 | 0.067 | 4.83 | −598 | 1260 | −67 |
| F | mid | 6 | 17 | 1627 | 0.067 | 4.75 | −555 | 1309 | −69 |

TABLE 10B

Summary of mean Ludwigson and Voce parameters for 29 mm P1 and P2 heat treated tube specimen populations, each with a 6 and 8% pre-load on the first cycle prior to pulling to failure on the second cycle.

| HT Process | Ø | Pre Load | $A_f$ (° C.) | $K_1$ | $n_1$ | $K_2$ | $n_2$ | $\sigma_{S[Voce]}$ (MPa) | $n_{[Voce]}$ |
|---|---|---|---|---|---|---|---|---|---|
| A | mid | 6 | 17 | 1551 | 0.082 | 4.78 | −575 | 1189 | −73 |
| A | mid | 8 | 17 | 1585 | 0.081 | 4.82 | −598 | 1212 | −73 |
| B | mid | 6 | 17 | 1629 | 0.082 | 4.85 | −482 | 1263 | −64 |
| B | mid | 8 | 17 | 1616 | 0.078 | 4.83 | −525 | 1253 | −65 |

TABLE 11B

Summary of mean Ludwigson and Voce parameters for "raw" as-drawn tube specimen populations (with no post-draw aging heat-treatment), the rows have been maintained in ranked order per Table 8B as a function of yield strength in ascending order.

| HT Process | Ø | Pre Load | $A_f$ (° C.) | $K_1$ | $n_1$ | $K_2$ | $n_2$ | $\sigma_{S[Voce]}$ (MPa) | $n_{[Voce]}$ |
|---|---|---|---|---|---|---|---|---|---|
| — | large | 6 | −11 | 1679 | 0.135 | 5.11 | −47 | 1377 | −11 |
| — | small | 6 | −7 | 1631 | 0.096 | 4.96 | −461 | 1221 | −55 |
| — | mid | 6 | −9 | 1615 | 0.078 | 4.89 | −364 | 1299 | −44 |
| — | mid | 6 | −9 | 1653 | 0.077 | 4.85 | −403 | 1316 | −51 |
| — | mid | 6 | −9 | 1646 | 0.068 | 4.79 | −428 | 1345 | −53 |
| — | mid | 6 | −9 | 1654 | 0.063 | 4.76 | −382 | 1377 | −49 |

Fatigue Test Results

Figure 71:
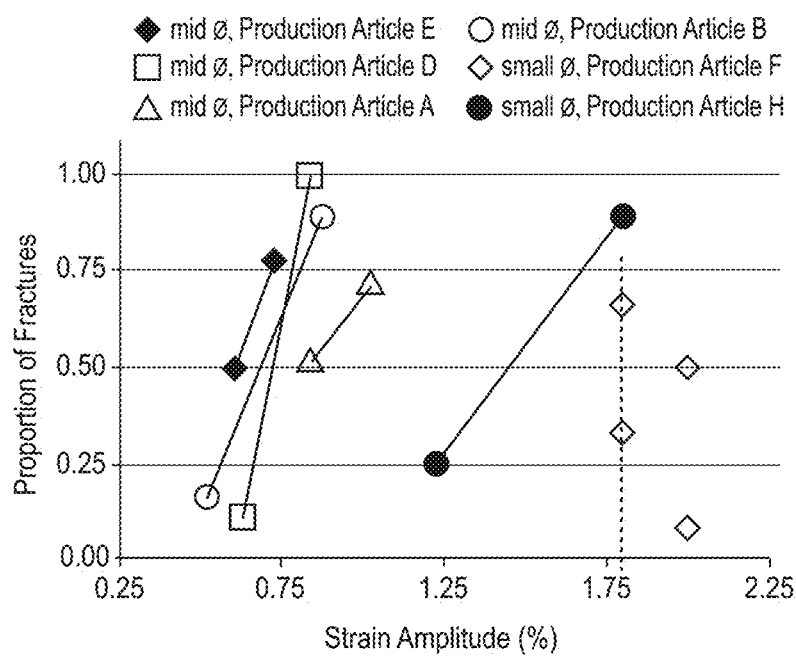
FIG. 71 is a plot of strain-life (displacement-controlled) fatigue data to 10 million cycles run-out for test specimens. The identity of specimen expressed by diameter and heat treatment process is shown. The vertical dashed line on the plot bisects the strain axis at 1.80% and defines the lower bound strain amplitude at which 50% of the Process H specimens fracture.

Strain-life (displacement-controlled) fatigue data is provided in FIG. 71, P0.5 values extrapolated from the data plotted in FIG. 71, are correlated with heat-treatment regime and plastic flow parameters (Table 12B).

The P0.5 fatigue strength values at 10 million cycles as provided in Table 12B were derived from the mid-point of the linear regression lines connecting the two end point data-sets, refer to FIG. 71. Each end point is the mean fracture proportion observed from testing at a given strain amplitude (or the average of slightly different strain amplitudes in cases where more than one strain amplitude level contributed to the establishment of an end point). The line between end points represents the predicted intermediate mean conditions. Specifically, the strain amplitude corresponding to a value of P=0.5 extrapolated from a given mean line is the predicted average test condition that would result in a fracture proportion of 50%, and is based on the assumption that the relationship between $\varepsilon_a$ vs. Probability is linear in the regime of this testing. The vertical dashed line on the plot of $\varepsilon_a$ vs. Probability (FIG. 71) bisects the strain axis at 1.80% and thereby defines the lower bound strain amplitude at which 50% of the Process H specimens fracture.

Specimens are extracted from production articles. Prior to testing, the production article goes through a conditioning process to emulate acute compressions and deformation that are anticipated prior to chronic use. The production article specimens were tested in a 37° C. phosphate buffered saline environment. Prior to cycling, all specimens were compressed to 5% strain and unloaded to the target mean strain (3.0% for all specimens) to ensure all specimens are cycled from the lower unloading plateau. The strain amplitude ranged from 0.4% to 2.0%.

Table 12B below compares fatigue strength as a function of differences in mean values of plastic flow properties.

TABLE 12B

Strain-life (displacement-controlled) P0.5 fatigue strength values run-out to 10M cycles for fatigue specimens extracted from production in rank order highest to lowest. Flow properties are derived from surrogate tube specimens heat-treated in a manner commensurate with the production articles which they represent. The flow property data for all populations surveyed has been derived from tube specimens subjected to a 6% first cycle preload prior to unloading a pulling to failure. Flow properties for Article H (Process H) are pooled values derived from a limited data set comprising of n = 2 17° C. $A_f$ specimens plus n = 2 22° C. $A_f$ specimens, the pooled $A_f$ is cited as a pooled mean of 20° C. rounded from 19.5° C. Fatigue Strength (FS) is expressed as alternating strain amplitude (%) at a specified cycle count, in this case 10M cycles.

| Specimen Identity | Tube Size | $A_f$ (°C.) | $P_{0.5}$ FS 10M | $\sigma_Y$ (MPa) | $\sigma_U$ (MPa) | $\sigma_U/\sigma_Y$ | $\varepsilon_{UTS}$ | $U_T$ J·m$^3$ | $\sigma_c$ (MPa) | $\sigma_{S[Voce]}$ (MPa) |
|---|---|---|---|---|---|---|---|---|---|---|
| Article F (Process F) | small | 19 | 1.80 | 880 | 1176 | 1.34 | 0.25 | 164 | 969 | 1190 |
| Article H (Process H) | small | 20 | 1.45 | 923 | 1168 | 1.27 | 0.18 | 104 | 998 | 1209 |
| Article A (Process A) | mid | 22 | 0.82 | 939 | 1161 | 1.24 | 0.18 | 98 | 1024 | 1189 |
| Article D (Process D) | mid | 21 | 0.72 | — | — | — | — | — | — | — |
| Article B (Process B) | mid | 21 | 0.68 | 1014 | 1218 | 1.20 | 0.15 | 71 | 1082 | 1263 |
| Article E (Process E) | mid | 23 | 0.61 | 1048 | 1228 | 1.17 | 0.15 | 72 | 1104 | 1260 |

Observations: Higher fatigue strength correlates well with extended ductility in terms of lower yield stress and lower critical stress, greater strain at UTS and greater toughness.

Conclusion: P0.5 displacement-controlled fatigue strength acquired from individual cells extracted from articles correlates well with the trending of parameters describing their plastic flow behaviors acquired from uniaxial tensile testing of the heat-treated tubing from which they are cut. Higher fatigue strength correlates with lower values of critical stress for cross-slip, a lower yield stress, and metrics which express extended ductility and toughness.

Discussion

Plastic strain is the controlling parameter in each stage of fatigue, microstructures that homogenously distribute strain are desired, Starke, E. A., and Lutjering G., "Cyclic Plastic Deformation and Microstructure", Fatigue and Microstructure, ASM Seminars, St. Louis, 1978, American Society for Metals, Metals Park, Ohio pp 205-243.

Any microstructural feature that concentrates plastic strain or that results in an inhomogeneous distribution of plastic strains leads to undesirable local stress concentrations and large slip offsets at surfaces, where "surfaces" refers to the area of contact between two different phases or states of matter, including those surfaces at the precipitate-matrix and oxide-matrix interfaces, and any interface such as those associated with different microstructures, precipitates, microstructural features, crystal structures, phases, voids, intrinsic and extrinsic defects and damage, and other microstructural aspects and features.

Fatigue Performance

Figure 72:
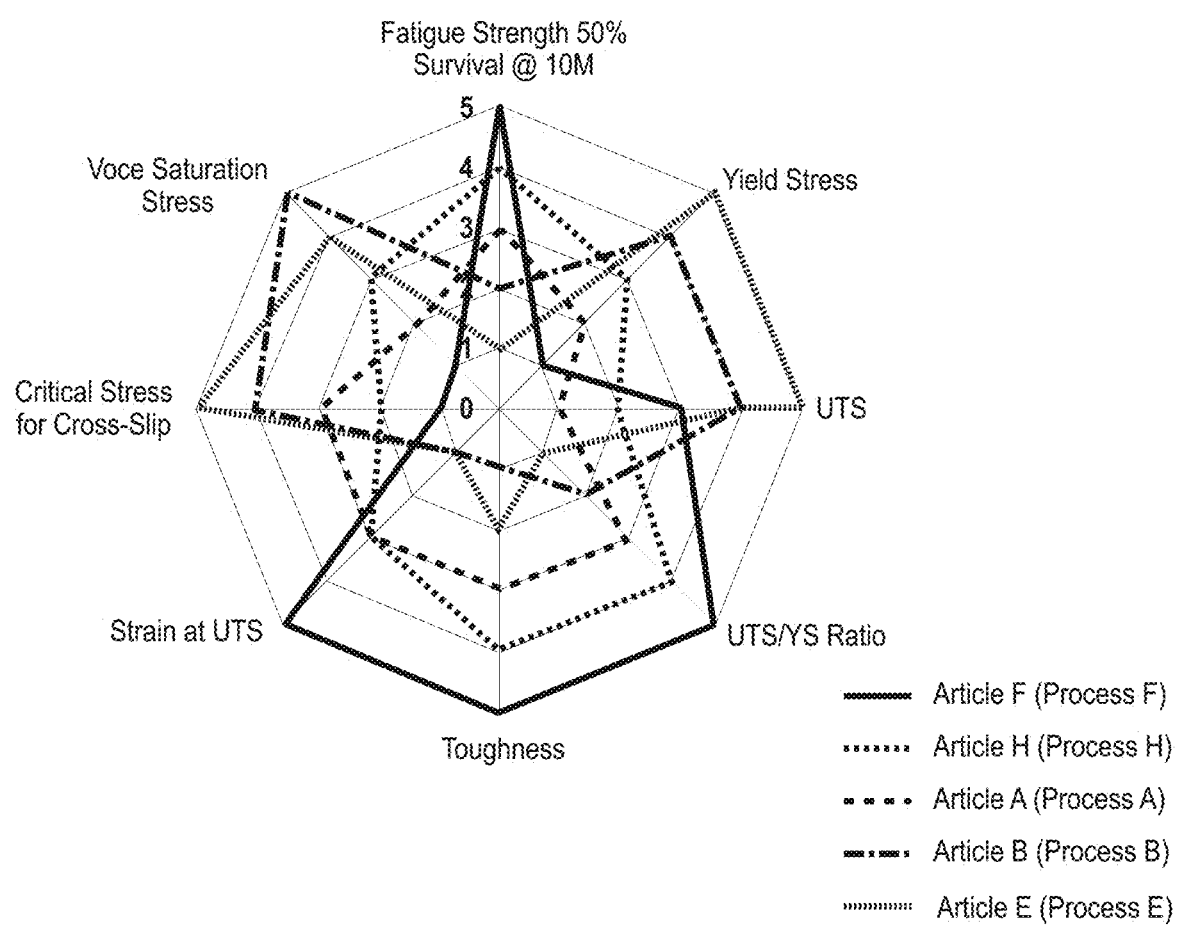
FIG. 72 is a spider plot of various stress-strain parameters and fatigue strength of a variety of tested articles. The spider plot is constructed using the simple ranking of the data reported in Table 12B by magnitude where 1=smallest value and 5=greatest value.

Those factors which affect work-hardening are also important drivers of fatigue performance, and material conditions which act to suppress cross-slip in general increase the resistance to fatigue failure, i.e. increase fatigue strength. The role of cross slip in fatigue has been recognized since early studies by McGrath and Thurston (1963), J. T. McGrath and R. C. A. Thurston, Trans. Metall. Soc. AIME. 227, 645 (1963), according to Ashby (2009) this now seems to be a well-established fact (Engineering Materials and Processes, Metallic Fatigue, M. F. Ashby, PP 213-221, Butterworth-Heinemam, 2009). The results of this study correlate superior performance with extended ductility and not strength. For nitinol, more optimum fatigue performance correlates well with extended ductility, with elevated toughness and with lower values of critical stress for cross-slip; refer to Table 12B plus FIGS. 71-72.

Summary—Working Hypotheses

Plastic strain is the controlling parameter in each stage of fatigue; microstructures that homogenously distribute strain are desired.

Any microstructural feature that concentrates plastic strain or that results in an inhomogeneous distribution of plastic strains leads to undesirable local stress concentrations and large slip offsets at surfaces.

When large populations of sizable inclusions are present, which is typical for nitinol, loading may act to promote micro-cracks at the oxide/oxy-carbide inclusion-matrix interface thereby truncating the nucleation and initiation phases such that fatigue strength for those materials that possess such micro-cracks is ultimately governed by the ability of the material to resist crack growth and not by its ability to resist crack nucleation and initiation.

Conclusions

The plastic flow properties of nitinol tubes do not follow a simple power-law relationship instead; they exhibit dual-sloped plastic flow behavior irrespective of their heat-treated condition.

Ludwigson: $\sigma = K_1 \varepsilon^{n_1} + \exp(K_2 + n_2 \varepsilon)$ and Voce: $e = 1/n \ln((\sigma_s - \sigma)/k)$ equations have been used to accurately describe the observed plastic flow and strain-hardening behavior of as-drawn and heat-treated tubes ($R^2 > 0.99$).

The small diameter, mid diameter and large diameter Nitinol tubing from which the articles are fabricated exhibit different plastic flow behavior in their as-drawn condition with no post-draw thermo-mechanical shape-setting heat-treatment.

Different heat-treatment regimens emulating the thermal profiles of production article thermomechanical processing (heat-setting) result in different plastic flow behaviors.

The small diameter and large diameter tubes possess greater ductility and toughness than the mid diameter tubes regardless of heat-treatment.

Greater fatigue strength correlates with those heat-treatments which infer greater ductility and toughness.

The rank order of displacement-controlled fatigue performance of frames may be predicted based on parameters describing the plastic flow behavior acquired from uniaxial tensile testing of heat-treated tubing from which they are cut.

G. Overview of Various Aspects/Embodiments

A number of aspects are disclosed herein. Below is a summary of some of the aspects.

1. A method for decreasing the modulus of a structural element of an implantable medical device, wherein the element comprises a shape memory alloy (SMA), the method comprising: manipulating the SMA to (i) promote R-phase formation following implantation in a subject, or (ii) cause the R-phase and austenite phase to converge.

2. A method according to aspect 1, wherein manipulating the SMA further results in one or both of an increase in fatigue performance under displacement-controlled fatigue conditions or an increase in ductility.

3. A method for increasing fatigue performance of a structural element of an implantable medical device under displacement-controlled fatigue conditions, wherein the element comprises a shape memory alloy (SMA), the method comprising: manipulating the SMA to (i) promote R-phase formation following implantation in a subject, or (ii) cause the R-phase and austenite phase to converge.

4. A method according to aspect 3, wherein manipulating the SMA further results in one or both of a decrease in modulus or an increase in ductility.

5. A method for increasing ductility of a structural element of an implantable medical device, wherein the element comprises a shape memory alloy (SMA), the method comprising: manipulating the SMA to (i) promote R-phase formation following implantation in a subject, or (ii) cause the R-phase and austenite phase to converge.

6. A method according to any one of aspects 1-5, wherein manipulating the SMA comprises heat-treating the SMA to promote R-phase formation following implantation or to cause the R-phase and austenite phase to converge 7. A method according to aspect 6, wherein the heat treatment comprises heating the SMA at a temperature of 450° C. or greater.

8. A method according to aspect 6, wherein the heat treatment comprises heating the SMA at a temperature of 500° C. or greater.

9. A method according to aspect 6, wherein the heat treatment comprises heating the SMA at a temperature in a range from 450° C. to 550° C.

10. A method according to any one of aspects 6-9, wherein the heat-treatment is performed on the SMA without stress/strain tuning of the SMA.

11. A method according to any one of aspects 6-9, further comprising subjecting the SMA to stress/strain tuning during the heat treatment.

12. A method according to any one of aspects 1-11, wherein manipulating the SMA comprises introducing precipitates in the SMA to achieve a suitable grain size.

13. A method according to any one of aspects 1-12, wherein manipulating the SMA comprises altering the ratio of components of the SMA.

14. A method according to any one of aspects 1-13, wherein the structural element is formed to have a length-to-depth ratio of 8:1 or less.

15. A method according to any one of aspects 1-14, wherein the structural element is formed to have a non-uniform shape.

16. A method according to any one of aspects 1-15, wherein the structural element comprises at least one region that is narrower than another region.

17. A method for increasing the modulus of a structural element of an implantable medical device, wherein the element comprises a shape memory alloy (SMA), the method comprising: manipulating the SMA to (i) inhibit R-phase formation following implantation in a subject, or (ii) cause the R-phase and austenite phase to separate.

18. A method according to aspect 17, wherein the structural element comprises a fixation element.

19. A method according to aspect 17 or 18, wherein manipulating the SMA further results in one or both of a decrease in ductility and enhanced force-controlled fatigue performance.

20. A method for increasing force-controlled fatigue performance of a structural element of an implantable medical device, wherein the element comprises a shape memory alloy (SMA), the method comprising: manipulating the SMA to (i) inhibit R-phase formation following implantation in a subject, or (ii) cause the R-phase and austenite phase to separate.

21. A method according to aspect 20, wherein manipulating the SMA further results in a decrease in ductility.

22. A method for decreasing ductility of a structural element of an implantable medical device, wherein the element comprises a shape memory alloy (SMA), the method comprising: manipulating the SMA to (i) inhibit R-phase formation following implantation in a subject, or (ii) cause the R-phase and austenite phase to separate.

23. A method according to any one of aspects 17-22, wherein manipulating the SMA comprises heat-treating the SMA to inhibit R-phase formation following implantation or to cause the R-phase and austenite phase to separate 24. A method according to aspect 23, wherein the heat treatment comprises heating the SMA at a temperature of 525° C. or less.

25. A method according to aspect 23, wherein the heat treatment comprises heating the SMA at a temperature of 400° C. or less.

26. A method according to aspect 23, wherein the heat treatment comprises heating the SMA at a temperature in a range from 300° C. to 525° C.

27. A method according to any one of aspects 23-26, wherein the heat-treatment is performed on the SMA without stress/strain tuning of the SMA.

28. A method according to any one of aspects 23-26, further comprising subjecting the SMA to stress/strain tuning during the heat treatment.

29. A method according to any one of aspects 17-28, wherein manipulating the SMA comprises introducing precipitates in the SMA to achieve a suitable grain size.

30. A method according to any one of aspects 17-29, wherein manipulating the SMA comprises altering the ratio of components of the SMA.

31. A method according to any one of aspects 17-30, wherein the structural element is formed to have a length-to-depth ratio of 8:1 or greater.

32. A method according to any one of aspects 17-31, wherein the structural element is formed to have a uniform shape.

33. A method according to any one of aspects 1-32, wherein the SMA comprises Ni and Ti.

34. A method according to aspect 33, wherein the Ni and Ti are substantially equiatomic.

35. A method according to aspect 33 or 34, wherein the SMA further comprises a third metal.

36. A method according to aspect 35, wherein the third metal is iron.

37. A method according to any one of aspects 1-36, wherein the structural element comprises a heart valve frame or a component thereof.

38. A method for enhancing displacement-controlled fatigue performance, increasing ductility or decreasing modulus of a structural element of an implantable medical device, wherein the structural element comprises a shape memory alloy material, the method comprising: heating the structural element at a temperature between 580° C. and 620° C. for a time between 30 seconds and 500 minutes to produce a heat-treated structural element; and shape setting the heat-treated structural element.

39. A method according to aspect 38, wherein heating the structural element comprises heating the structural element at a temperature between 590° C. and 615° C.

40. A method according to aspect 38, wherein heating the structural element comprises heating the structural element at a temperature between 595° C. and 610° C.

41. A method according to any one of aspects 38-40, wherein the time for which the structural element is heated is between 60 seconds and 100 minutes.

42. A method according to any one of aspects 38-41, wherein the shape memory alloy comprises a NiTi alloy.

43. An implantable medical structural scaffold, comprising: a shape memory alloy (SMA) material, wherein the SMA material comprises an R-phase and an austenite phase transition temperature overlap.

44. An implantable medical device comprising: a structural scaffold formed from shape memory alloy (SMA) material, wherein the structural scaffold is configured to be compressed for delivery to a patient or post deployment recapture in a patient and expandable once delivered to the patient; and wherein shape-memory material structural scaffold has one or more of the following properties:
a critical stress for cross slip below the predetermined critical stress value;
a yield stress below the predetermined yield stress value;
a toughness greater than the predetermined toughness value;
a strain at ultimate tensile strength (UTS) greater than a predetermined value;
a UTS to yield strength ratio greater than a predetermined value; and
a saturation stress below a predetermined saturation stress value,
wherein the SMA material structural scaffold has superior fatigue-resistance relative to a substantially similar article having a critical stress for cross slip above the predetermined critical stress value, a yield stress above the predetermined yield strength value, a toughness less than the predetermined toughness value, a strain at ultimate tensile strength (UTS) less than the predetermined value, a UTS to yield strength ratio less than the predetermined value, or a saturation stress above the predetermined saturation stress value.

45. An implantable medical device according to aspect 44, wherein the SMA material structural scaffold has two or more of the following properties:
a critical stress for cross slip below the predetermined critical stress value;
a yield stress below the predetermined yield stress value;
a toughness greater than the predetermined toughness value;
a strain at ultimate tensile strength (UTS) greater than a predetermined value;
a UTS to yield strength ratio greater than the predetermined value; and
a saturation stress below a predetermined saturation stress value.

46. An implantable medical device according to claim 44, wherein the SMA material structural scaffold has:
a critical stress for cross slip below a predetermined critical stress value;
a yield stress below a predetermined yield stress value;
a toughness greater than the predetermined toughness value;
a strain at ultimate tensile strength (UTS) greater than a predetermined value;
a UTS to yield strength ratio greater than the predetermined value, and
a saturation stress below a predetermined saturation stress value.

47. An implantable medical device according to any one of aspects 44-46, wherein the SMA material structural scaffold has a critical stress for cross slip below the predetermined critical stress value.

48. An implantable medical device according to any one of aspects 44-47, wherein the critical stress is determined from the intersection of tangent lines of transitions from a plot of strain hardening $\Theta$ ($\delta\sigma_P/\delta\varepsilon_P$) versus plastic stress ($\sigma_P$).

49. A method according to any one of aspects 44-48, wherein the critical stress is determined from the mathematical solution of equations describing the transitions from a plot of rate of strain hardening $\Theta$ ($\delta\sigma_P/\delta\varepsilon_P$) versus plastic stress ($\sigma_P$).

50. A method according to any one of aspects 44-49, wherein the critical stress is determined from the intersection of tangent lines of transitions from a plot of log-log plot of rate of strain hardening $\Theta$ ($\delta\sigma_P/\delta\varepsilon_P$) versus plastic strain ($\varepsilon_P$).

51. A method according to any one of aspects 44-50, wherein the critical stress is determined from the mathematical solution of equations describing the transitions from a plot of log-log plot of rate of strain hardening $\Theta$ ($\delta\sigma_P/\delta\varepsilon_P$) versus plastic strain ($\varepsilon_P$).

52. An implantable medical device according to any one of aspects 44-51, wherein the wherein the SMA material structural scaffold has a yield stress below the predetermined yield stress value.

53. An implantable medical device according to any one of aspects 44-52, wherein the SMA material structural scaffold has a toughness greater than the predetermined toughness value.

54. An implantable medical device according to any one of aspects 44-53, wherein the SMA material structural scaffold has a strain at ultimate tensile strength (UTS) greater than predetermined value.

55. An implantable medical device according to any one of aspects 44-54, wherein the SMA is heat-treated.

56. An implantable medical device according to any one of aspects 44-55, wherein the SMA comprises Ni and Ti.

57. An implantable medical device according to aspect 56, wherein the nitinol comprises about equiatomic Ni and Ti.

58. An implantable medical device according to any one of aspects 44-57, wherein the SMA material structural scaffold is formed from a wrought SMA material.

59. An implantable medical device according to any one of aspects 44-58, wherein the SMA material structural scaffold is formed from a drawn tube, a wire, a sheet, a plate, or a ribbon of SMA material.

60. An implantable medical device according to any one of aspects 44-59, wherein the device is selected from the group consisting of a heart valve, a stent, and a vascular graft.

61. An implantable medical device according to any one of aspects 44-61, wherein the device employs the shape-memory material structural scaffold for anchoring or fixation.

62. An implantable medical device comprising: an expandable structural scaffold formed from SMA material, wherein the SMA material structural scaffold has one or more of the following properties:
  a critical stress for cross slip below a predetermined critical stress value;
  a yield stress below a predetermined yield stress value;
  a toughness greater than the predetermined toughness value;
  a strain at ultimate tensile strength (UTS) greater than a predetermined value;
  a UTS to yield strength ratio greater than a predetermined value; and
  a saturation stress below a predetermined saturation stress value.
  wherein the SMA material structural scaffold has superior fatigue-resistance relative to a substantially similar article having a critical stress for cross slip above the predetermined critical stress value, a yield strength above the predetermined yield strength value, a toughness less than the predetermined toughness value, a strain at ultimate tensile strength (UTS) less than the predetermined value, a UTS to yield strength ratio less than the predetermined value, or a saturation stress above the predetermined saturation stress value.

63. An implantable medical device according to aspect 62, wherein the SMA material is heat-treated nitinol.

64. An article comprising: an expandable structural scaffold formed from SMA material, wherein the SMA material structural scaffold has two or more of the following properties:
  a critical stress for cross slip below a predetermined critical stress value;
  a yield stress below a predetermined yield stress value;
  a toughness greater than the predetermined toughness value;
  a strain at ultimate tensile strength (UTS) greater than a predetermined value;
  a UTS to yield strength ratio greater than a predetermined value; and
  a saturation stress below a predetermined saturation stress value,
  wherein the SMA material structural scaffold has superior fatigue-resistance relative to a substantially similar article having a critical stress for cross slip above the predetermined critical stress value, a yield strength above the predetermined yield strength value, a toughness less than the predetermined toughness value, and a strain at ultimate tensile strength (UTS) less than the predetermined value, a UTS to yield strength ratio less than the predetermined value, or a saturation stress above the predetermined saturation stress value.

65. An implantable medical device according to aspect 64, wherein the SMA material is heat-treated nitinol.

66. An article comprising: an expandable structural scaffold formed from SMA material, wherein the SMA material structural scaffold has three or more of the following properties:
  a critical stress for cross slip below a predetermined critical stress value;
  a yield stress below a predetermined yield stress value;
  a toughness greater than the predetermined toughness value;
  a strain at ultimate tensile strength (UTS) greater than a predetermined value;
  a UTS to yield strength ratio greater than a predetermined value; and
  a saturation stress below a predetermined saturation stress value,
  wherein the SMA material structural scaffold has superior fatigue-resistance relative to a substantially similar article having a critical stress for cross slip above the predetermined critical stress value, a yield stress above the predetermined yield stress value, a toughness less than the predetermined toughness value, a strain at ultimate tensile strength (UTS) less than the predetermined value, a UTS to yield strength ratio less than the predetermined value; or a saturation stress above the predetermined saturation stress value.

67. An implantable medical device according to aspect 66, wherein the SMA material is heat-treated nitinol.

68. An article comprising: a structural scaffold formed from SMA material, wherein the structural scaffold is configured to be compressed for delivery to a patient and expandable once delivered to the patient; and wherein the SMA material structural scaffold is characterized as being ductile and has one or more of the following properties:
  a critical stress for cross slip below a predetermined critical stress value;
  a yield stress below a predetermined yield stress value;
  a toughness greater than the predetermined toughness value;
  a strain at ultimate tensile strength (UTS) greater than a predetermined value;
  a UTS to yield strength ratio greater than a predetermined value; and
  a saturation stress below a predetermined saturation stress value,
  wherein the SMA material structural scaffold has superior fatigue-resistance relative to a substantially similar article having a critical stress for cross slip above the predetermined critical stress value, a yield strength above the predetermined yield strength value, a toughness less than the predetermined toughness value, a strain at ultimate tensile strength (UTS) less than the predetermined value, a UTS to yield strength ratio less than the predetermined value; or a saturation stress below above the predetermined saturation stress value.

69. An implantable medical device according to aspect 68, wherein the SMA material is heat-treated nitinol.

70. A method for selecting a production SMA article predicted to have enhanced fatigue resistance, wherein the production SMA article is configured to be compressed prior to use and expanded for use, the method comprising: subjecting a surrogate SMA article to thermo-mechanical shape-setting procedures to which the production SMA article will be, or has been, subjected to achieve a heat-treated surrogate SMA article, the surrogate SMA article being essentially the same as the production SMA article; obtaining uniaxial stress-strain data of the heat-treated surrogate SMA article; selecting the production SMA article as an article predicted to have enhanced fatigue resistance if the uniaxial stress-strain data of the heat-treated surrogate SMA article indicates one or more of:

a critical stress for cross slip below a predetermined critical stress value;
a yield stress below a predetermined yield stress value;
a toughness greater than the predetermined toughness value;
a strain at ultimate tensile strength (UTS) greater than a predetermined value;
a UTS to yield strength ratio greater than a predetermined value; and
a saturation stress below a predetermined saturation stress value.

71. A method according to aspect 70, wherein the production SMA article is selected as an article predicted to have enhanced fatigue resistance if the uniaxial stress-strain data of the heat-treated surrogate SMA article indicates two or more of:
a critical stress for cross slip below a predetermined critical stress value;
a yield stress below a predetermined yield stress value;
a toughness greater than the predetermined toughness value;
a strain at ultimate tensile strength (UTS) greater than a predetermined value;
a UTS to yield strength ratio greater than a predetermined value; and
a saturation stress below a predetermined saturation stress value.

72. A method according to aspect 71, wherein the production SMA article is selected as an article predicted to have enhanced fatigue resistance if the uniaxial stress-strain data of the heat-treated surrogate SMA article indicates:
a critical stress for cross slip below a predetermined critical stress value;
a yield stress below a predetermined yield stress value;
a toughness greater than the predetermined toughness value;
a strain at ultimate tensile strength (UTS) greater than a predetermined value;
a UTS to yield strength ratio greater than a predetermined value; and
a saturation stress below a predetermined saturation stress value.

73. A method according to any of aspects 70-72, wherein the selecting the production SMA article as an article predicted to have enhanced fatigue resistance comprises selecting the article if the uniaxial stress-strain data of the heat-treated surrogate SMA article indicates a critical stress for cross slip below the predetermined critical stress value.

74. A method according to any of aspects 70-73, wherein the selecting the production SMA article as an article predicted to have enhanced fatigue resistance comprises selecting the article if the uniaxial stress-strain data of the heat-treated surrogate SMA article indicates a critical stress for cross slip below a predetermined critical stress value and a yield stress below the predetermined yield stress value.

75. A method according to any of aspects 70-74, wherein the production SMA article is selected as an article predicted to have enhanced fatigue resistance if the uniaxial stress-strain data of the heat-treated surrogate SMA article further indicates a toughness greater than a predetermined toughness value.

76. A method according to any of aspects 70-75, wherein the production SMA article is selected as an article predicted to have enhanced fatigue resistance if the uniaxial stress-strain data of the heat-treated surrogate SMA article further indicates a strain at ultimate tensile strength (UTS) greater than a predetermined value.

77. A method according to any of aspects 70-76, wherein the critical stress is determined from the intersection of tangent lines of transitions from a plot of strain hardening $\Theta$ ($\delta\sigma_P/\delta\varepsilon_P$) versus plastic stress ($\sigma_P$).

78. A method according to aspect 77, wherein the critical stress is determined from the intersection of tangent lines of transitions from a plot of log-log plot of rate of strain hardening $\Theta$ ($\delta\sigma_P/\delta\varepsilon_P$) versus plastic strain ($\varepsilon_P$).

79. A method according to any of aspects 70-78, wherein the critical stress is determined from the mathematical solution of equations describing the transitions from a plot of rate of strain hardening $\Theta$ ($\delta\sigma_P/\delta\varepsilon_P$) versus plastic stress ($\sigma_P$).

80. A method according to aspect 79, wherein the critical stress is determined from the mathematical solution of equations describing the transitions from a plot of log-log plot of rate of strain hardening $\Theta$ ($\delta\sigma_P/\delta\varepsilon_P$) versus plastic strain ($\varepsilon_P$).

81. A method according to any of aspects 70-80, wherein the SMA is nitinol.

82. A method according to aspect 81, wherein the nitinol comprises about equiatomic Ni and Ti.

83. A method according to aspects 70-82, wherein the SMA article and the production SMA article are formed from a wrought SMA material.

84. A method according to aspects 70-83, wherein the surrogate SMA article and the production SMA article are formed from a drawn tube, a wire, a sheet, a plate, or a ribbon of shape-memory material.

85. A method according to any of aspects 70-84, further comprising preloading the surrogate SMA article prior to obtaining uniaxial stress-strain data.

86. A method according to aspect 42, wherein the preloading comprises about 5% to about 10% preloading.

87. A method according to any of aspects 27-43, wherein the surrogate SMA article is a simplified shape analogue of the production SMA article.

88. A method for predicting fatigue performance of a shape memory alloy (SMA) article, comprising: obtaining uniaxial stress-strain data of the article or a surrogate thereof; and predicting the fatigue performance of the article based on data acquired from the work-hardening portion of the stress-strain curve.

89. A method for down selecting wrought materials as a means of promoting optimized fatigue performance of a shape memory alloy (SMA) article, comprising: obtaining uniaxial stress-strain data of the wrought material article or a surrogate thereof; and predicting the fatigue performance of the article based on data acquired from the work-hardening portion of the stress-strain curve.

90. A method for optimizing heat-treatment processing as a means of promoting optimized fatigue performance of a shape memory alloy (SMA) article, comprising: obtaining uniaxial stress-strain data of the heat-treated article or a surrogate thereof; and predicting the fatigue performance of the article based on data acquired from the work-hardening portion of the stress-strain curve.

Thus, embodiments of SHAPE MEMORY ARTICLES AND METHODS FOR CONTROLLING PROPERTIES are disclosed. One skilled in the art will appreciate that the compounds, compositions, articles, systems, methods, and the like described herein can be practiced with embodiments other than those disclosed. The disclosed embodiments are presented for purposes of illustration and not limitation.

What is claimed is:

1. A method for enhancing displacement-controlled fatigue performance, increasing ductility or decreasing modulus of a structural element of an implantable medical device, wherein the structural element comprises a shape memory alloy material, the method comprising:

a first step consisting essentially of: heating the structural element at a temperature between 580° C. and 620° C. for a time between 30 seconds and 500 minutes to produce a heat-treated structural element; and a second step comprising: shape setting the heat-treated structural element after the structural element is heated.

2. The method of claim 1, wherein heating the structural element comprises heating the structural element at a temperature between 590° C. and 615° C.

3. The method of claim 1, wherein heating the structural element comprises heating the structural element at a temperature between 595° C. and 610° C.

4. The method of claim 1, wherein the time for which the structural element is heated is between 60 seconds and 100 minutes.

5. The method of claim 1, wherein the shape memory alloy comprises a NiTi alloy.

* * * * *